US011306331B2

(12) United States Patent
Jendresen et al.

(10) Patent No.: US 11,306,331 B2
(45) Date of Patent: Apr. 19, 2022

(54) PROCESSES FOR THE PRODUCTION OF HYDROXYCINNAMIC ACIDS USING POLYPEPTIDES HAVING TYROSINE AMMONIA LYASE ACTIVITY

(71) Applicant: CysBio ApS, Hørsholm (DK)

(72) Inventors: Christian Bille Jendresen, Copenhagen (DK); Solvej Siedler, Kokkedal (DK); Steen Gustav Stahlhut, Frederiksberg (DK); Alex Toftgaard Nielsen, Rungsted Kyst (DK)

(73) Assignee: CYSBIO APS, Kgs. Lyngby (DK)

( * ) Notice: Subject to any disclaimer, the term of this patent is extended or adjusted under 35 U.S.C. 154(b) by 0 days.

(21) Appl. No.: 16/938,762

(22) Filed: Jul. 24, 2020

(65) Prior Publication Data
US 2020/0399665 A1 Dec. 24, 2020

Related U.S. Application Data

(63) Continuation of application No. 15/325,679, filed as application No. PCT/EP2015/066067 on Jul. 14, 2015, now Pat. No. 10,752,923.

(30) Foreign Application Priority Data

Jul. 14, 2014 (EP) ..................................... 14176975
Mar. 23, 2015 (EP) ..................................... 15160398

(51) Int. Cl.
*C12P 7/42* (2006.01)
*C12N 9/88* (2006.01)

(52) U.S. Cl.
CPC .................. *C12P 7/42* (2013.01); *C12N 9/88* (2013.01); *C12Y 403/01023* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 6,255,088 | B1 | 7/2001 | Wong et al. |
| 7,531,341 | B1 | 5/2009 | Vellard et al. |
| 2005/0260724 | A1 | 11/2005 | Ben-Bassat et al. |
| 2009/0047265 | A1 | 2/2009 | Kakkis et al. |
| 2012/0177722 | A1 | 7/2012 | Weiner |

FOREIGN PATENT DOCUMENTS

WO WO 01/85971 A2 11/2001

OTHER PUBLICATIONS

Appert et al., "Structural and catalytic properties of the four phenylalanine ammonia-lyase isoenzymes from parsley (*Petroselinum crispum* Nym.)" Eur. J. Biochem., 1994, pp. 491-499, vol. 225.

Barthelmebs et al. Appl. Environ. Microbiol. 67:1063-1069, 2001.
Bartsch et al., "A Single Residue Influences the Reaction Mechanism of Ammonia Lyases and Mutases" Angew. Chem. Int. Ed., 2009, pp. 3362-3365, vol. 48.
Bartsch et al., "Redesign of a Phenylalanine Aminomutase into a Phenylalanine Ammonia Lyase" Heterogeneous & Homogeneous & Bio-Chemcatchem Catalysis—Supporting Information, 2013, pp. S1-S11.
Bartsch et al., "Redesign of a Phenylalanine Aminomutase into a Phenylalanine Ammonia Lyase" Chemcatchem, 2013, pp. 1797-1802, vol. 5.
Berner et al., "Genes and Enzymes Involved in Caffeic Acid Biosynthesis in the Actinomycete *Saccharothrix espanaensis*" Journal of Bacteriology, Apr. 2006, pp. 2666-2673, vol. 188, No. 7.
Chesters et al., "Thermal Bifunctionality of Bacterial Phenylalanine Aminomutase and Ammonia Lyase Enzymes" Angew. Chem. Int. Ed., 2012, pp. 4344-4348, vol. 51.
Christenson et al., "A Novel 4-Methylideneimidazole-5-one-Containing Tyrosine Aminomutase in Enediyne Antitumor Antibiotic C-1027 Biosynthesis" J. Am. Chem. Soc., 2003, pp. 6062-6063, vol. 125.
Christenson et al., "Kinetic Analysis of the 4-Methylideneimidazole-5-one-Containing Tyrosine Aminomutase in Enediyne Antitumor Antibiotic C-1027 Biosynthesis" Biochemistry, 2003, pp. 12708-12718, vol. 42.
Holo et al., "Transformation of Lactococcus by Electroporation" Methods in Molecular Biology, 1995, pp. 195-199, vol. 47.
Horinouchi et al., "Nucleotide Sequence and Functional Map of pC194, a Plasmid That Specifies Inducible Chloramphenicol Resistance" Journal of Bacteriology, May 1982, pp. 815-825, vol. 150, No. 2.
Jendresen et al., "Highly Active and Specific Tyrosine Ammonia-Lyases from Diverse Origins Enable Enhanced Production of Aromatic Compounds in Bacteria and *Saccharomyces cerevisiae*" Applied and Environmental Microbiology, Jul. 2015, pp. 4458-4476, vol. 81, No. 13.
Jensen et al., "EasyClone: method for iterative chromosomal integration of multiple genes in *Saccharomyces cerevisiae*" FEMS Yeast Res., 2013, pp. 238-248, vol. 14, No. 2.
Jin et al., "A Biosynthetic Gene Cluster for the Acetyl-CoA Carboxylase Inhibitor Andrimid" J Am Chem Soc., Aug. 23, 2006; pp. 10660-10661, vol. 128, No. 33.
Kuipers et al., "Quorum sensing-controlled gene expression in lactic acid bacteria" Journal of Biotechnology, 1998, pp. 15-21, vol. 64.

(Continued)

*Primary Examiner* — David Steadman
(74) *Attorney, Agent, or Firm* — Knobbe, Martens, Olson & Bear LLP

(57) ABSTRACT

The present invention generally relates to the field of biotechnology as it applies to the production of hydroxycinnamic acids using polypeptides having tyrosine ammonia lyase activity. More particularly, the present invention pertains to polypeptides having tyrosine ammonia lyase activity and high substrate specificity towards tyrosine, which makes them particularly suitable in the production of p-coumaric acid and other hydroxycinnamic acids. The present invention thus provides processes for the production of p-coumaric acid and other hydroxycinnamic acids employing these polypeptides as well as recombinant host cells expressing same.

23 Claims, 9 Drawing Sheets

Specification includes a Sequence Listing.

(56) References Cited

OTHER PUBLICATIONS

Kyndt et al., "Characterization of a bacterial tyrosine ammonia lyase, a biosynthetic enzyme for the photoactive yellow protein" FEBS Letters, 2002, pp. 240-244, vol. 512.

Poolman et al., "Relation of Growth of *Streptococcus lactis* and *Streptococcus cremoris* to Amino Acid Transport" Journal of Bacteriology, Feb. 1988, pp. 700-707, vol. 170, No. 2.

Qi et al., "Functional expression of prokaryotic and eukaryotic genes in *Escherichia coli* for conversion of glucose to p-hydroxystyrene" Metabolic Engineering, 2007, pp. 268-276, vol. 9.

Rösler et al., "Maize Phenylalanine Ammonia-Lyase Has Tyrosine Ammonia-Lyase Activity" Plant Physiol., 1997, pp. 175-179, vol. 113.

Schroeder, Amy C. et al., "Contributions of conserved serine and tyrosine residues to catalysis, ligand binding, and cofactor processing in the active site of tyrosine ammonia lyase" Phytochemistry, 2008, pp. 1496-1506, vol. 69.

Strobel et al., "Complete genome sequence of Saccharothrix espanaensis DSM 44229T and comparison to the other completely sequenced Pseudonocardiaceae" BMC Genomics, 2012, pp. 1-13, vol. 13, No. 465.

Walker et al., "Cloning, Heterologous Expression, and Characterization of a Phenylalanine Aminomutase Involved in Taxol Biosynthesis" The Journal of Biological Chemistry, Dec. 24, 2004, pp. 53947-53954, vol. 279, No. 52.

Williams et al., "The gene stlA encodes a phenylalanine ammonia-lyase that is involved in the production of a stilbene antibiotic in *Photorhabdus luminescens* TT01" Microbiology, 2005, pp. 2543-2550, vol. 151.

Xiang et al., "Inactivation, Complementation, and Heterologous Expression of encP, a Novel Bacterial Phenylalanine Ammonia-Lyase Gene" The Journal of Biological Chemistry, Sep. 6, 2002, pp. 32505-32509, vol. 277, No. 36.

Zhu et al., "Cloning and characterization of a novel tyrosine ammonia lyase-encoding gene involved in bagremycins biosynthesis in *Streptomyces* sp." Biotechnol Lett., 2012, pp. 269-274, vol. 34.

Zhu et al., "Cloning, expression and characterization of phenylalanine ammonia-lyase from *Rhodotorula glutinis*" Biotechnol Lett., 2013, pp. 751-756, vol. 35.

XP-002734244—"SubName: Full=Histidine ammonia-lyase; EC=4.3.1.3" Jun. 12, 2007.

XP-002734245—"SubName: Full=Histidine ammonia-lyase; EC=4.3.1.3" Jan. 15, 2008.

XP-002734246—"SubName: Full=Histidine ammonia-lyase; EC=4.3.1.3" Jan. 15, 2008.

International Search Report for PCT/EP2015/066067 dated Sep. 28, 2015.

PROCESSES FOR THE PRODUCTION OF HYDROXYCINNAMIC ACIDS USING POLYPEPTIDES HAVING TYROSINE AMMONIA LYASE ACTIVITY

CROSS REFERENCE TO RELATED APPLICATIONS

This application is a continuation of U.S. patent application Ser. No. 15/325,679, filed on Jan. 11, 2017, which issued as U.S. Pat. No. 10,752,923 on Aug. 25, 2020, which is a U.S. National Phase Application of PCT International Application Number PCT/EP2015/066067, filed on Jul. 14, 2015, designating the United States of America and published in the English language, which is an International Application of and claims the benefit of priority to European Patent Application No. 14176975.2, filed on Jul. 14, 2014, and European Patent Application No. 15160398.2, filed on Mar. 23, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-ZACCO188.001C1.txt, the date of creation of the ASCII text file is Jul. 23, 2020, and the size of the ASCII text file is 46 KB.

FIELD OF THE INVENTION

The present invention generally relates to the field of biotechnology as it applies to the production of hydroxycinnamic acids using polypeptides having tyrosine ammonia lyase activity. More particularly, the present invention pertains to polypeptides having high tyrosine ammonia lyase activity and high substrate specificity towards tyrosine, which makes them particularly suitable for the production of p-coumaric acid and other hydroxycinnamic acids. The present invention thus provides processes for the production of p-coumaric acid and other hydroxycinnamic acids employing these polypeptides as well as recombinant host cells expressing same.

BACKGROUND OF THE INVENTION

Small organic molecules of interest to the biotech industry often involve aromatic structures that are derived from p-coumaric acid (pHCA) or other hydroxycinnamic acids. In particular, pHCA is a precursor for many secondary metabolites including flavonoids and stilbenes, and has a significant potential as a building block for producing polymers. pHCA is naturally formed from phenylalanine by subsequent ammonialyase and hydroxylase reactions or directly from tyrosine by the deamination of tyrosine.

Aromatic amino acid lyases constitute an enzymatic family, and are classified by their substrate specificity as being histidine ammonia-lyases (HAL, EC 4.3.1.3), tyrosine ammonia-lyases (TAL, EC 4.3.1.23), phenylalanine ammonia-lyases (PAL, EC 4.3.1.24) or phenylalanine/tyrosine ammonia-lyases (PAL/TAL, EC 4.3.1.25). Enzymes categorized as acting on either of the structurally similar amino acids tyrosine or phenylalanine are normally having some activity towards the other (Rosler et al., 1997; Zhu et al., 2013). Similar enzymatic families are tyrosine 2,3-aminomutases (TAM, EC 5.4.3.6) and phenylalanine aminomutase (PAM, EC 5.4.3.11) (Christenson et al., 2003a; Jin et al., 2006). All of these proteins contain a prosthetic group, 3,5-dihydro-5-methylidene-4H-imidazol-4-one (MIO) formed by the cyclization of the sequential three amino acids alanine, serine and glycine. TAMs as well as PAMs have been shown to have background lyase activity (Christenson et al., 2003b; Walker et al., 2004). The lyase and mutase activities of a single enzyme may be subject to a thermal switch (Chesters et al., 2012), and mutations can divert the enzymatic activity of a PAM into higher PAL activity (Bartsch et al., 2013). Aminomutases have been found in the biosynthetic pathways to antitumor drug compounds.

A number of tyrosine ammonia lyases have been cloned and functionally characterized: While PAL and TAL activities had been shown in plant extracts previously, Kyndt et al (Kyndt et al., 2002) identified and characterized the first TAL enzyme, originating from the purple non-sulfur bacterium *Rhodobacter capsulatus*, which uses pHCA as a chromophore in the light-sensing photoactive yellow protein (PYP). The actinomycete *Saccharothrix espanaensis* produce two related oligosaccharide antibiotics saccharomicin A and B, both containing a substructure derived from pHCA, which is formed by the sam8 gene of the antibiotic biosynthetic gene cluster (Berner et al., 2006; Strobel et al., 2012). EncP is a PAL playing a role in the biosynthetic pathway to enterocin in *Streptomyces maritimus* (Xiang; Moore, 2002), and recently, another TAL was identified in an actinomycete, namely bagA in *Streptomyces* sp. TO 4128 (Zhu et al., 2012), and as a part of biosynthetic route to bagremycin A and B. stlA of *Photorhabdus luminescens* is also part of an antibiotic biosynthetic pathway, yet StlA has PAL activity (Williams et al., 2005). A number of the TALs have been purified and enzymatically characterized (Appert et al., 1994; Rosler et al., 1997; Kyndt et al., 2002; Christenson et al., 2003b; Williams et al., 2005; Berner et al., 2006; Schroeder et al., 2008; Bartsch; Bornscheuer, 2009).

TAL enzymatic activity has been described in patent literature and in particular the enzymes of the yeast genus *Rhodotorula*, the yeasts *Phanerochaete chrysosporium* and *Trichosporon cutaneum*, and the purple non-sulfur bacteria *Rhodobacter sphaeroides* and capsulatus. However, since these enzymes also show some specificity towards phenylalanine, they are not particularly useful in the production of p-coumaric acid and other hydroxycinnamic acids due to accompanying contamination by cinnamic acid as a result of the deamination of phenylalanine.

Accordingly, there is a need in the art for biological processes which allow the production of p-coumaric acid and other hydroxycinnamic acids at high yield and high purity. This need is solved by the present invention.

SUMMARY OF THE INVENTION

The present invention is based on the identification of enzymes of bacterial origin, which show higher TAL activity compared to previously characterized enzymes. The identified enzymes show improved specificity and productivity, and thus allow the enhanced biologically production of hydroxycinnamic acids such as pHCA.

The present invention thus provides in a first aspect a method for producing a hydroxycinnamic acid of general formula I

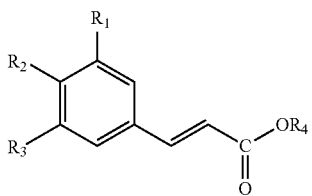

general formula I the method comprises deaminating a compound of general formula

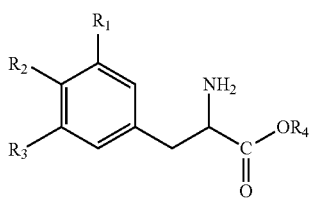

general formula II wherein $R_1$, $R_2$ and $R_3$ independently are selected from the group consisting of hydrogen (H), hydroxyl (—OH), $C_{1-6}$-alkyl and $C_{1-6}$-Alkoxy, provided that at least one of $R_1$, $R_2$ and $R_3$ is hydroxyl (—OH); and $R_4$ is selected from the group consisting of hydrogen (—H) and $C_{1-6}$-alkyl;

using a polypeptide as detailed herein. Particularly, the method involves the use of a polypeptide selected from the group consisting of:

i) a polypeptide comprising an amino acid sequence set forth in SEQ ID NO: 1, 2 or 3 (e.g. SEQ ID NO: 1);

ii) a polypeptide comprising an amino acid sequence which has at least about 70%, such as at least about 75%, at least about 80%, at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3 (e.g. SEQ ID NO: 1); or iii) a polypeptide comprising an amino acid sequence set forth in SEQ ID NO: 1, 2 or 3 (e.g. SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted, and/or inserted.

The present invention provides in a further aspect a recombinant host cell comprising a polypeptide as detailed herein. Particularly, the recombinant host cell according to the present invention comprises a heterologous polypeptide selected from the group consisting of:

i) a polypeptide comprising an amino acid sequence set forth in SEQ ID NO: 1, 2 or 3 (e.g. SEQ ID NO: 1);

ii) a polypeptide comprising an amino acid sequence which has at least about 70%, such as at least about 75%, at least about 80%, at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3 (e.g. SEQ ID NO: 1); or iii) a polypeptide comprising an amino acid sequence set forth in SEQ ID NO: 1, 2 or 3 (e.g. SEQ ID NO: 1), wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted.

The present invention provides in yet a further aspect a method for producing a hydroxycinnamic acid of general formula I comprising the step of contacting a recombinant host cell as detailed herein with a medium comprising a compound of the general formula II.

The method may further comprise the step culturing the recombinant host cell under suitable conditions for the production of the hydroxycinnamic acid, and further optionally the recovery of the hydroxycinnamic acid.

The present invention provides in yet a further aspect the use of a polypeptide as detailed herein in the production of a hydroxycinnamic acid of general formula I, and particularly in the production of p-coumaric acid.

DETAILED DESCRIPTION OF THE INVENTION

Figure 1:
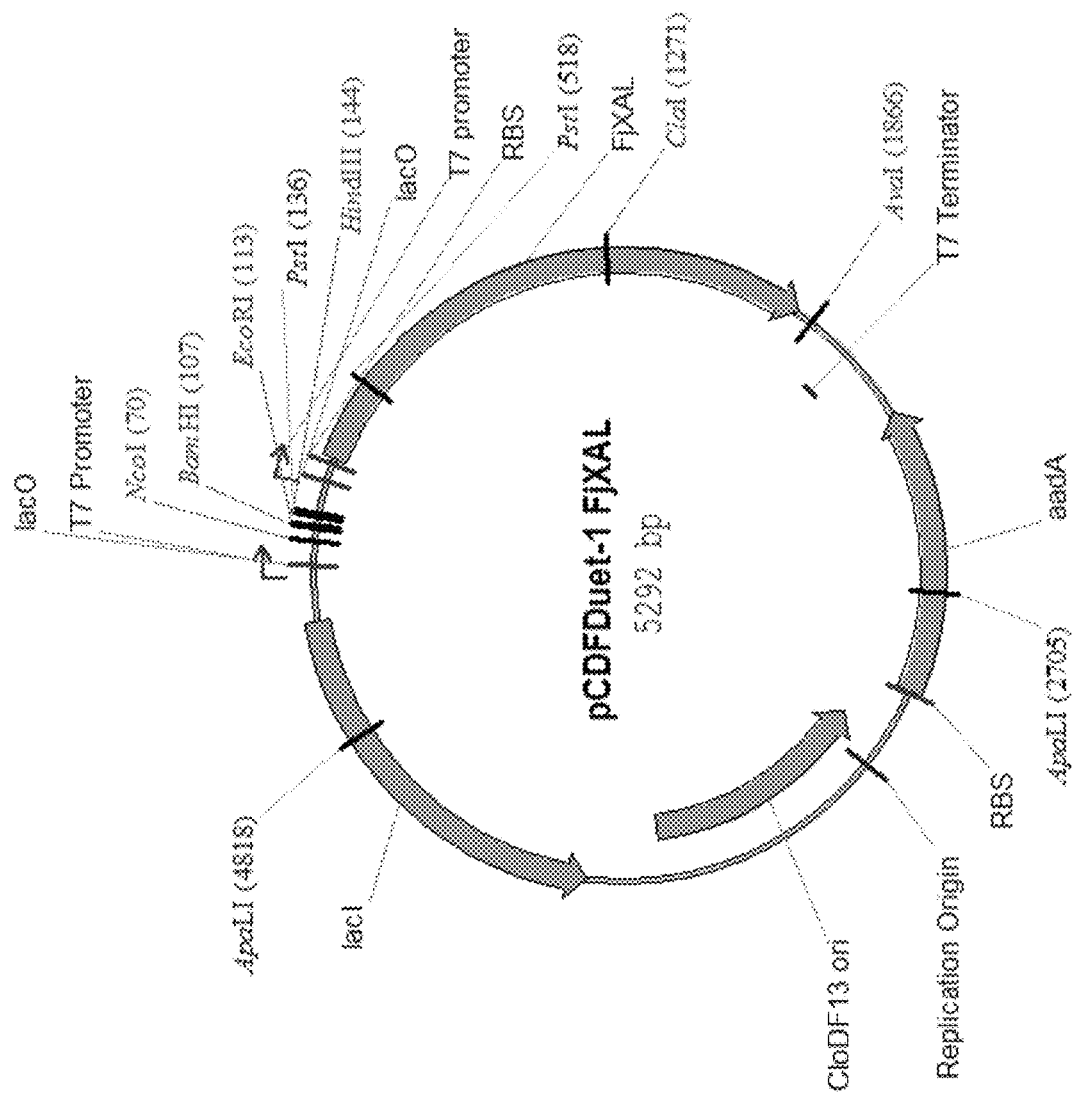
FIG. 1: Map of plasmid for expression of FjXAL in *E. coli*

Unless specifically defined herein, all technical and scientific terms used have the same meaning as commonly understood by a skilled artisan in the fields of biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Polypeptides and Host Cells

As indicated above, the present invention provides and utilizes polypeptides having tyrosine ammonia lyase activity and high substrate specificity towards tyrosine. This makes them particularly suitable for the production of p-coumaric acid and other hydroxycinnamic acids.

Particularly, the polypeptides employed according to the invention are polypeptides selected from the group consisting of:
  i) a polypeptide comprising an amino acid sequence set forth in SEQ ID NO: 1, 2 or 3 (e.g., SEQ ID NO: 1);
  ii) a polypeptide comprising an amino acid sequence which has at least about 70%, such as at least about 75%, at least about 80%, at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3 (e.g., SEQ ID NO: 1); or
  iii) a polypeptide comprising an amino acid sequence set forth in SEQ ID NO: 1, 2 or 3 (e.g., SEQ ID NO: 1), wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted.

According to certain embodiments, a polypeptide according to the invention is a polypeptide according to i). Accordingly, a polypeptide according to the invention may be a polypeptide comprising an amino acid sequence set forth in SEQ ID NO: 1, 2 or 3 (e.g., SEQ ID NO: 1). According to particular embodiments, a polypeptide according to i) comprises an amino acid sequence set forth in SEQ ID NO: 1. According other particular embodiments, a polypeptide according to i) comprises an amino acid sequence set forth in SEQ ID NO: 2. According to yet other particular embodiments, a polypeptide according to i) comprises an amino acid sequence set forth in SEQ ID NO: 3.

According to other certain embodiments, a polypeptide according to the invention is a polypeptide according to ii). Accordingly, a polypeptide according to the invention may be a polypeptide comprising an amino acid sequence which has at least about 70%, such as at least about 75%, at least about 80%, at least about 85%, at least about 90%, at least about 93%, at least 95%, at least about 96%, at least about 97%, at least about 98%, or at least about 99%, sequence identity to the amino acid sequence set forth in SEQ ID NO: 1, 2 or 3 (e.g., SEQ ID NO: 1).

According to particular embodiments, a polypeptide according to ii) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3 (e.g., SEQ ID NO: 1). According to other particular embodiments, a polypeptide according to ii) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 1, 2 or 3 (e.g., SEQ ID NO: 1). According to other particular embodiments, a polypeptide according to ii) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 1, 2 or 3 (e.g., SEQ ID NO: 1). According to other particular embodiments, a polypeptide according to ii) comprises an amino acid sequence which has at least about 95%, such as at least about 96%, at least about 97%, at least about 98%, or at least about 99%, sequence identity to the amino acid sequence set forth in SEQ ID NO: 1, 2 or 3 (e.g., SEQ ID NO: 1).

According to particular embodiments, a polypeptide according to ii) comprises an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1. According to more particular embodiments, a polypeptide according to ii) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to ii) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to ii) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to ii) comprises an amino acid sequence which has at least about 95%, such as at least about 96%, at least about 97%, at least about 98%, or at least about 99%, sequence identity to the amino acid sequence set forth in SEQ ID NO: 1.

According to particular embodiments, a polypeptide according to ii) comprises an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 2. According to more particular embodiments, a polypeptide according to ii) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 2. According to other more particular embodiments, a polypeptide according to ii) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 2. According to other more particular embodiments, a polypeptide according to ii) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 2. According to other more particular embodiments, a polypeptide according to ii) comprises an amino acid sequence which has at least about 95%, such as at least about 96%, at least about 97%, at least about 98%, or at least about 99%, sequence identity to the amino acid sequence set forth in SEQ ID NO: 2.

According to particular embodiments, a polypeptide according to ii) comprises an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 3. According to more particular embodiments, a polypeptide according to ii) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 3. According to other more particular embodiments, a polypeptide according to ii) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 3. According to other more particular embodiments, a polypeptide according to ii) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 3. According to other more particular embodiments, a polypeptide according to the invention comprises an amino acid sequence which has at least about 95%, such as at least about 96%, at least about 97%, at least about 98%, or at least about 99%, sequence identity to the amino acid sequence set forth in SEQ ID NO: 3.

Preferably, a polypeptide according to ii) has tyrosine ammonia lyase activity. More preferably, a polypeptide according to ii) has a tyrosine ammonia lyase activity similar to that of the polypeptide comprising an amino acid sequence set forth in SEQ ID NO: 1, 2 or 3 (e.g., SEQ ID NO: 1).

According to certain embodiment, a polypeptide according to ii) has tyrosine ammonia lyase activity similar to that of the polypeptide comprising the amino acid sequence set forth in SEQ ID NO: 1. According to certain other embodiments, a polypeptide according to ii) has tyrosine ammonia lyase activity similar to that of the polypeptide comprising the amino acid sequence set forth in SEQ ID NO: 2. According to certain other embodiments, a polypeptide according to ii) has tyrosine ammonia lyase activity similar to that of the polypeptide comprising the amino acid sequence set forth in SEQ ID NO: 3. With "similar" tyrosine ammonia lyase activity it is meant that the polypeptide according to ii) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 200%, at least about 400% or at least about 800%, of the ammonia lyase activity of the reference polypeptide (e.g., SEQ ID NO: 1).

The tyrosine ammonia lyase activity may for instance be determined in accordance to the following method: Enzymatic assays are performed in 200 µL volumes in wells in a UV transparent 96-well plate, by following the increase in absorbance at 315 nm (pHCA) using spectrophotometry or HPLC with UV detection. The reaction mixtures contain 2 µg of purified protein and are initiated by adding 1 mM tyrosine or 6 mM after equilibration to 30° C. The enzymatic activity is calculated as U/g, where U is defined as µmol substrate converted per minute. Negative controls contain no purified protein. Kinetic constants Km and vmax are determined from assays containing 1.56 µM to 200 µM tyrosine. See also Kyndt et al. (2002).

As determined in accordance with Example 2, the values for $K_m$ (µM), $k_{cat}$ (min$^{-1}$) and $k_{cat}/K_m$ (mM$^{-1}$ s$^{-1}$) for the tyrosine ammonia lyase derived from *Flavobacterium johnsoniae* (SEQ ID NO: 1) using tyrosine as substrate are 5.7, 1.27 and 3.71, respectively. Each of these kinetic parameters may serve as reference parameter to determine the tyrosine ammonia lyase activity of the polypeptide according to ii), however, $k_{cat}/K_m$ is preferred.

As determined in accordance with Example 2, the values for $K_m$ (µM), $k_{cat}$ (min$^{-1}$) and $k_{cat}/K_m$ (mM$^{-1}$ s$^{-1}$) for the tyrosine ammonia lyase derived from *Herpetosiphon aurantiacus* (SEQ ID NO: 2) using tyrosine as substrate are 16, 3.10 and 3.29, respectively. Each of these kinetic parameters may serve as reference parameter to determine the tyrosine ammonia lyase activity of the polypeptide according to ii), however, $k_{cat}/K_m$ is preferred.

According to certain embodiments, a polypeptide according to ii) shows tyrosine ammonia lyase activity expressed as $k_{cat}/K_m$ of at least about 3.2 mM$^{-1}$ s$^{-1}$, such as at least about 3.25 mM$^{-1}$ s, at least about 3.29 mM$^{-1}$ s$^{-1}$, at least about 3.5 mM$^{-1}$ s$^{-1}$, at least about 3.6 mM$^{-1}$ s$^{-1}$, at least about 3.65 mM$^{-1}$ s$^{-1}$ or at least about 3.7 mM$^{-1}$ s$^{-1}$.

According to certain embodiments, a polypeptide according to ii) has an affinity ($K_m$) towards phenylalanine of at least about 4000 µM, such as at least about 5000 µM, at least about 6000 µM or at least about 6500 µM.

For improved substrate specificity towards tyrosine, a polypeptide according to ii) preferably comprises the amino acid sequence set forth in SEQ ID NO: 4 or 5. The sequence LIRSHSSG (SEQ ID NO: 4) defines the region within the tyrosine ammonia lyase derived from *Flavobacterium johnsoniae* (SEQ ID NO: 1) conferring the substrate specificity towards tyrosine, whereas the sequence AIWYHKTG (SEQ ID NO: 5) defines the region within the tyrosine ammonia lyases derived from *Herpetosiphon aurantiacus* (SEQ ID NO: 2 or 3) conferring the substrate specificity towards tyrosine. Therefore, according to certain embodiments, a polypeptide according to ii) comprises the amino acid sequence set forth in SEQ ID NO: 4. According to certain other embodiments, a polypeptide according to ii) comprises the amino acid sequence set forth in SEQ ID NO: 5.

According to other certain embodiments, a polypeptide according to the invention is a polypeptide according to iii). Accordingly, a polypeptide according to the invention may be a polypeptide comprising an amino acid sequence set forth in SEQ ID NO: 1, 2 or 3 (e.g., SEQ ID NO: 1), wherein 1 or more, such as 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, 40 or more, 45 or more, 50 or more, 60 or more, 70 or more, 80 or more, 90 or more, 100 or more, 110 or more, 120 or more, 130 or more, 140 or more, or 150 or more, amino acid residues are substituted, deleted, and/or inserted. According to particular embodiments, a polypeptide according to iii) comprises an amino acid sequence set forth in SEQ ID NO: 1, 2 or 3 (e.g., SEQ ID NO: 1), wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to iii) comprises an amino acid sequence set forth in SEQ ID NO: 1, 2 or 3 (e.g., SEQ ID NO: 1), wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 1, 2 or 3 (e.g., SEQ ID NO: 1), wherein about 1 to about 30, such as about 1 to about 25, about 1 to about 20, about 1 to about 15, about 1 to about 10, about 1 to about 5, or about 1 to about 3, amino acid residues are substituted, deleted, and/or inserted. According to other more particular embodiments, a polypeptide according to iii) comprises an amino acid sequence set forth in SEQ ID NO: 1, 2 or 3 (e.g., SEQ ID NO: 1), wherein about 1 to about 25, such as about 1 to about 20, about 1 to about 15, about 1 to about 10, about 1 to about 5, or about 1 to about 3, amino acid residues are substituted, deleted and/or inserted.

According to particular embodiments, a polypeptide according to iii) comprises an amino acid sequence set forth in SEQ ID NO: 1, wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about to about 3, amino acid residues are substituted, deleted and/or inserted. According to more particular embodiments, a polypeptide according to iii) comprises an amino acid sequence set forth in SEQ ID NO: 1, wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 1, wherein about 1 to about 30, such as about 1 to about 25, about 1 to about 20, about 1 to about 15, about 1 to about 10, about 1 to about 5, or about 1 to about 3, amino acid residues are substituted, deleted, and/or inserted. According to other more particular embodiments, a polypeptide according to iii) comprises an amino acid sequence set forth in SEQ ID NO: 1, wherein about 1 to about 25, such as about 1 to about 20, about 1 to about 15, about 1 to about 10, about 1 to about 5, or about 1 to about 3, amino acid residues are substituted, deleted and/or inserted.

According to other particular embodiments, a polypeptide according to iii) comprises an amino acid sequence set forth in SEQ ID NO: 2, wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to iii) comprises an amino acid sequence set forth in SEQ ID NO: 2, wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 2, wherein about 1 to about 30, such as about 1 to about 25, about 1 to about 20, about 1 to about 15, about 1 to about 10, about 1 to about 5, or about 1 to about 3, amino acid residues are substituted, deleted, and/or inserted. According to other more particular embodiments, a polypeptide according to iii) comprises an amino acid sequence set forth in SEQ ID NO: 2, wherein about 1 to about 25, such as about 1 to about 20, about 1 to about 15, about 1 to about 10, about 1 to about 5, or about 1 to about 3, amino acid residues are substituted, deleted and/or inserted.

According to particular embodiments, a polypeptide according to iii) comprises an amino acid sequence set forth in SEQ ID NO: 3, wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to iii) comprises an amino acid sequence set forth in SEQ ID NO: 3, wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 3, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 3, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e. SEQ ID NO: 1, 2 or 3). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to iii) has tyrosine ammonia lyase activity. More preferably, a polypeptide according to iii) has a tyrosine ammonia lyase activity similar to that of the polypeptide comprising an amino acid sequence set forth in SEQ ID NO: 1, 2 or 3 (e.g., SEQ ID NO: 1). According to certain embodiment, a polypeptide according to iii) has tyrosine ammonia lyase activity similar to that of the polypeptide comprising the amino acid sequence set forth in SEQ ID NO: 1. According to certain other embodiments, a polypeptide according to iii) has tyrosine ammonia lyase activity similar to that of the polypeptide comprising the amino acid sequence set forth in SEQ ID NO: 2. According to certain other embodiments, a polypeptide according to iii) has tyrosine ammonia lyase activity similar to that of the polypeptide comprising the amino acid sequence set forth in SEQ ID NO: 3. With "similar" tyrosine ammonia lyase activity it is meant that the polypeptide according to iii) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 200%, at least about 400% or at least about 800%, of the ammonia lyase activity of the reference polypeptide (i.e. SEQ ID NO: 1, 2 or 3).

The tyrosine ammonia lyase activity may for instance be determined in accordance to the following method: Enzymatic assays are performed in 200 µL volumes in wells in a UV transparent 96-well plate, by following the increase in absorbance at 315 nm (pHCA) using spectrophotometry or HPLC with UV detection. The reaction mixtures contain 2 µg of purified protein and are initiated by adding 1 mM tyrosine or 6 mM after equilibration to 30° C. The enzymatic activity is calculated as U/g, where U is defined as µmol substrate converted per minute. Negative controls contain no purified protein. Kinetic constants $K_m$ and vmax are determined from assays containing 1.56 µM to 200 µM tyrosine. See also Kyndt et al. (2002).

As shown in Example 2, the values for $K_m$ (µM), $k_{cat}$ (min$^{-1}$) and $k_{cat}/K_m$ (mM$^{-1}$ s$^{-1}$) for the tyrosine ammonia lyase derived from *Flavobacterium johnsoniae* (SEQ ID NO: 1) using tyrosine as substrate are 5.7, 1.27 and 3.71, respectively. Each of these kinetic parameters may serve as reference parameter to determine the tyrosine ammonia lyase activity of the polypeptide according to iii), however, $k_{cat}/K_m$ is preferred.

As shown in Example 2, the values for $K_m$ (µM), $k_{cat}$ (min$^{-1}$) and $k_{cat}/K_m$ (mM$^{-1}$ s$^{-1}$) for the tyrosine ammonia lyase derived from *Herpetosiphon aurantiacus* (SEQ ID NO: 2) using tyrosine as substrate are 16, 3.10 and 3.29, respectively. Each of these kinetic parameters may serve as reference parameter to determine the tyrosine ammonia lyase activity of the polypeptide according to iii), however, $k_{cat}/K_m$ is preferred.

According to certain embodiments, a polypeptide according to iii) shows tyrosine ammonia lyase activity expressed as $k_{cat}/K_m$ of at least about 3.2 mM$^{-1}$ s$^{-1}$, such as at least about 3.25 mM$^{-1}$ s$^{-1}$, at least about 3.29 mM$^{-1}$ s$^{-1}$, at least about 3.5 mM$^{-1}$ s$^{-1}$, at least about 3.6 mM$^{-1}$ s$^{-1}$, at least about 3.65 mM$^{-1}$ s$^{-1}$ or at least about 3.7 mM$^{-1}$ s$^{-1}$.

According to certain embodiments, a polypeptide according to iii) has an affinity ($K_m$) towards phenylalanine of at least about 4000 µM, such as at least about 5000 µM, at least about 6000 µM or at least about 6500 µM.

For improved substrate specificity towards tyrosine, a polypeptide according to iii) preferably comprises the amino acid sequence set forth in SEQ ID NO: 4 or 5. The sequence LIRSHSSG (SEQ ID NO: 4) defines the region within the tyrosine ammonia lyase derived from *Flavobacterium johnsoniae* (SEQ ID NO: 1) conferring the substrate specificity towards tyrosine, whereas the sequence AIWYHKTG (SEQ ID NO: 5) defines the region within the tyrosine ammonia lyase derived from *Herpetosiphon aurantiacus* (SEQ ID NO: 2 or 3) conferring the substrate specificity towards tyrosine. Therefore, according to certain embodiments, a polypeptide according to iii) comprises the amino acid sequence set forth in SEQ ID NO: 4. According to certain other embodiments, a polypeptide according to iii) comprises the amino acid sequence set forth in SEQ ID NO: 5.

The polypeptide may be employed in accordance with the invention in isolated form, such as in purified form. The polypeptide may for instance be expressed by a recombinant host cell, and then purified. Techniques and means for the purification of polypeptides produced by a recombinant host cell are well know in the art. For example, in order to facilitate purification, an amino acid motif comprising several histidine residues, such as at least 6, may be inserted at the C- or N-terminal end of the polypeptide. A non-limiting example of such amino acid motif is provided in SEQ ID NO: 11. Various purification kits for histidine-tagged polypeptides are available from commercial sources such as Qiagen, Hilden, Germany; Clontech, Mountain View, Calif., USA; Bio-Rad, Hercules, Calif., USA and others.

Alternatively, The polypeptide may be chemically synthezised. Techniques for chemical peptide synthesis are well know and include Liquid-phase synthesis and Solid-phase synthesis.

The polypeptide can also be employed in accordance with the invention as part of a recombinant host cell. Such recombinant host cells are described in more details below.

It is understood that the details given herein with respect to a polypeptide apply to all aspects of the invention.

The present invention also provides a recombinant host cell comprising (e.g. expressing) a polypeptide as detailed herein. Generally, the polypeptide according to the invention will be heterologous to the host cell, which means that the polypeptide is normally not found in or made (i.e. expressed) by the host cell, but derived from a different species. Therefore, the present invention provides a recombinant host cell according to the present invention comprises a heterologous polypeptide selected from the group consisting of:

i) a polypeptide comprising an amino acid sequence set forth in SEQ ID NO: 1, 2 or 3 (e.g., SEQ ID NO: 1);

ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2 or 3 (e.g., SEQ ID NO: 1); or iii) a polypeptide comprising an amino acid sequence set forth in SEQ ID NO: 1, 2 or 3 (e.g., SEQ ID NO: 1), wherein 1 or more, such as about 1 to about 50, about 1 to about 40, about 1 to about 35, 1 to 30, 1 to 25, 1 to 20, 1 to 15, 1 to 10, 1 to 5, 1 to 3, amino acid residues are substituted, deleted and/or inserted.

Recombinant host cells in accordance with the invention can be produced from any suitable host organism, including single-celled or multicellular microorganisms such as bacteria, yeast, fungi, algae and plant, and higher eukaryotic organisms including nematodes, insects, reptiles, birds, amphibians and mammals.

Bacterial host cells are selected from Gram-positive and Gram-negative bacteria. Non-limiting examples for Gram-negative bacterial host cells include species from the genera *Escherichia, Erwinia, Klebsiella* and *Citrobacter*. Non-limiting examples of Gram-positive bacterial host cells include species from the genera *Bacillus, Lactococcus, Lactobacillus, Clostridium, Corynebacterium, Streptomyces, Streptococcus*, and *Cellulomonas*.

According to certain embodiments, the recombinant host cell is a bacterium, which may be a bacterium of the genus *Bacillus, Lactococcus, Lactobacillus, Clostridium, Corynebacterium, Geobacillus, Streptococcus, Pseudomonas, Streptomyces, Escherichia, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus*, or *Yersinia*.

According to particular embodiments, the recombinant host cell is a bacterium of the genus *Bacillus*. Non-limiting examples of a bacteria of the genus *Bacillus* are *Bacillus subtitlis, Bacillus amyloliquefaciens, Bacillus licheniformis*, and *Bacillus mojavensis*. According to more particular embodiments, the recombinant host cell is *Bacillus subtitlis*. According to other more particular embodiments, the recombinant host cell is *Bacillus licheniformis*.

According to other particular embodiments, the recombinant host cell is a bacterium of the genus *Lactococcus*. A non-limiting example of a bacterium of the genus *Lactococcus* is *Lactococcus lactis*. According to more particular embodiments, the recombinant host cell is *Lactococcus lactis*.

According to other particular embodiments, the recombinant host cell is a bacterium of the genus *Corynebacterium*. A non-limiting example of a bacterium of the genus *Corynebacterium* is *Corynebacterium glutamicum*. According to more particular embodiments, the recombinant host cell is *Corynebacterium glutamicum*.

According to other particular embodiments, the recombinant host cell is a bacterium of the genus *Streptomyces*. A non-limiting examples of a bacterium of the genus *Streptomyces* are *Streptornyces lividans, Streptomyces coelicolor*, or *Streptomyces griseus*. According to more particular embodiments, the recombinant host cell is *Streptomyces lividans*. According to other more particular embodiments, the recombinant host cell is *Streptomyces coelicolor*. According to other more particular embodiments, the recombinant host cell is *Streptomyces griseus*.

According to other particular embodiments, the recombinant host cell is a bacterium of the genus *Pseudomonas*. A non-limiting example of a bacterium of the genus *Pseudomonas* is *Pseudomonas putida*. According to more particular embodiments, the recombinant host cell is *Pseudomonas putida*.

According to other particular embodiments, the recombinant host cell is a bacterium of the genus *Escherichia*. A non-limiting example of a bacterium of the genus *Escherichia* is *Escherichia coli*. According to more particular embodiments, the recombinant host cell is *Escherichia coli*.

Yeast host cells may be derived from e.g., *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to certain embodiments, the recombinant host cell is a yeast, which may be a yeast is of the genus *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to particular embodiments, the recombinant host cell is a yeast of the genus *Saccharomyces*. A non-limiting example of a yeast of the genus *Saccharomyces* is *Saccharomyces cerevisiae*. According to more particular embodiments, the recombinant host cell is *Saccharomyces cerevisiae*.

According to particular embodiments, the recombinant host cell is a yeast of the genus *Pichia*. Non-limiting example of a yeast of the genus *Pichia* are *Pichia pastoris* and *pichia* kudriavzevii. According to more particular embodiments, the recombinant host cell is *Pichia pastoris*. According to other more particular embodiments, the recombinant host cell is *pichia* kudriavzevii.

Fungi host cells may be derived from, e.g., *Aspergillus*.

According to certain embodiments, the recombinant host cell is a fungus, such as a fungi of the genus *Aspergillus*. Non-limiting examples of a fungus of the genus *Aspergillus* are *Aspergillus Oryzae, Aspergillus niger* or *Aspergillus awamsii*. According to more particular embodiments, the recombinant host cell is *Aspergillus Oryzae*. According to other more particular embodiments, the recombinant host cell is *Aspergillus niger*. According to other more particular embodiments, the recombinant host cell is *Aspergillus awamsii*.

Algae host cells may be derived from, e.g., *Chlamydomonas, Haematococcus, Phaedactylum, Volvox* or *Dunaliella*.

According to certain embodiments, the recombinant host cell is an alga, which may be an algae of the genus *Chlamydomonas, Haematococcus, Phaedactylum, Volvox* or *Dunaliella*.

According to particular embodiments, the recombinant host cell is an alga cell of the genus *Chlamydomonas*. A non-limiting example of an alga of the genus *Chlamydomonas* is *Chlamydomonas reinhardtii*.

According to particular embodiments, the recombinant host cell is an alga cell of the genus *Haematococcus*. A non-limiting example of an alga of the genus *Haematococcus* is *Haematococcus pluvialis*.

According to other particular embodiments, the recombinant host cell is an alga cell of the genus *Phaedactylum*. A non-limiting example of an alga of the genus *Phaedactylum* is *Phaedactylum tricornatum*.

A plant host cell may be derived from, e.g., soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

According to certain embodiments, the recombinant host cell is a plant cell, such as a plant cell selected from the group consisting of soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

Generally, a recombinant host cell according to the invention has been genetically modified to express a polypeptide as detailed herein, which means that an exogenous nucleic acid molecule, such as a DNA molecule, which comprises a nucleotide sequence encoding said polypeptide has been introduced in the host cell. Techniques for introducing exogenous nucleic acid molecule, such as a DNA molecule, into the various host cells are well-known to those of skill in the art, and include transformation (e.g., heat shock or natural transformation), transfection, conjugation, electroporation and microinjection.

Accordingly, a host cell according to the invention comprises an exogenous nucleic acid molecule comprising a nucleotide sequence encoding a polypeptide as detailed herein.

In order to facilitate expression of the polypeptide in the host cell, the exogenous nucleic acid molecule may comprise suitable regulatory elements such as a promoter that is functional in the host cell to cause the production of an mRNA molecule and that is operably linked to the nucleotide sequence encoding said polypeptide.

Promoters useful in accordance with the invention are any known promoters that are functional in a given host cell to cause the production of an mRNA molecule. Many such promoters are known to the skilled person. Such promoters include promoters normally associated with other genes, and/or promoters isolated from any bacteria, yeast, fungi, alga or plant cell. The use of promoters for protein expression is generally known to those of skill in the art of moleculer biology, for example, see Sambrook et al., Molecular cloning: A Laboratory Manual, Cold Spring Harbor Laboratory, Cold Spring Harbor, N.Y., 1989. The promoter employed may be inducible. The term "inducible" used in the context of a promoter means that the promoter only directs transcription of an operably linked nucleotide sequence if a stimulus is present, such as a change in temperature or the presence of a chemical substance ("chemical inducer"). As used herein, "chemical induction" according to the present invention refers to the physical application of a exogenous or endogenous substance (incl. macromolecules, e.g., proteins or nucleic acids) to a host cell. This has the effect of causing the target promoter present in the host cell to increase the rate of transcription. Alternatively, the promoter employed may be constitutive. The term "constitutive" used in the context of a promoter means that the promoter is capable of directing transcription of an operably linked nucleotide sequence in the absence of stimulus (such as heat shock, chemicals etc.).

Non-limiting examples of promoters functional in bacteria, such as *Bacillus subtilis, Lactococcus lactis* or *Escherichia coli*, include both constitutive and inducible promoters such as T7 promoter, the beta-lactamase and lactose promoter systems; alkaline phosphatase (phoA) promoter, a tryptophan (trp) promoter system, tetracycline promoter, lambda-phage promoter, ribosomal protein promoters; and hybrid promoters such as the tac promoter. Other bacterial and synthetic promoters are also suitable.

Non-limiting examples of promoters functional in yeast, such as *Saccharomyces cerevisiae*, include xylose promoter, GAL and GAL10 promoters, TEF promoter, and pgk1 promoter.

Non-limiting examples of promoters functional in fungi, such as *Aspergillus Oryzae* or *Aspergillus niger*, include promotors derived from the gene encoding *Aspergillus oryzae* TAKA amylase, *Aspergillus niger* neutral α-amylase, *Aspergillus niger* acid stable α-amylase, *Aspergillus niger* or *Aspergillus awamsii* glucoamylase (gluA), *Aspergillus niger* acetamidase, *Aspergillus oryzae* alkaline protease, *Aspergillus oryzae* triose phosphatase isomerase, *Rhizopus* meihei aspartic proteinase, and *Rhizopus* meiheilipase.

Non-limiting examples of promoters functional in alga, such as *Haematococcus pluvialis*, include the CaMV35S promoter, the SV40 promoter, and promoter of the *Chlamydomonas reinhardtii* RBCS2 gene and the promoter of the *Volvox carteri* ARS gene.

Non-limiting examples of promoters functional in plant cells include the *Lactuca sative* psbA promoter, the tabacco psbA promoter, the tobacco rrn16 PEP+NEP promoter, the CaMV 35S promoter, the 19S promoter, the tomato E8 promoter, the nos promoter, the Mac promoter, and the pet E promoter or the ACT1 promoter.

Besides a promoter, the exogenous nucleic acid molecule may further comprise at least one regulatory element selected from a 5' untranslated region (5'UTR) and 3' untranslated region (3' UTR). Many such 5' UTRs and 3' UTRs derived from prokaryotes and eukaryotes are well known to the skilled person. Such regulatory elements include 5' UTRs and 3' UTRs normally associated with other genes, and/or 5' UTRs and 3' UTRs isolated from any bacteria, yeast, fungi, alga or plant cell.

If the host cell is a prokaryotic organism, the 5' UTR usually contains a ribosome binding site (RBS), also known as the Shine Dalgarno sequence which is usually 3-10 base pairs upstream from the initiation codon. Meanwhile, if the host cell is an eukaryotic organism the 5' UTR usually contains the Kozak consensus sequence. An eukaryotic 5' UTR may also contain cis-acting regulatory elements.

The exogenous nucleic acid molecule may be a vector or part of a vector, such as an expression vector. Normally, such a vector remains extrachromosomal within the host cell which means that it is found outside of the nucleus or nucleoid region of the host cell.

It is also contemplated by the present invention that the exogenous nucleic acid molecule is stably integrated into the genome of the host cell. Means for stable integration into the genome of a host cell, e.g., by homologous recombination, are well known to the skilled person.

In order to prevent degradation of the hydroxycinnamic acids produced by a method of the present invention involving the use of recombinant host cells, a recombinant host cell, especially a recombinant bacterial host cell such as *Bacillus subtilis* or *Lactococcus lactis*, may further be genetically modified by inactivating a gene or gene cluster encoding a polypeptide having phenolic acid decarboxylase (PAD) activity. By "inactivating" or "inactivation of" a gene or gene cluster it is intended that the gene or cluster of interest (e.g. the gene cluster encoding a polypeptide having phenolic acid decarboxylase (PAD) activity) is not expressed in a functional protein form. Techniques for inactivating a gene or gene cluster are well-known to those of skill in the art, and include random mutagenesis, site specific mutagenesis, recombination, integration and others.

According to certain embodiments, the recombinant host cell does not express a polypeptide having phenolic acid decarboxylase (PAD) activity.

According to cartain embodiments, the recombinant host cell has been genetically modified to inactivate a gene or gene cluster encoding a polypeptide having phenolic acid decarboxylase (PAD) activity.

According to particular embodiments, the recombinant host cell is a bacterium of the genus *bacillus*, such as *bacillus subtiltis*, or *lactococcus*, such as *Lactococcus lactis*, which has been genetically modified to inactivate the padC (or padA) gene.

According to other particular embodiments, the recombinant host cell is a yeast of the genus *Saccharomyces*, such as

*Saccharomyces cerevisiae*, which has been genetically modified to inactivate the *padi* gene.

According to other certain embodiments, the recombinant host cell does not contain within its genome a gene or gene cluster encoding a polypeptide having phenolic acid decarboxylase (PAD) activity.

It is understood that the details given herein with respect to a recombinant host cell apply to other aspects of the invention, in particular to the methods and uses according to the invention, which are described in more detail below.

Methods and Uses

The present invention provides methods and uses for producing hydroxycinnamic acids. Particularly, a method for producing a hydroxycinnamic acid of general formula I

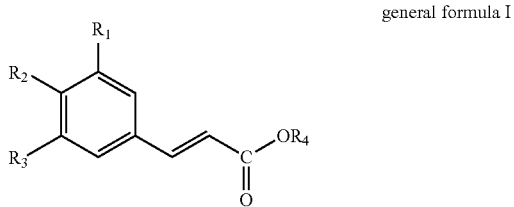

general formula I the method comprises deaminating a compound of general formula II

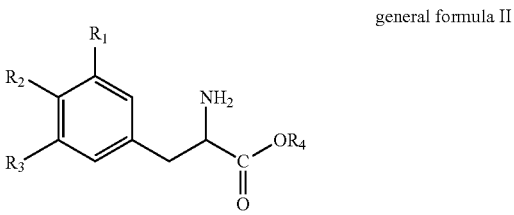

general formula II using a polypeptide as detailed herein, which may be selected from the group consisting of:
  i) a polypeptide comprising an amino acid sequence set forth in SEQ ID NO: 1, 2 or 3 (e.g., SEQ ID NO: 1);
  ii) a polypeptide comprising an amino acid sequence which has at least about 70%, such as at least about 75%, at least about 80%, at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3 (e.g. SEQ ID NO: 1); or
  iii) a polypeptide comprising an amino acid sequence set forth in SEQ ID NO: 1, 2 or 3 (e.g. SEQ ID NO: 1), wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted;
  wherein $R_1$, $R_2$ and $R_3$ independently are selected from the group consisting of hydrogen (H), hydroxyl (—OH), $C_{1-6}$-alkyl and $C_{1-6}$-Alkoxy, provided that at least one of $R_1$, $R_2$ and $R_3$ is hydroxyl (—OH); and $R_4$ is selected from the group consisting of hydrogen (—H) and $C_{1-6}$-alkyl.

"Deamination" or "deaminating" as used herein means that the amine group on the alpha carbon atom in the compound according to general formula II is removed.

Within the context of the present invention, $R_1$ may be hydrogen, hydroxyl, $C_{1-6}$-alkyl or $C_{1-6}$-Alkoxy. According to certain embodiments, $R_1$ is hydrogen. According to other certain embodiments, $R_1$ is hydroxyl. According to other certain embodiments, $R_1$ is $C_{1-6}$-alkyl, such as methyl or ethyl. According to other certain embodiments, $R_1$ is $C_{1-6}$-Alkoxy, such as methoxyl (—OCH$_3$).

Within the context of the present invention, $R_2$ may be hydrogen, hydroxyl, $C_{1-6}$-alkyl or $C_{1-6}$-Alkoxy. According to certain embodiments, $R_2$ is hydrogen. According to other certain embodiments, $R_2$ is hydroxyl. According to other certain embodiments, $R_2$ is $C_{1-6}$-alkyl, such as methyl or ethyl. According to other certain embodiments, $R_2$ is $C_{1-6}$-Alkoxy, such as methoxyl (—OCH$_3$).

Within the context of the present invention, $R_3$ may be hydrogen, hydroxyl, $C_{1-6}$-alkyl or $C_{1-6}$-Alkoxy. According to certain embodiments, $R_3$ is hydrogen. According to other certain embodiments, $R_3$ is hydroxyl. According to other certain embodiments, $R_3$ is $C_{1-6}$-alkyl, such as methyl or ethyl. According to other certain embodiments, $R_3$ is $C_{1-6}$-Alkoxy, such as methoxyl (—OCH$_3$).

Within the context of the present invention, $R_4$ may be hydrogen or $C_{1-6}$-alkyl. According to certain embodiments, $R_4$ is hydrogen. According to other certain embodiments, $R_4$ is $C_{1-6}$-alkyl, such as methyl (—CH$_3$) or ethyl (—CH$_2$CH$_3$).

According to particular embodiments, the method is for producing p-coumaric acid ($R_1$=H, $R_2$=OH, $R_3$=H, $R_4$=H), caffeic acid ($R_1$=H, $R_2$=OH, $R_3$=OH, $R_4$=H), ferulic acid ($R_1$=OCH$_3$, $R_2$=OH, $R_3$=H, $R_4$=H) or sinapic acid ($R_1$=OCH$_3$, $R_2$=OH, $R_3$=OCH$_3$, $R_4$=H). According to more particular embodiments, the method is for producing p-coumaric acid ($R_1$=H, $R_2$=OH, $R_3$=H, $R_4$=H). According to other more particular embodiments, the method is for producing of caffeic acid ($R_1$=H, $R_2$=OH, $R_3$=OH, $R_4$=H). According to other more particular embodiments, the method is for producing ferulic acid ($R_1$=OCH$_3$, $R_2$=OH, $R_3$=H, $R_4$=H). According to other more particular embodiments, the method is for producing sinapic acid ($R_1$=OCH$_3$, $R_2$=OH, $R_3$=OCH$_3$, $R_4$=H).

Suitable conditions for the deamination reaction are well known to the skilled person. Typically, the deamination reaction takes place at a temperature ranging from about 23 to about 60° C., such as from about 25 to about 40° C., such as at about 37° C. The deamination reaction may take place at a pH ranging from pH 4.0 to pH 14.0, such as from about pH 6 to about pH 11, or from about pH 7 to about pH 9.5, e.g. at pH 6.0, pH pH 7.0, pH. 7.5, pH 8.0, pH 8.5, pH 9.0, pH 9.5, pH 10.0, pH 10.5 or pH 11.0.

Moreover, the present invention provides a method for producing a hydroxcinnamic acid of general formula I as defined above, the method comprises the step of:
  a) contacting a recombinant host cell as detailed herein with a medium comprising a fermentable carbon substrate and/or a compound of the general formula II as defined above.

The medium employed may be any conventional medium suitable for culturing the host cell in question, and may be composed according to the principles of the prior art. The medium will usually contain all nutrients necessary for the growth and survival of the respective host cell, such as carbon and nitrogen sources and other inorganic salts. Suitable media, e.g. minimal or complex media, are available from commercial suppliers, or may be prepared according to published receipts, e.g. the American Type Culture Collection (ATCC) Catalogue of strains. Non-limiting standard medium well known to the skilled person include Luria Bertani (LB) broth, Sabouraud Dextrose (SD) broth, MS broth, Yeast Peptone Dextrose, BMMY, GMMY, or Yeast Malt Extract (YM) broth, which are all commercially available. A non-limiting example of suitable media for culturing bacterial cells, such as B. subtilis, L. lactis or E. coli cells, including minimal media and rich media such as Luria Broth (LB), M9 media, M17 media, SA media, MOPS media, Terrific Broth, YT and others. Suitable media for culturing eukaryotic cells, such as yeast cells, are RPMI 1640, MEM, DMEM, all of which may be supplemented with serum and/or growth factors as required by the particular host cell being cultured. The medium for culturing eukaryotic cells may also be any kind of minimal media such as Yeast minimal media.

The fermentable carbon substrate may be any suitable carbon substrate know in the art, and in particularly any carbon substrate commonly used in the cultivation of microorganisms and/or fermentation. Non-limiting examples of suitable fermentable carbon substates include carbohydrates (e.g., C5 sugars such as arabinose or xylose, or C6 sugars such as glucose), glycerol, glycerine, acetate, dihydroxyacetone, one-carbon source, methanol, methane, oils, animal fats, animal oils, plant oils, fatty acids, lipids, phospholipids, glycerolipids, monoglycerides, diglycerides, triglycerides, renewable carbon sources, polypeptides (e.g., a microbial or plant protein or peptide), yeast extract, component from a yeast extract, peptone, casaminoacids or any combination of two or more of the foregoing.

According to certain embodiments, the carbon substate is selected from the group consisting of C5 sugars (such as arabinose or xylose), C6 sugars (such as glucose or fructose), lactose, sucrose, glycerol, glycerine, acetate, yeast extract, component from a yeast extract, peptone, casaminoacids or combinations thereof.

According to certain embodiments, the medium comprises glucose.

According to certain other embodiments, the medium comprises glycerol.

According to certain other embodiments, the medium comprises acetate.

It is also contemplated to use starch as a carbon substrate. Depending on the microorganism used, the metabolization of starch may require the supplementation of beta-glucosidase, such as the beta-glucosidase from Neurospora crassa, to the medium. Alternatively, a recombination host cell according to the invention may be further genetically modified to express a beta-glucosidase, such as the beta-glucosidase from Neurospora crassa.

When a fermentable carbon substrate is employed it is thus possible that the recombinant host cell produces the hydroxycinnamic acid according to the invention directly from such primary carbon substrate.

Therefore, according to certain embodiments, the method for producing a hydroxcinnamic acid of general formula I as defined above comprises the step of:
  a) contacting a recombinant host cell as detailed herein with a medium comprising a fermentable carbon substrate.

According to certain other embodiments, the method for producing a hydroxcinnamic acid of general formula I as defined above comprises the step of:
  a) contacting a recombinant host cell as detailed herein with a medium comprising a compound of the general formula II as defined above.

According to certain other embodiments, the method for producing a hydroxcinnamic acid of general formula I as defined above comprises the step of:
  a) contacting a recombinant host cell as detailed herein with a medium comprising a fermentable carbon substrate and a compound of the general formula II as defined above.

The addition of exogenous tyrosine to the medium has shown to increase the production yield of the hydroxcinnamic acid (notably p-coumaric acid). See Table 4 below.

The method may further comprise step b) culturing the recombinant host cell under suitable conditions for the production of the hydroxcinnamic acid.

Suitable conditions for culturing the respective host cell are well known to the skilled person. Typically, the recombinant host cell is cultured at a temperature ranging from about 23 to about 60° C., such as from about 25 to about 40° C., such as at about 37° C. The pH of the medium may range from pH 4.0 to pH 14.0, such as from about pH 6 to about pH 11, or from about pH 7 to about pH 9.5, e.g. at pH 6.0, pH pH 7.0, pH. 7.5, pH 8.0, pH 8.5, pH 9.0, pH 9.5, pH 10.0, pH 10.5 or pH 11.0.

The method may further comprise step c) recovering the hydroxcinnamic acid. The hydroxcinnamic acid may be recovered by conventional method for isolation and purification chemical compounds from a medium. Well-known purification procedures include centrifugation or filtration, precipitation, and chromatographic methods such as e.g. ion exchange chromatography, gel filtration chromatography, etc.

The present invention further provides the use of a polypeptide as detailed herein in the production of a hydroxycinnamic acid, and particularly in the production of a hydroxycinnamic acid is of the general formula I. According to more particular embodiments, the present invention provides the use a polypeptide as detailed herein in the production of p-coumaric acid.

Certain Definitions

"Tyrosine ammonia lyase activity" as used herein refers to the ability of a polypeptide to catalysed the conversion of L-tyrosine into p-coumaric acid.

"Polypeptide," and "protein" are used interchangeably herein to denote a polymer of at least two amino acids covalently linked by an amide bond, regardless of length or post-transiational modification (e.g., glycosylation, phosphorylation, lipidation, myristilation, ubiquitination, etc.). Included within this definition are D- and L-amino acids, and mixtures of D- and L-amino acids.

"Nucleic acid" or "polynucleotide" are used interchangeably herein to denote a polymer of at least two nucleic acid monomer units or bases (e.g., adenine, cytosine, guanine, thymine) covalently linked by a phosphodiester bond, regardless of length or base modification.

"Recombinant" or "non-naturally occurring" when used with reference to, e.g., a host cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant host cells expressing genes that are not found within the native (non-recombinant) form of the cell or express native genes that are otherwise expressed at a different level.

"Substitution" or "substituted" refers to modification of the polypeptide by replacing one amino acid residue with another, for instance the replacement of an Arginine residue with a Glutamine residue in a polypeptide sequence is an amino acid substitution.

"Conservative substitution" refers to a substitution of an amino acid residue with a different residue having a similar side chain, and thus typically involves substitution of the amino acid in the polypeptide with amino acids within the same or similar class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having an aromatic side chain is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in a polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" or "deleted" refers to modification of the polypeptide by removal of one or more amino acids in the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide, in various embodiments, the deletion can comprise a continuous segment or can be discontinuous.

"Insertion" or "inserted" refers to modification of the polypeptide by addition of one or more amino acids to the reference polypeptide. Insertions can comprise addition of 1 or more amino acids, 2 or more amino acids, 5 or more amino acids, 10 or more amino acids, 15 or more amino acids, or 20 or more amino acids. Insertions can be in the internal portions of the polypeptide, or to the carboxy or amino terminus. The insertion can be a contiguous segment of amino acids or separated by one or more of the amino acids in the reference polypeptide.

"Host cell" as used herein refers to a living cell or microorganism that is capable of reproducing its genetic material and along with it recombinant genetic material that has been introduced into it—e.g., via heterologous transformation.

"Expression" includes any step involved in the production of a polypeptide (e.g., encoded enzyme) including, but not limited to, transcription, post-transcriptional modification, translation, post-translational modification, and secretion.

As used herein, "vector" refers to a nucleic acid molecule capable of transporting another nucleic acid molecule to which it has been linked. One type of vector is a "plasmid", which refers to a circular double stranded nucleic acid loop into which additional nucleic acid segments can be ligated. Certain vectors are capable of directing the expression of genes to which they are operatively linked. Such vectors are referred to herein as "expression vectors". Certain other vectors are capable of facilitating the insertion of a exogenous nucleic acid molecule into a genome of a host cell. Such vectors are referred to herein as "transformation vectors". In general, vectors of utility in recombinant nucleic acid techniques are often in the form of plasmids. In the present specification, "plasmid" and "vector" can be used interchangeably as the plasmid is the most commonly used form of a vector. Large numbers of suitable vectors are known to those of skill in the art and commercially available.

As used herein, "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. A "promoter functional in a host cell" refers to a "promoter" which is capable of supporting the initiation of transcription in said cell, causing the production of an mRNA molecule.

As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence. A promoter sequence is "operably-linked" to a gene when it is in sufficient proximity to the transcription start site of a gene to regulate transcription of the gene.

"Percentage of sequence identity," "% sequence identity" and "percent identity" are used herein to refer to comparisons between an amino acid sequence and a reference amino acid sequence. The "% sequence identify", as used herein, is calculated from the two amino acid sequences as follows: The sequences are aligned using Version 9 of the Genetic Computing Group's GAP (global alignment program), using the default BLOSUM62 matrix (see below) with a gap open penalty of −12 (for the first null of a gap) and a gap extension penalty of −4 (for each additional null in the gap). After alignment, percentage identity is calculated by expressing the number of matches as a percentage of the number of amino acids in the reference amino acid sequence.

The following BLOSUM62 matrix is used:

| Ala | 4 | | | | | |
|---|---|---|---|---|---|---|
| Arg | −1 | 5 | | | | |
| Asn | −2 | 0 | 6 | | | |
| Asp | −2 | −2 | 1 | 6 | | |
| Cys | 0 | −3 | −3 | −3 | 9 | |
| Gln | −1 | 1 | 0 | 0 | −3 | 5 |

| | Ala | Arg | Asn | Asp | Cys | Gln | Glu | Gly | His | Ile | Leu | Lys | Met | Phe | Pro | Ser | Thr | Trg | Tyr | Val |
|---|---|---|---|---|---|---|---|---|---|---|---|---|---|---|---|---|---|---|---|---|
| Gly | -1 | 0 | 0 | 2 | -4 | 2 | 5 | | | | | | | | | | | | | |
| Gly | 0 | -2 | 0 | -1 | -3 | -2 | -2 | 6 | | | | | | | | | | | | |
| His | -2 | 0 | 1 | -1 | -3 | 0 | 0 | -2 | 8 | | | | | | | | | | | |
| Ile | -1 | -3 | -3 | -3 | -1 | -3 | -3 | -4 | -3 | 4 | | | | | | | | | | |
| Leu | -1 | -2 | -3 | -4 | -1 | -2 | -3 | -4 | -3 | 2 | 4 | | | | | | | | | |
| Lys | -1 | 2 | 0 | -1 | -3 | 1 | 1 | -2 | -1 | -3 | -2 | 5 | | | | | | | | |
| Met | -1 | -1 | -2 | -3 | -1 | 0 | -2 | -3 | -2 | 1 | 2 | -1 | 5 | | | | | | | |
| Phe | -2 | -3 | -3 | -3 | -2 | -3 | -3 | -3 | -1 | 0 | 0 | -3 | 0 | 6 | | | | | | |
| Pro | -1 | -2 | -2 | -1 | -3 | -1 | -1 | -2 | -2 | -3 | -3 | -1 | -2 | -4 | 7 | | | | | |
| Ser | 1 | -1 | 1 | 0 | -1 | 0 | 0 | 0 | -1 | -2 | -2 | 0 | -1 | -2 | -1 | 4 | | | | |
| Thr | 0 | -1 | 0 | -1 | -1 | -1 | -1 | -2 | -2 | -1 | -1 | -1 | -1 | -2 | -1 | 1 | 5 | | | |
| Trp | -3 | -3 | -4 | -4 | -2 | -2 | -3 | -2 | -2 | -3 | -2 | -3 | -1 | 1 | -4 | -3 | -2 | 11 | | |
| Tyr | -2 | -2 | -2 | -3 | -2 | -1 | -2 | -3 | 2 | -1 | -1 | -2 | -1 | 3 | -3 | -2 | -2 | 2 | 7 | |
| Val | 0 | -3 | -3 | -3 | -1 | -2 | -2 | -3 | -3 | 3 | 1 | -2 | 1 | -1 | -2 | -2 | 0 | -3 | -1 | 4 |

"Reference sequence" or "reference amino acid sequence" refers to a defined sequence to which another sequence is compared. In the context of the present invention a reference amino acid sequence may be an amino acid sequence set forth in SEQ ID NO: 1, 2 or 3.

"Alkyl", "alkyl radical" or group as used herein means saturated, linear or branched hydrocarbons, which can be unsubstituted or mono- or polysubstituted. Thus, unsaturated alkyl is understood to encompass alkenyl and alkinyl groups, like e.g. —CH=CH—CH$_3$ or —C≡C—CH$_3$, while saturated alkyl encompasses e.g. —CH$_3$ and —CH$_2$—CH$_3$. "C$_{1-6}$-alkyl" includes C$_{1-2}$-alkyl, C$_{1-3}$-alkyl, C$_{1-4}$-alkyl, and C$_{1-5}$-alkyl, as well as C$_{2-3}$-alkyl, C$_{2-4}$-alkyl, C$_{2-5}$-alkyl, C$_{3-4}$-alkyl, C$_{3-5}$-alkyl, and C$_{4-5}$-alkyl. In these radicals, C$_{1-2}$-alkyl represents Cr or C$_2$-alkyl, C$_{1-3}$-alkyl represents C$_1$-, C$_2$- or C$_3$-alkyl, C$_{1-4}$-alkyl represents Cr, C$_2$-, C$_3$- or C$_4$-alkyl, C$_{1-5}$-alkyl represents C$_1$-, C$_2$-, C$_3$-, C$_4$-, or C$_5$-alkyl, C$_1$-alkyl represents Cr, C$_2$-, C$_3$-, C$_4$-, C$_5$- or C-alkyl. The alkyl radicals may be methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF$_2$, CF$_3$ or CH$_2$OH etc.

"Alkoxy", "alkoxy radical" or group as used herein means an "alkyl" singular bonded to oxygen. "C$_1$-alkoxy" includes C$_{1-2}$-alkoxy, C$_{1-3}$-alkoxy, C$_{1-4}$-alkoxy, and C$_{1-5}$-alkoxy, as well as C$_{2-3}$-alkoxy, C$_{2-4}$-alkoxy, C$_{2-5}$-alkoxy, C$_{3-4}$-alkoxy, C$_{3-5}$-alkoxy, and C$_{4-5}$-alkoxy. In these radicals, C$_{1-2}$-alkoxy represents C1- or C2-alkoxy, C$_{1-3}$-alkoxy represents C$_1$-, C$_2$- or C$_3$-alkoxy, C$_{1-4}$-alkyl represents C$_1$-, C$_2$-, C$_3$- or C$_4$-alkoxy, C$_{1-5}$-alkoxy represents C$_1$-, C$_2$-, C$_3$-, C4-, or C$_5$-alkoxy, C1-alkoxy represents C$_1$-, C$_2$-, C$_3$-, C$_4$-, C$_5$- or C$_6$-alkoxy. The alkoxy radicals may be methoxy, ethoxy, propoxy, butoxy, pentyloxy or hexyloxy.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

As demonstrated in the following examples, the polypeptides according to the invention show higher TAL activity compared to previously characterized enzymes, in particularly when expressed in a commonly used production yeast, as well as in selected industrially relevant bacteria. They are active in Gram-positive bacteria, Gram-negative bacteria as wells as in eukaryotic microorganisms. The improved activities have also been shown in in vitro biochemical assays.

As further demonstrated below, the polypeptides according to the invention have very specific TAL activity over PAL activity. The polypeptides according to the invention thus allow the enhanced biologically production of hydroxycinnamic acids such as pHCA. Furthermore, the production can be enhanced by the disruption of degradation pathways and the addition of tyrosine either extracellularly.

Example 1—Expression of TAL and PAL Enzymes in E. coli

A number of previously described and newly identified enzymes were expressed in the Gram negative bacterium E. coli for the comparison of enzymatic activities.

A number of genes encoding aromatic amino acid lyases were codon optimized using standard algorithms for expression in E. coli available by GeneArt (Life Technologies). The enzymes are listed in table 1. RsTAL, RmXAL, SeSam8, TcXAL, PcXAL, and RtXAL have previously been described. FjXAL, HaXAL1 and HaXAL2 have not been described before.

TABLE 1

Overview of enzymes

| Name | Organism | Protein GI | Len (aa) | SEQ ID NO |
|---|---|---|---|---|
| FjXAL | Flavobacterium johnsoniae | 146298870 | 506 | 1 |
| HaXAL1 | Herpetosiphon aurantiacus | 159898407 | 552 | 2 |
| HaXAL2 | Herpetosiphon aurantiacus | 159898927 | 552 | 3 |
| RsTAL | Rhodobacter sphaeroides | 126464011 | 523 | |
| RmXAL | Rhodotorula mucilaginosa/ Thodotorula rubra | 129592 | 713 | |
| SeSam8 | Saccharothrix espanaensis | 433607630 | 510 | |
| RtXAL | Rhodosporidium toruloides/ Rhodotorula glutinis | 129593 | 716 | |
| TcXAL | Trichosporon cutaneum | 77375521 | 689 | |
| PcXAL | Phanerochaete chrysosporium | 259279291 | 737 | |

Figure 2:
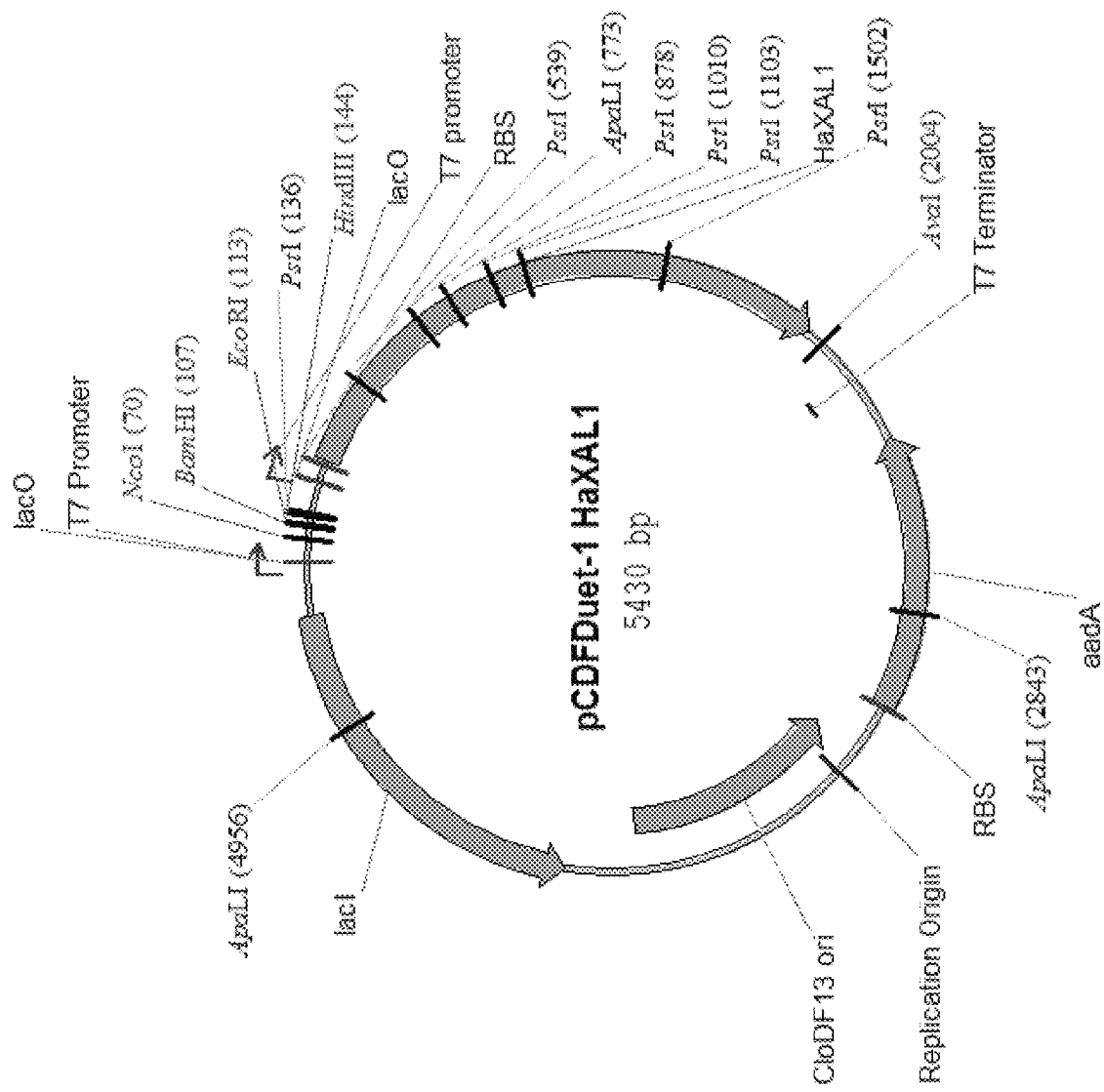
FIG. 2: Map of plasmid for expression of HaXAL1 in *E. coli*
Figure 3:
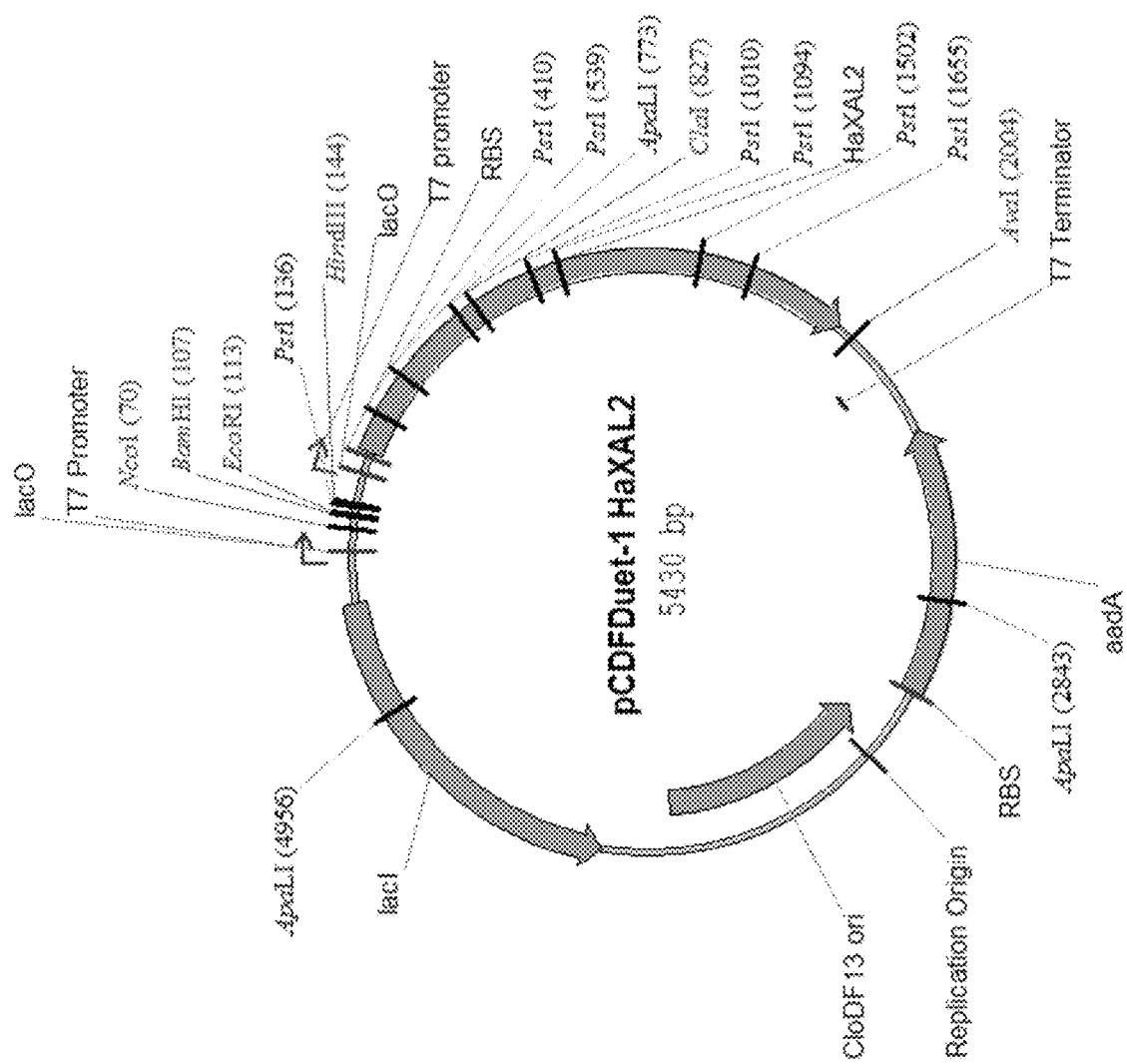
FIG. 3: Map of plasmid for expression of HaXAL2 in *E. coli*

Each of the genes were amplified by polymerase chain reaction (PCR) using the primers indicated in Table 6. The final PCR products were inserted inthe pCDFDuet-1 vector (Novagen/Life Technologies), which had been digested by NdeI and BgIII using Gibson reaction (New England Biolabs) (selected plasmids are shown in FIGS. 1 to 3).

Plasmids carrying the genes were transformed into electrocompetent E. coli BL21(DE3)pLysS cells (Life Technologies) and selected on LBplates containing 50 ug/mL streptomycin. The strains were grown in M9 minimal media containing glucose as a carbon source, and expression was induced by adding 1 mM IPTG at an optical density at 600 nm of 0.6. After three hours of growth at 30° C. the cultures were supplemented with 2 mM tyrosine, phenylalanine or histidine. After further 24 hours, samples were withdrawn for determination of the optical density at 600 nm and for the isolation of the supernatant.

The concentration of pHCA and CA in the supernatant was quantified by high performance (HPLC) and compared to chemical standards. HPLC was done on a Thermo setup using a HS-F5 column and mobile phases: 5 mM ammonium formate pH 4.0 (A) and acetonitrile (B) at 1.5 mL min-1, using a gradient elution starting at 5% B. From 0.5 min after injection to 7 min, the fraction of B increased linearly from 5% to 60%, and between 9.5 min and 9.6 min the fraction of B decreased back to 5%, and remaining there until 12m pHCA and CA were quantified by measuring absorbance at 333 nm and 277 nm, respectively. The production was tested without addition of precursors or the addition of either phenylalanine or tyrosine to the growth medium.

Table 2 shows the specific production of pHCA and CA in the various media. The specific production was calculated as micromolar (μM) concentration per unit of optical density of the culture at 600 nm, and standard deviations were calculated based on triplicate experiments. HaXAL1, HaXAL2 and FjXAL are the most specific enzymes and those that reach the highest yields.

Figure 4:
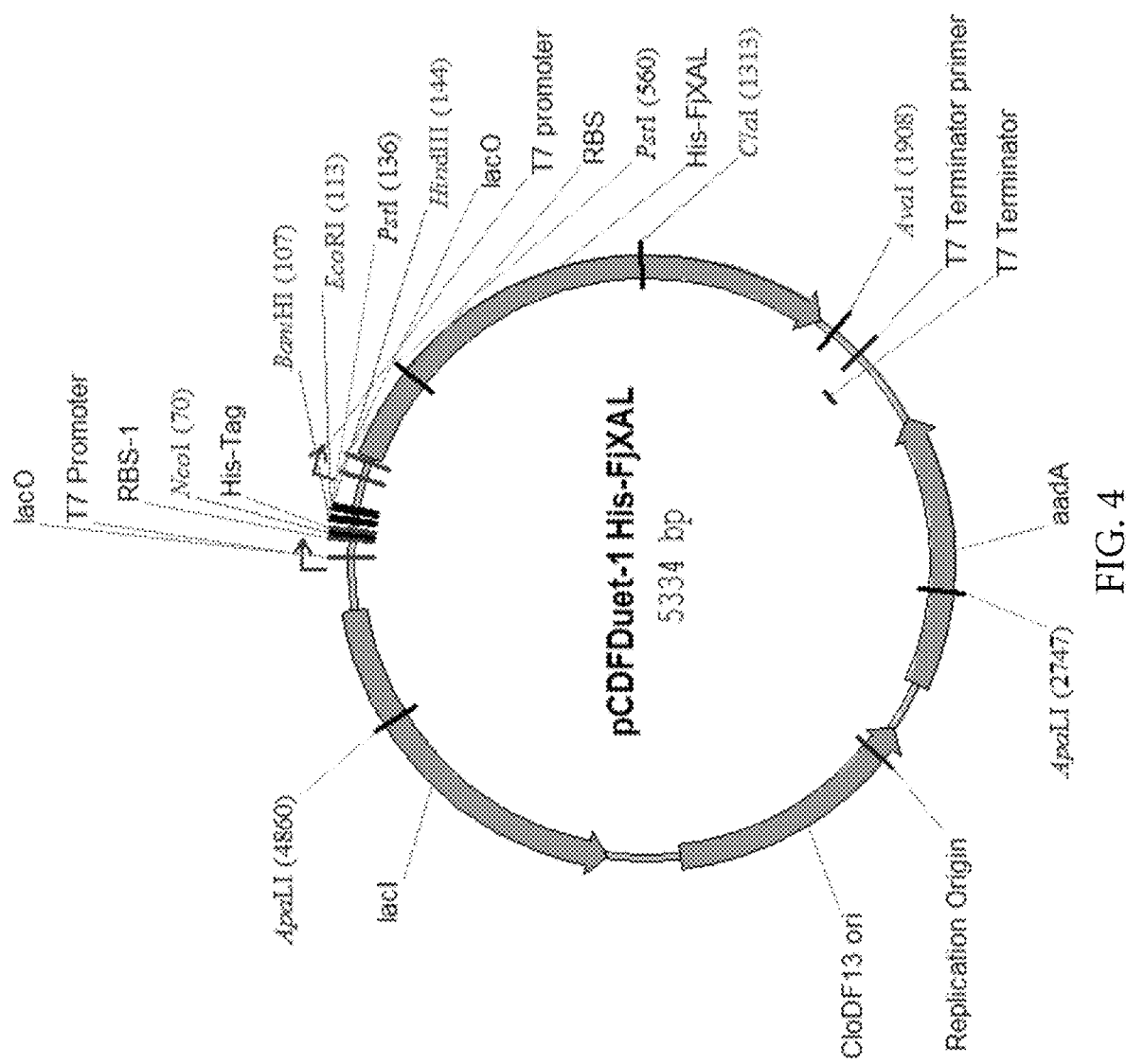
FIG. 4: Map of plasmid for expression of His-tagged FjXAL in *E. coli*
Figure 5:
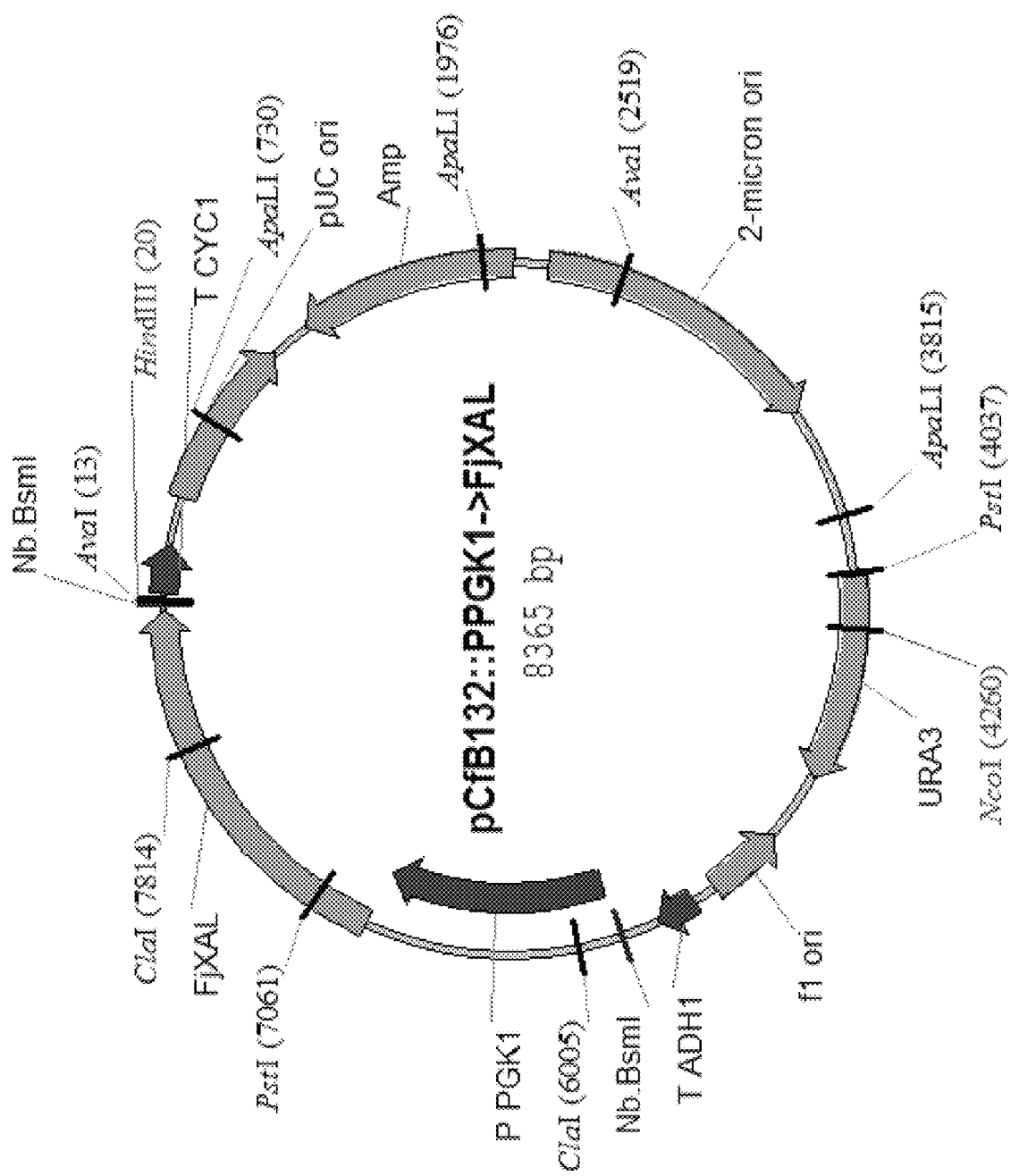
FIG. 5: Map of plasmid for expression of FjXAL in *S. cerevisiae*
Figure 6:
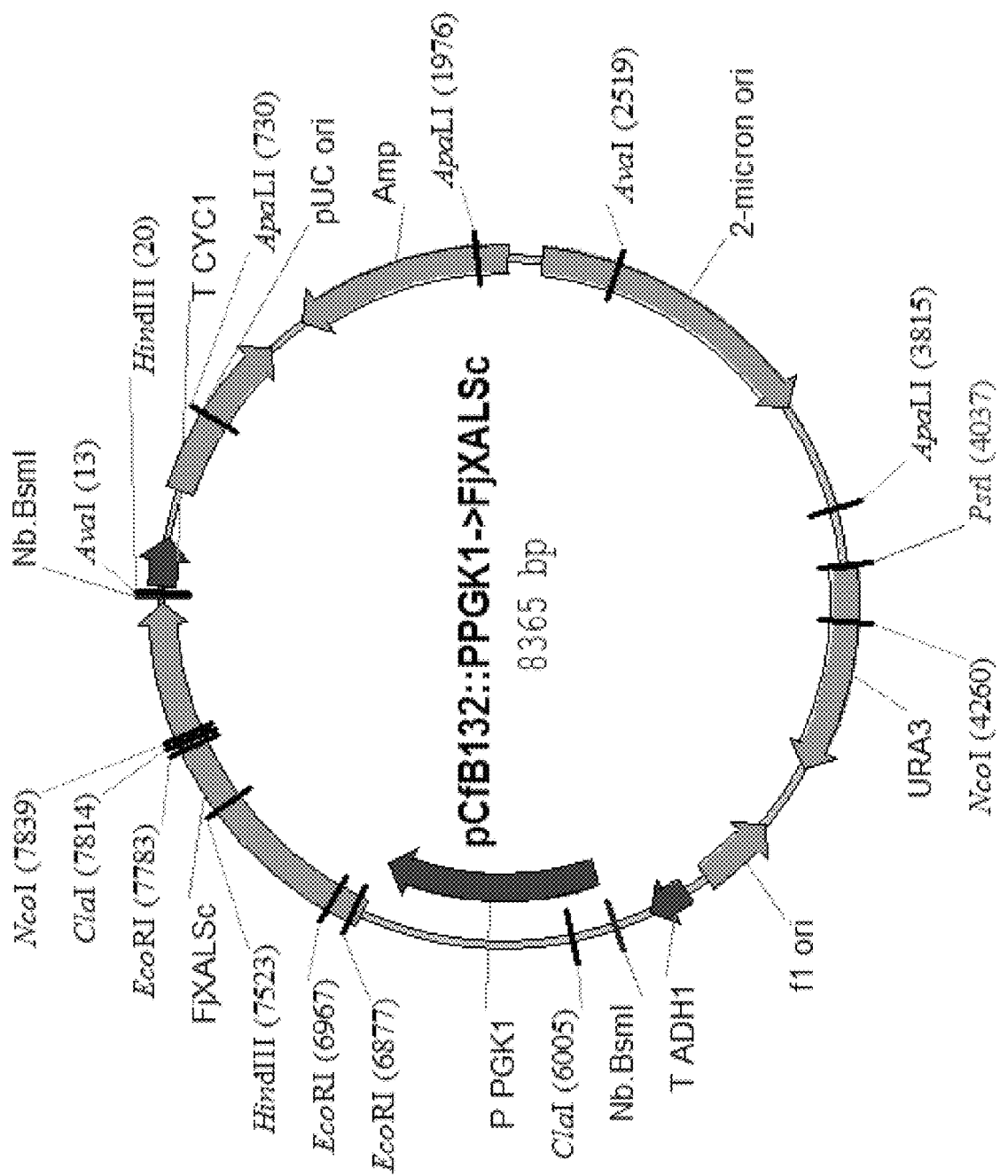
FIG. 6: Map of plasmid for expression of FjXAL in *S. cerevisiae*
Figure 7:
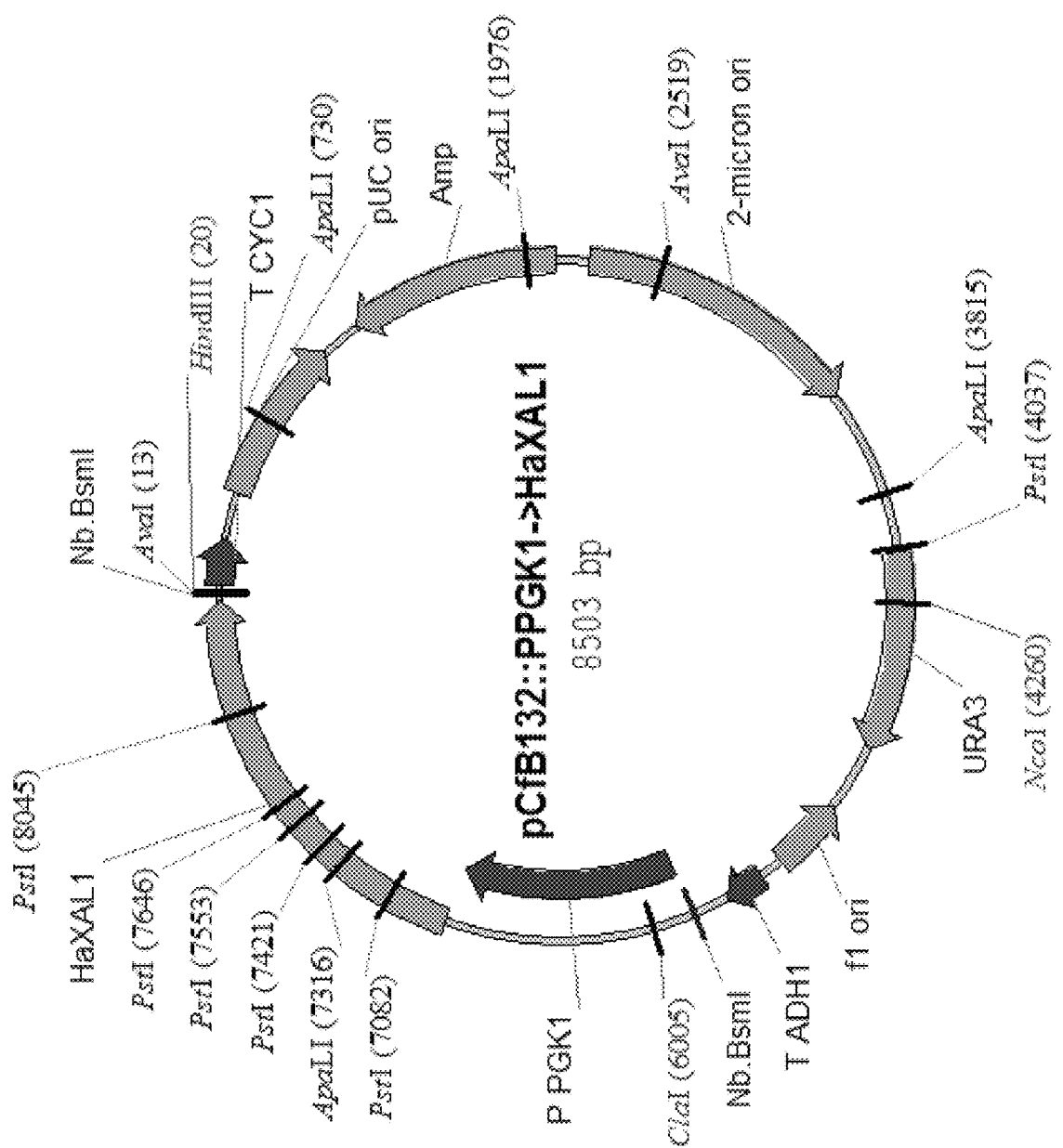
FIG. 7: Map of plasmid for expression of HaXAL1 in *S. cerevisiae*
Figure 8:
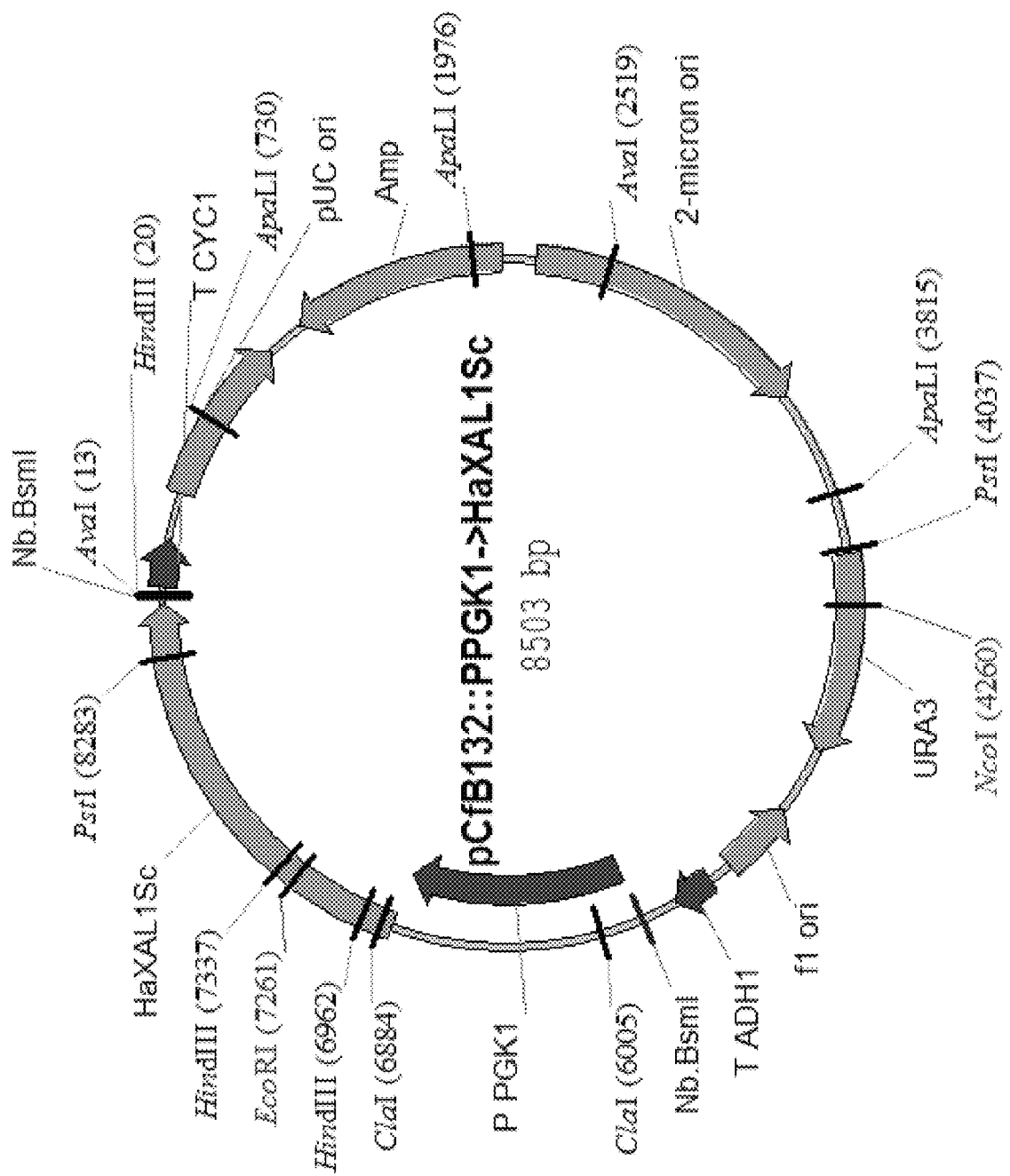
FIG. 8: Map of plasmid for expression of HaXAL1 in *S. cerevisiae*

FjXAL, FIG. 4) were transformed into electrocompetent *E. coli* BL21(DE3)pLysS cells (Life Technologies) and selected on LB plates containing 50 ug/mL streptomycin.

Strains expressing His-tagged versions of the enzymes were grown in LB media overnight at 37° C. and diluted into fresh LB media with 1 mM IPTG and growth was propagated overnight (approximately 18 h) at 30° C. Cells were harvested by centrifugation at 8000 rpm for 8 minutes, and disrupted by shearing into a buffer (50 mM Tris-HCl, 10 mM imidazole, 500 mM NaCl, 10% glycerol, pH 7.5). The homogenate was clarified by centrifugation at 10000 g for 10 min at 4° C., and the supernatant was loaded onto Ni2+-NTA resin column on an Äkta Pure system connected to a F9-C fraction collector (GE). Finally the fractions containing the purified polypeptide was dialyzed overnight against a buffer containing 50 mM Tris-HCl pH 7.5, 150 mM NaCl and 10% glycerol, flash-frozen in liquid nitrogen and stored at −80° C.

Enzymatic assays were performed in 200 μL volumes in wells in a UV transparent 96-well plate, by following the increase in absorbance at 315 nm (pHCA) or 295 nm (CA). The reaction mixtures contained 2 μg of purified protein and were initiated by adding 1 mM tyrosine or 6 mM after equilibration to 30° C. The enzymatic activity was calculated as U/g, where U is defined as μmol substrate converted per minute. No conversion was observed in the absence of enzymes under any conditions. Kinetic constants $K_m$ and vmax were determined from assays containing 1.56 μM to 200 μM tyrosine or 193 μM to 25 mM phenylalanine.

TABLE 2

Specific production of pHCA and CA in *Escherichia coli* (μM OD600-1 +/− standard deviation).

|  | M9 + Tyr pHCA | M9 + Tyr CA | M9 + Phe pHCA | M9 + Phe CA | M9 + His pHCA | M9 + His CA |
|---|---|---|---|---|---|---|
| No enzyme | 0 ± 0 | 0 ± 0 | 0 ± 0 | 0 ± 0 | 0 ± 0 | 0 ± 0 |
| RmXAL | 330 ± 9.7 | 30 ± 14 | 9.9 ± 0.3 | 450 ± 89 | 27 ± 3.8 | 35 ± 1 |
| TcXAL | 730 ± 23 | 11 ± 13 | 22 ± 0.8 | 510 ± 92 | | |
| PcXAL | 180 ± 21 | 2.8 ± 2.7 | 18 ± 4.9 | 170 ± 7.7 | | |
| RtXAL | 170 ± 10 | 5.9 ± 6.1 | 7.2 ± 1.3 | 180 ± 16 | | |
| RsTAL | 91 ± 13 | <0.05 | 24 ± 5 | 4.7 ± 0.4 | 26 ± 3 | 0 ± 0 |
| SeSam8 | 540 ± 50 | 0 ± 0 | 76 ± 6 | 18 ± 5.9 | 110 ± 26 | 0 ± 0 |
| FjXAL | 440 ± 100 | 0 ± 0 | 76 ± 29 | 0.5 ± 0.4 | 91 ± 20 | 0 ± 0 |
| HaXAL1 | 130 ± 26 | 0 ± 0 | 36 ± 14 | 1.1 ± 0.2 | | |
| HaXAL2 | 61 ± 9.7 | 0 ± 0 | 20 ± 4.4 | 0.4 ± 0.02 | | | pHCA may be formed from the natural metabolism of *E. coli*, but the production is enhanced by the addition of exogenous tyrosine.

Example 2—Enzymatic Characterization of Enzymes

Four of the enzymes were further purified by His-tag purification as follows. A DNA linker (5' phosphorylated oligonucleotides CBJP559 and CBJP560, Table 5) was inserted in place of the sequence between the NdeI and BgIII site in plasmid pCDFDuet-1. This would result in the addition of the amino acids MAHHHHHHENLYFQ (SEQ ID NO: 11) to the N-terminal end of the polypeptides. The resulting plasmid was amplified with primers CBJP575 and CBJP576 (table 5) and the genes were amplified and combined using the Gibson reaction (New England Biolabs). The PCR amplification used the same reverse primers as in example 1, but the forward primers matching the His-tag site of the linker (Table 5). Plasmids carrying the genes (e.g.

As table 3 shows, HaXAL1 and FjXAL had the highest catalytic efficiencies ($k_{cat}/K_m$ (mM−1 s−1)) towards tyrosine. They also had a very low affinity towards phenylalanine. The most specific enzyme was FjXAL.

TABLE 3

In vitro kinetics of selected TAL enzymes.

| Enzyme | Substrate | Km (μM) | Kcat (min−1) | Kcat/Km (mM−1 s−1) | TAL/PAL |
|---|---|---|---|---|---|
| RsTAL | Tyr | 5.6 | 10.4 | 3.10 | 125 |
| *Rhodobacter sphaeroides* | Phe | 2400 | 3.58 | 0.0246 | |
| SeSam8 | Tyr | 4.8 | 0.84 | 2.93 | 730 |
| *Saccharothrix espanaensis* | Phe | 2200 | 0.53 | 0.00403 | |
| HaXAL1 | Tyr | 16 | 3.10 | 3.29 | 540 |
| *Herpetosiphon aurantiacus* | Phe | 22000 | 7.68 | 0.00610 | |

TABLE 3-continued

In vitro kinetics of selected TAL enzymes.

| Enzyme | Substrate | Km (µM) | Kcat (min−1) | Kcat/Km (mM−1 s−1) | TAL/PAL |
|---|---|---|---|---|---|
| FjXAL | Tyr | 5.7 | 1.27 | 3.71 | 3000 |
| Flavobacterium johnsoniae | Phe | 6600 | 0.49 | 0.00123 | |

Example 3—Expression of TAL Enzymes in *S. Cerevisiae*

A number of the previously characterized enzymes were characterized when expressed in *Saccharomyces cerevisiae*. Genes encoding HaXAL1 and FjXAL were synthesized with codon optimization for *S. cerevisiae* available by GeneArt (Life Technologies), and were named HaXAL1 Sc and FjXALSc. Genes were amplified using the oligonucleotide (refer to specific name) shown in Table 6, and inserted by uracil-excision into the vector pCfB132 together with the PPGK1 promoter amplified by primers PPGK1_fw and PPGK1_rv (Jensen et al., 2014). The finished plasmids were transformed into *Saccharomyces cerevisiae* CEN.PK102-5B (MAT a ura3-52 his3Δ1 leu2-3/112 MAL2-8c SUC2) using a standard lithium acetate transformation protocol and selected for on synthetic drop-out media plates lacking uracil.

Cells were grown in SC medium without uracil, and diluted into Delft medium or Feed-In-Time (FIT) medium (m2p-labs) supplemented with leucine and histidine. 10 mM tyrosine was added to some cultures as indicated in Table 4. After 72 h of incubation at 30° C. with shaking, samples were taken for the analysis of optical density at 600 nm and for clarification of the supernatant, which was analyzed by HPLC as described in example 1. The specific production was calculated as micromolar (µM) concentration per unit of optical density of the culture at 600 nm and is shown in Table 4.

It was evident that HaXAL and FjXAl are the superior enzymes for catalyzing the TAL reaction, while not having background PAL reaction, even when tyrosine is added exogenously.

As demonstrated in Table 4, pHCA may be formed from the natural metabolism of *S. cerevisiae*, but the production may be enhanced by the addition of exogenous tyrosine.

TABLE 4

Specific production of pHCA and CA in *Saccharomyces cerevisiae* (µM OD600-1 +/− standard deviation).

| Enzyme | Delft | | Delft + Tyr | | FIT | | FIT + Tyr | |
|---|---|---|---|---|---|---|---|---|
| | pHCA | CA | pHCA | CA | pHCA | CA | pHCA | CA |
| PcXAL | 46 ± 5.1 | 17 ± 4.5 | 200 ± 29 | 16 ± 5.8 | 150 ± 65 | 75 ± 24 | 200 ± 37 | 32 ± 14 |
| RtXAL | 20 ± 0.8 | 18 ± 0.9 | 89 ± 13 | 21 ± 1.9 | 67 ± 4.3 | 88 ± 2 | 110 ± 8.8 | 57 ± 4.1 |
| SeSam8 | 3.1 ± 0.2 | 0 ± 0 | 6.9 ± 0.8 | 0 ± 0 | 17 ± 1.9 | 0 ± 0 | 5.6 ± 1.3 | 0 ± 0 |
| HaXAL1 | 31 ± 3.2 | 0 ± 0 | 110 ± 15 | 0 ± 0 | 140 ± 13 | 0 ± 0 | 120 ± 10 | 0 ± 0 |
| HaXAL1 Sc | 33 ± 2.6 | 0 ± 0 | 140 ± 6.3 | 0 ± 0 | 92 ± 16 | 0 ± 0 | 160 ± 35 | 0 ± 0 |
| HaXAL2 | 22 ± 5.2 | 0 ± 0 | 20 ± 6.3 | 0 ± 0 | 30 ± 16 | 0 ± 0 | 26 ± 11 | 0 ± 0 |
| FjXAL | 30 ± 3.5 | 0 ± 0 | 120 ± 16 | 0 ± 0 | 130 ± 16 | 0 ± 0 | 120 ± 19 | 0 ± 0 |
| FjXALSc | 41 ± 1.6 | 0 ± 0 | 150 ± 18 | 0 ± 0 | 130 ± 9.7 | 0 ± 0 | 200 ± 18 | 0 ± 0 |

TABLE 5

Oligonucleotides used for amplification and synthetic double-stranded DNA

| Name | Target | Usage | direction |
|---|---|---|---|
| CBJP483 | RsTAL | Gibson assembly, Expression in *E. coli* | forward Gibson Duet vector MCS2 NdeI |
| CBJP484 | RsTAL | Gibson assembly, Expression in *E. coli* | reverse Gibson Duet vector MCS2 BglII |
| CBJP487 | RmXAL | Gibson assembly, Expression in *E. coli* | forward Gibson Duet vector MCS2 NdeI |
| CBJP488 | RmXAL | Gibson assembly, Expression in *E. coli* | reverse Gibson Duet vector MCS2 BglII |
| CBJP535 | SeSam8 | Gibson assembly, Expression in *E. coli* | forward Gibson Duet vector MCS2 NdeI |
| CBJP536 | SeSam8 | Gibson assembly, Expression in *E. coli* | reverse Gibson Duet vector MCS2 BglII |
| CBJP553 | HaXAL1 | Gibson assembly, Expression in *E. coli* | forward Gibson Duet vector MCS2 NdeI |
| CBJP554 | HAXAL1 | Gibson assembly, Expression in *E. coli* | reverse Gibson Duet vector MCS2 BglII |
| CBJP555 | FjXAL | Gibson assembly, Expression in *E. coli* | forward Gibson Duet vector MCS2 NdeI |
| CBJP556 | FjXAL | Gibson assembly, Expression in *E. coli* | reverse Gibson Duet vector MCS2 BglII |
| CBJP559 | Linker for His6 in NdeI + BglII | Restriction Ligation | forward |
| CBJP560 | Linker for His6 in NdeI + BglII | Restriction Ligation | reverse |

TABLE 5-continued

Oligonucleotides used for amplification and synthetic double-stranded DNA

| Name | Target | Usage | direction |
|---|---|---|---|
| CBJP561 | His-RsTAL | Gibson assembly, Expression in *E. coli* | forward Gibson Duet vector MCS2::His6 NdeI |
| CBJP564 | His-SeSam8 | Gibson assembly, Expression in *E. coli* | forward Gibson Duet vector MCS2::His6 NdeI |
| CBJP573 | His-HaXAL1 | Gibson assembly, Expression in *E. coli* | forward Gibson Duet vector MCS2::His6 NdeI |
| CBJP574 | His-FjXAL | Gibson assembly, Expression in *E. coli* | forward Gibson Duet vector MCS2::His6 NdeI |
| CBJP575 | pCDFDuet-1 | Gibson assembly, Expression in *E. coli* | Forward |
| CBJP576 | pCDFDuet-1 modified with His-tag linker | Gibson assembly, Expression in *E. coli* | Reverse |
| PPGK1_rv | PGK1 promoter | Uracil Excision, Expression in *S. cerevisiae* | PG2R |
| PPGK1_fw | PGK1 promoter | Uracil Excision, Expression in *S. cerevisiae* | PV2F |
| CBJP637 | SeSam8 | Uracil Excision, Expression in *S. cerevisiae* | GP2F |
| CBJP638 | SeSam8 | Uracil Excision, Expression in *S. cerevisiae* | GV2R |
| CBJP645 | HaXAL1 | Uracil Excision, Expression in *S. cerevisiae* | GP2F |
| CBJP646 | HaXAL1 | Uracil Excision, Expression in *S. cerevisiae* | GV2R |
| CBJP647 | FjXAL | Uracil Excision, Expression in *S. cerevisiae* | GP2F |
| CBJP648 | FjXAL | Uracil Excision, Expression in *S. cerevisiae* | GV2R |
| CBJP649 | HaXAL1Sc | Uracil Excision, Expression in *S. cerevisiae* | GP2F |
| CBJP650 | HaXAL1Sc | Uracil Excision, Expression in *S. cerevisiae* | GV2R |
| CBJP651 | FjXALSc | Uracil Excision, Expression in *S. cerevisiae* | GP2F |
| CBJP652 | FjXALSc | Uracil Excision, Expression in *S. cerevisiae* | GV2R |
| CBJP741 | RtXAL | Gibson assembly, Expression in *E. coli* | forward Gibson Duet vector MCS2 NdeI |
| CBJP742 | RtXAL | Gibson assembly, Expression in *E. coli* | reverse Gibson Duet vector MCS2 BglII |
| CBJP743 | TcXAL | Gibson assembly, Expression in *E. coli* | forward Gibson Duet vector MCS2 NdeI |
| CBJP744 | TcXAL | Gibson assembly, Expression in *E. coli* | reverse Gibson Duet vector MCS2 BglII |
| CBJP752 | HaXAL2 | Gibson assembly, Expression in *E. coli* | forward Gibson Duet vector MCS2 NdeI |
| CBJP753 | HaXAL2 | Gibson assembly, Expression in *E. coli* | reverse Gibson Duet vector MCS2 BglII |
| CBJP754 | RtXAL | Uracil Excision, Expression in *S. cerevisiae* | GP2F |
| CBJP755 | RtXAL | Uracil Excision, Expression in *S. cerevisiae* | GV2R |
| CBJP762 | HaXAL2 | Uracil Excision, Expression in *S. cerevisiae* | GP2F |
| CBJP763 | HaXAL2 | Uracil Excision, Expression in *S. cerevisiae* | GV2R |

TABLE 5-continued

Oligonucleotides used for amplification and synthetic double-stranded DNA

| Name | Target | Usage | direction |
|---|---|---|---|
| CBJP812 | PcXAL | Gibson assembly, Expression in E. coli | forward Gibson Duet vector MCS2 NdeI |
| CBJP813 | PcXAL | Gibson assembly, Expression in E. coli | reverse Gibson Duet vector MCS2 BglII |
| CBJP815 | PcXAL | Uracil Excision, Expression in S. cerevisiae | forward |
| CBJP816 | PcXAL | Uracil Excision, Expression in S. cerevisiae | reverse |

TABLE 6

Overview of primer pairs used in the Examples

| Name | For E. coli Example 1 | For His tag Example 2 | For S. cerevisiae Example 3 |
|---|---|---|---|
| FjXAL | CBJP555 | CBJP574 | CBJP647 |
|  | CBJP556 | CBJP556 | CBJP648 |
| HaXAL1 | CBJP553 | CBJP573 | CBJP645 |
|  | CBJP554 | CBJP554 | CBJP646 |
| HaXAL2 | CBJP752 | — | CBJP762 |
|  | CBJP753 |  | CBJP763 |
| RsTAL | CBJP483 | CBJP561 | — |
|  | CBJP484 | CBJP484 |  |
| RmXAL | CBJP487 | — | — |
|  | CBJP488 |  |  |
| SeSam8 | CBJP535 | CBJP564 | CBJP637 |
|  | CBJP536 | CBJP536 | CBJP638 |
| RtXAL | CBJP741 | — | CBJP754 |
|  | CBJP742 |  | CBJP755 |
| TcXAL | CBJP743 | — | — |
|  | CBJP744 |  |  |
| PcXAL | CBJP812 | — | CBJP815 |
|  | CBJP813 |  | CBJP816 |
| HaXAL1Sc | — | — | CBJP649 |
|  |  |  | CBJP650 |
| FjXALSc | — | — | CBJP651 |
|  |  |  | CBJP652 |

Example 4—Expression of TAL Enzymes in Lactococcus lactis

We have shown that selected TAL enzymes leads to production of p-coumaric acid when expressed in L. lactis.

The synthetic RsXA$_{LI}$ (protein GI 129592) and RmXA$_{LI}$ (protein GI 126464011) genes, codon optimized for Lactococcus lactis (GeneArt), were cloned into the nisin inducible expression vector pNZ8048 (Kuipers et al., 1998) as follows: RsXA$_{LI}$ (SEQ ID NO: 56) and RmXA$_{LI}$ (SEQ ID NO: 57) genes and the vector were PCR amplified using the primers listed in Table 7, and were assembled in a single-tube isothermal reaction using the Gibson Assembly Master Mix (New England Biolabs). Reaction products were ethanol-precipitated and suspended in double distilled water before transformation into L. lactis by electroporation as described by Holo and Nes (1995). The synthetic genes encoding SeSam8, R_XAL, HaXAL1 and FjXAL described in a previous example above were amplified by PCR using the primer pairs listed in Table 1, digested with specific restriction enzymes, and cloned in-between the NcoI and XbaI restriction sites of pNZ8048. The plasmids were obtained and maintained in L. lactis NZ9000 (Kuipers et al., 1998) and the gene sequences of the different constructs were verified by sequencing.

To assess pHCA production, TAL-expression vectors were transformed into a strain derived from NZ9000, but with deletion of the genes ldh and dhB (NZ9000ΔldhΔldhB). A control strain was also constructed by transformation of NZ9000ΔldhΔldhB with empty expression vector pNZ8048.

For molecular biology procedures, L. lactis strains were cultivated as batch cultures (flasks) without aeration in M17 medium (Difco™, USA) supplemented with 0.5% glucose (w/v) at 30° C. To assess pHCA production, strains were grown as static cultures in chemically defined medium (CDM; Poolman and Konings, 1988) containing 1% glucose (wt/vol) without pH control (initial pH 6.5 or 7.0) and supplemented with 1.7 or 3.7 mM L-tyrosine. Plasmid selection was achieved by addition of 5 μg mL$^{-1}$ chloramphenicol to the growth medium. Growth was monitored by measuring OD$_{600}$. For heterologous expression of cloned tyrosine ammonia lyases, L. lactis strains were grown in CDM and nisin (1.5 μg L$^{-1}$) was added at an OD$_{600}$ of 0.3-0.4. Samples (1 mL) of cultures were collected at different points during growth; centrifuged (16,100×g, 10 min, 4° C.) and the supernatants stored at −20° C. until analysis by HPLC as described in a previous example above.

Figure 9:
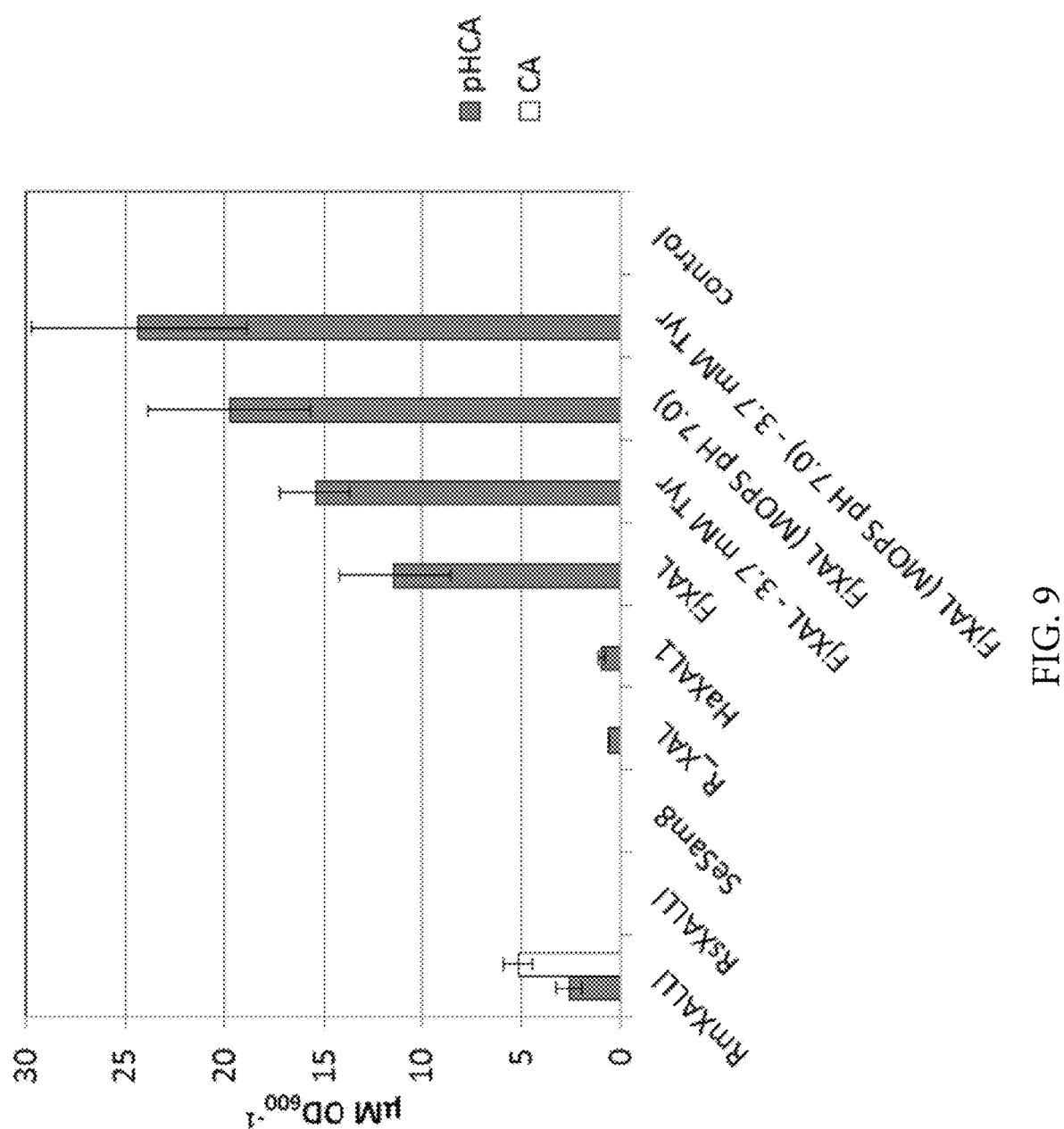
FIG. 9: Specific p-coumaric acid (pHCA) and cinnamic acid (CA) productivities of strains expressing TAL/PAL enzymes in CDM

FIG. 9 shows the specific p-coumaric acid (pHCA) and cinnamic acid (CA) productivities of strains expressing TAL/PAL enzymes in CDM. The first six columns are results from media containing 1.7 mM tyrosine. The seventh and ninth columns represent samples from strains grown in media containing 3.7 mM tyrosine, and the eighth and ninth columns are data from media with 68.5 mM 3-(N-morpholino)propanesulfonic acid (MOPS) and initial pH adjusted to 7.0 rather than 6.5. The strain carrying the empty plasmid ("control") did not result in production of either pHCA or CA under the examined conditions.

Even though the genes encoding RXA$_{LI}$ and RmXA$_{LI}$ had been specifically codon optimized for L. lactis, FjXAL showed by far the highest specific production of pHCA (15 μM OD$_{600}$$^{-1}$). This corresponds to a five-fold increase in specific production over RmXA$_{LI}$, the second-best enzyme. The productivities were lower than those achieved in E. coli, and the specific productivity of pHCA could be increased (24 μMD$_{600}$$^{-1}$) when the concentration of tyrosine in the media was increased (from 1.7 mM to 3.7 mM) and/or the pH of the medium was increased (from 6.5 to 7.0). RmXAL$_{LI}$ was the only enzyme resulting in production of CA.

Conclusively, the presented TAL enzymes result in specific production of pHCA when expressed in L. lactis. Furthermore, the production can be enhanced by manipulation of the supply of the precursor tyrosine and by manipulation of the pH of the growth medium.

TABLE 7

| Oligo-nucleotide | Gene | Direction | Sequence | Restriction site[a] |
|---|---|---|---|---|
| LL-Pnis_1 | | | GGTGAGTGCCTCCTTATAATTTATTTTG (SEQ ID NO: 58) | |
| LL-Pnis_2 | | | AAGCTTTCTTTGAACCAAAATTAGAAAACC (SEQ ID NO: 59) | |
| LL-RsXAL-Fw | RsTAL$_{LI}$ | Forward | CAAAATAAATTATAAGGAGGCACTCACCATGCTTGCTATGTCACCACCAAAACC (SEQ ID NO: 60) | |
| LL-RsXAL-Rv | RsTAL$_{LI}$ | Reverse | GGTTTTCTAATTTTGGTTCAAAGAAAGCTTTTAAACTGGTGATTGTTGTAATAAATG (SEQ ID NO: 61) | |
| LL-RmXAL-Fw | RmXAL$_{LI}$ | Forward | CAAAATAAATTATAAGGAGGCACTCACCATGGCTCCATCAGTTGATTCAATTGC (SEQ ID NO: 62) | |
| LL-RmXAL-Rv | RmXAL$_{LI}$ | Reverse | GGTTTTCTAATTTTGGTTCAAAGAAAGCTTTTAAGCCATCATTTTAACTAAAACTGG (SEQ ID NO: 63) | |
| LL-SeSam8-Fw | SeSam8 | Forward | CATG<u>TCATGA</u>CCCAGGTTGTTGAACG (SEQ ID NO: 64) | BspHI |
| LL-SeSam8-Rv | SeSam8 | Reverse | GC<u>TCTAGA</u>TTAGCCAAAATCTTTACCATC (SEQ ID NO: 65) | XbaI |
| LL-R_XAL-Fw | R_XAL | Forward | GC<u>GGTCTCCCATG</u>CGTAGCGAACAGCTGAC (SEQ ID NO: 66) | BsaI |
| LL-R_XAL-Rv | R_XAL | Reverse | GC<u>TCTAGA</u>TTAGGCCAGCAGTTCAATCAG (SEQ ID NO: 67) | XbaI |
| LL-HaXAL1-Fw | HaXAL1 | Forward | GC<u>GGTCTCCCATG</u>AGCACCACCCTGATTCTG (SEQ ID NO: 68) | BsaI |
| LL-HaXAL1-Rv | HaXAL1 | Reverse | GC<u>TCTAGA</u>TTAGCGAAACAGAATAATACTACG (SEQ ID NO: 69) | XbaI |
| LL-FjXAL-Fw | FjXAL | Forward | CATG<u>TCATGA</u>ACACCATCAACGAATATC (SEQ ID NO: 70) | BspHI |
| LL-FjXAL-Rv | FjXAL | Reverse | GC<u>TCTAGA</u>TTAATTGTTAATCAGGTGGTC (SEQ ID NO: 71) | XbaI |

[a]Underlined sequences indicate the respective restriction site.

Example 5—Production of p-Coumaric Acid in *Bacillus subtilis*

We have shown that expressing genes encoding tyrosine ammonia-lyases in *Bacillus subtilis* enables production of p-coumaric acid, and that the productivity is enhanced when the gene padC, encoding a phenolic acid decarboxylase, which is a p-coumaric acid degradative enzyme that results in the formation of 4-vinylphenol, is disrupted.

Genes encoding the tyrosine ammonia-lyases SeSam8 and FjXAL were expressed chromosomally in *Bacillus subtilis* as follows. Table 8 lists oligonucleotides used as primers in PCR reactions. A part ("pel end") of the pel gen, the region downstream, an erythromycin resistance gene and the constitutive promoter Pcons from *Bacillus subtilis* strain AN214 (U.S. Pat. No. 8,535,911) were PCR amplified using primers CBJP680 and CBJP666. Another part of pel and the region upstream was amplified using primers CBJP667 and CBJP682 ("pel front"). SeSam8 was amplified using primers CBJP689 and CBJP690 and FjXAL was amplified using primers CBJP691 and CBJP692. PCR fragments were combined using splicing by overhang extension PCR (SOE-PCR), with "pel end", "pel front" and either SeSam8 or FjXAL. The two resulting SOE-PCR products were individually integrated into a non-sporulating *Bacillus subtilis* 168 ΔspoIIΔC deletion strain (Novozymes, US 2011/0306139 A1), selecting for resistance to 5 μg mL$^{-1}$ erythromycin, resulting in strains CBJ1007 and CBJ1008.

The padC gene of these strains was furthermore disrupted (inactivated) by integration of a chloramphenicol resistance gene as follows. The chloramphenicol resistance gene of plasmid pC194 (Horinouchi and Weisblum, 1982) was amplified using primers CBJP835 and CBJP836. Regions surrounding padC was amplified using primer pair CBJP837/CBJP838 and CBJP839/CBJP840, respectively. The three fragments were purified from an agarose gel and combined by SOE-PCR. The SOE-PCR product was transformed into CBJ1007 and CBJ1008, and transformants were selected on LB agar plates with 0.2% glucose, 5 μg mL$^{-1}$ erythromycin and 3 μg mL$^{-1}$ chloramphenicol, resulting in strains CBJ1011 and CBJ1012.

To access the productivity, the strains 168 ΔspoIIAC, CBJ1007, CBJ1008, CBJ1011 and CBJ1012 were grown in various media. Colonies were used to inoculate growth tubes with 5 mL LB media with 5 μg mL$^{-1}$ erythromycin and 5 μg mL$^{-1}$ chloramphenicol, which were placed shaking at 250 rpm at 37° C. overnight before being removed. Samples were withdrawn for HPLC analysis as described in example 1. 10 μL of the cultures in LB media were used to inoculate growth tubes with 5 mL M9 media supplemented with 0.2% glucose and 50 mg L-tryptophan with or without 2 mM tyrosine. The tubes were aerated by shaking at 250 rpm at 37° C. overnight. Samples were withdrawn for HPLC analysis. p-coumaric acid was measured at 333 nm and 4-vinylphenol was measured at 277 nm.

Table 9 shows the productivity as μM pHCA and 4-vinylphenol formed per cell measured at the optical density at 600 nm in a 1-cm light path for three replicates of each experiment. It is evident that the background strain does not produce p-coumaric acid and that the productivity reached is higher for the strain expressing FjXAL than SeSam8. Furthermore the productivity is increased in the strains were padC is disrupted (inactivated).

TABLE 8

| Oligonucleotides used for PCR reactions | |
|---|---|
| CBJP666 | CATGTTTCCTCTCCCTCTCA TTTTC (SEQ ID NO: 72) |
| CBJP667 | TAAGGTAATAAAAAAACACC TCC (SEQ ID NO: 73) |
| CBJP680 | TCATACCATTTTTCACAGGG (SEQ ID NO: 74) |
| CBJP682 | GTCTCACTTCCTTACTGCGT (SEQ ID NO: 75) |
| CBJP689 | GAAAATGAGAGGGAGAGGAA ACATGACCCAGGTTGTTGAA CG (SEQ ID NO: 76) |
| CBJP690 | GGAGGTGTTTTTTTATTACC TTATCAGCCAAAATCTTTAC CATCTGC (SEQ ID NO: 77) |
| CBJP691 | GAAAATGAGAGGGAGAGGAA ACATGAACACCATCAACGAA TATCTG (SEQ ID NO: 78) |
| CBJP692 | GGAGGTGTTTTTTTATTACC TTATCAATTGTTAATCAGGT GGTCTTTTACTTTCTG (SEQ ID NO: 79) |
| CBJP835 | CCCGCGCGAATATCGTCTGT CCTTCTTCAACTAACGGGGC AG (SEQ ID NO: 80) |
| CBJP836 | GAAGTACAGTAAAAGACTAA GGTTATGTTACAGTAATATT GAC (SEQ ID NO: 81) |
| CBJP837 | GACGGTTAACTCTGTCACAA GCG (SEQ ID NO: 82) |
| CBJP838 | CCTTAGTCTTTTACTGTACT TC (SEQ ID NO: 83) |
| CBJP839 | CGGAATCCAATATAGAAGAA TGG (SEQ ID NO: 84) |
| CBJP840 | GACAGACGATATTCGCGCGG G (SEQ ID NO: 85) |

TABLE 9

Productivity of p-coumaric acid (pHCA) and 4-vinylphenol (4VP) in *Bacillus subtilis* strains grown in LB media and in M9 medium with 0.2% glucose (M9) or M9 with 2 mM tyrosine.

| | LB | | M9 | | M9 with tyrosine | |
|---|---|---|---|---|---|---|
| Genotype | pHCA | 4VP | pHCA | 4VP | pHCA | 4VP |
| ΔspoIIAC | 0 ± 0 | 0 ± 0 | 0 ± 0 | 0 ± 0 | 0 ± 0 | 0 ± 0 |
| ΔspoIIAC pel:SeSam8 | 8.7 ± 0.71 | 0 ± 0 | 0 ± 0 | 0.25 ± 0.021 | 0 ± 0 | 0 ± 0 |
| ΔspoIIAC pel:FjXAL | 170 ± 23 | 1400 ± 200 | 0 ± 0 | 65 ± 2.3 | 36 ± 11 | 380 ± 37 |
| ΔspoIIAC pel:SeSam8 ΔpadC | 13 ± 9.1 | 0 ± 0 | 0.37 ± 0.047 | 0 ± 0 | 2.3 ± 0.44 | 0 ± 0 |
| ΔspoIIAC pel:FjXAL ΔpadC | 1000 ± 380 | 0 ± 0 | 51 ± 11 | 0 ± 0 | 310 ± 26 | 0 ± 0 |

Conclusively, p-coumaric acid can be produced in *Bacillus subtilis* when expressing a gene encoding a tyrosine ammonia-lyase such as SeSam8 or FjXAL. FjXAL is more efficient in catalyzing this production than SeSam8. A disruption of the gene padC, and thereby a degradative pathway, furthermore enhances the productivity and eliminates 4-vinylphenol as a byproduct.

Example 6—Production of Hydroxycinnamic Acids Other than p-Coumaric Acid

TAL enzymes have activity toward several aromatic compounds beyond tyrosine. Specifically, we here show that the tyrosine derivatives L-dopa (3,4-dihydroxyphenylalanine or (2S)-2-Amino-3-(3,4-dihydroxyphenyl)propanoic acid) and 3-O-methyldopa (L-3-Methoxytyrosine or 2-Amino-3-(4-hydroxy-3-methoxyphenyl)propanoic acid) are deaminated to caffeic acid and ferulic acid, respectively, by cells expressing selected genes encoding TAL enzymes.

*E. coli* strains described in Example 1 were used. M9 medium with 0.2% glucose and 0.5 mM IPTG also containing either tyrosine (204 µM), L-dopa (194 µM) or 3-O-methyldopa (262 µM) was transferred as 3-mL aliquots into a 24-well deep-well plate (Enzyscreen). Aliquots were taken for HPLC before the wells were inoculated with 200 µL of overnight cultures of the strains. The plates were placed at 37° C. with shaking for 16 hours. Samples of the supernatant were withdrawn after two rounds of centrifugation. The samples were subjected to HPLC along with chemical standards as described in Example 1. p-coumaric acid, caffeic acid and ferulic acid was measured by absorbance at 333 nm. Tyrosine, L-dopa and 3-O-methyldopa were measured by fluorescence (excitation at 274 nm, emission at 303 nm).

Table 10 shows the concentrations measured from the culture supernatants from duplicate experiments. There was no measurable product in the medium before inoculation.

TABLE 10

Titers (µM) of p-coumaric acid, L-dopa and 3-O-methyldopa in supernatants of *E. coli* cultures expressing different TAL homologs. Cultures were grown in M9 medium with 0.2% glucose (M9) with different additions of substrates as indicated.

| | Medium | | |
| --- | --- | --- | --- |
| | M9 + tyrosine | M9 + L-dopa | M9 + 3-O-methyldopa |
| | Product | | |
| | p-coumaric acid | Caffeic acid | Ferulic acid |
| No Enzyme | 0 ± 0 | 0 ± 0 | 0 ± 0 |
| SeSam8 | 102 ± 7.8 | 5.3 ± 1.1 | 0.5 ± 0.2 |
| HaXAL1 | 81 ± 1.2 | 6.9 ± 1.3 | 0.6 ± 0.0 |
| FjXAL | 215 ± 11.1 | 5.7 ± 1.0 | 1.1 ± 0.3 |

Conclusively, the enzymes HaXAL1 and FjXAL not only catalyze the deamination of tyrosine, but also catalyze the deamination of derivatives thereof. As an example hereof, the enzymes HaXAL1 and FjXAL are shown to use L-dopa and 3-O-methydopa, which for these particular substrates result in the formation of caffeic acid and ferulic acid. Thus, these enzymes may be used to produce hydroxycinnamic acids using tyrosine or derivatives thereof as substrate.

LIST OF REFERENCES CITED IN THE DESCRIPTION

Appert C., Logemann E., Hahlbrock K., Schmid J., and Amrhein N. (1994) Structural and catalytic properties of the four phenylalanine ammonia-lyase isoenzymes from parsley (petroselinum crispum nym.). *Eur J Biochem* 225: 491-499.

Bartsch S., and Bornscheuer U. T. (2009) A single residue influences the reaction mechanism of ammonia lyases and mutases. *Angew Chem Int Ed Engl* 48: 3362-3365.

Bartsch S., Wybenga G. G., Jansen M., Heberling M. M., Wu B., Dijkstra B. W., and Janssen D. B. (2013) Redesign of a phenylalanine aminomutase into a phenylalanine ammonia lyase. *Chemcatchem* 5:1797-1802.

Berner M., Krug D., Bihlmaier C., Vente A., Muller R., and Bechthold A. (2006) Genes and enzymes involved in caffeic acid biosynthesis in the actinomycete saccharothrix espanaensis. *J Bacteriol* 188: 2666-2673.

Chesters C., Wilding M., Goodall M., and Micklefield J. (2012) Thermal bifunctionality of bacterial phenylalanine aminomutase and ammonia lyase enzymes. *Angew Chem Int Ed Engl* 51: 4344-4348.

Christenson S. D., Liu W., Toney M. D., and Shen B. (2003a) A novel 4-methylideneimidazole-5-one-containing tyrosine aminomutase in enediyne antitumor antibiotic C-1027 biosynthesis. *J Am Chem Soc* 125: 6062-6063.

Christenson S. D., Wu W., Spies M. A., Shen B., and Toney M. D. (2003b) Kinetic analysis of the 4-methylideneimidazole-5-one-containing tyrosine aminomutase in enediyne antitumor antibiotic C-1027 biosynthesis. Biochemistry 42: 12708-12718.

Holo H, and Nes I F. 1995. Transformation of *Lactococcus* by electroporation. Methods Mol. Biol. 47:195-199.

Horinouchi S., and Weisblum B. (1982) Nucleotide sequence and functional map of pC194, a plasmid that specifies inducible chloramphenicol resistance. *J Bacteriol* 150: 815-825.

Jensen N. B., Strucko T., Kildegaard K. R., David F., Maury J., Mortensen U. H., Forster J., Nielsen J., Borodina I. (2014) EasyClone: method for iterative chromosomal integration of multiple genes in *Saccharomyces cerevisiae*. FEMS Yeast Res. 14(2):238-48 Jin M., Fischbach M. A., and Clardy J. (2006) A biosynthetic gene cluster for the acetyl-CoA carboxylase inhibitor andrimid. J Am Chem Soc 128: 10660-10661.

Kyndt J. A., Meyer T. E., Cusanovich M. A., and Van Beeumen J. J. (2002) Characterization of a bacterial tyrosine ammonia lyase, a biosynthetic enzyme for the photoactive yellow protein. *FEBS Lett* 512: 240-244.

Kuipers O P, de Ruyter P G G A, Kleerebezem M, and de Vos W M. 1998. Quorum sensing-controlled gene expression in lactic acid bacteria. J. Biotechnol. 64:15-21.

Poolman B, and Konings W N. 1988. Relation of growth of *Streptococcus lactis* and *Streptococcus cremoris* to amino acid transport. J. Bacteriol. 170:700-707.

Rosler J., Krekel F., Amrhein N., and Schmid J. (1997) Maize phenylalanine ammonia-lyase has tyrosine ammonia-lyase activity. *Plant Physiol* 113: 175-179.

Schroeder A. C., Kumaran S., Hicks L. M., Cahoon R. E., Halls C., Yu O., and Jez J. M. (2008) Contributions of conserved serine and tyrosine residues to catalysis, ligand binding, and cofactor processing in the active site of tyrosine ammonia lyase. *Phytochemistry* 69: 1496-1506.

Strobel T., Al-Dilaimi A., Blom J., Gessner A., Kalinowski J., Luzhetska M., et al. (2012) Complete genome sequence of saccharothrix espanaensis DSM 44229(T) and comparison to the other completely sequenced pseudonocardiaceae. *BMC Genomics* 13: 465-2164-13-465.

Walker K. D., Klettke K., Akiyama T., and Croteau R. (2004) Cloning, heterologous expression, and characterization of a phenylalanine aminomutase involved in taxol biosynthesis. *J Biol Chem* 279: 53947-53954.

Williams J. S., Thomas M., and Clarke D. J. (2005) The gene stlA encodes a phenylalanine ammonia-lyase that is involved in the production of a stilbene antibiotic in *photorhabdus luminescens* TT01. Microbiology 151: 2543-2550.

Xiang L., and Moore B. S. (2002) Inactivation, complementation, and heterologous expression of encP, a novel bacterial phenylalanine ammonia-lyase gene. *J Biol Chem* 277: 32505-32509.

Zhu L., Cui W., Fang Y., Liu Y., Gao X., and Zhou Z. (2013) Cloning, expression and characterization of phenylalanine ammonia-lyase from *rhodotorula glutinis*. *Biotechnol Lett* 35:751-756.

Zhu Y., Liao S., Ye J., and Zhang H. (2012) Cloning and characterization of a novel tyrosine ammonia lyase-encoding gene involved in bagremycins biosynthesis in *streptomyces* sp. *Biotechnol Lett* 34: 269-274.

Embodiments of the Invention

1. Method for producing a hydroxycinnamic acid of general formula I

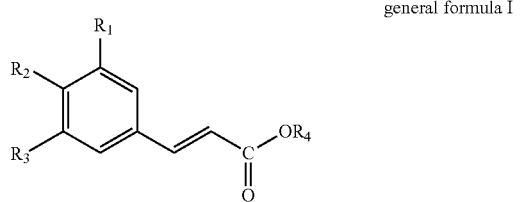

general formula I the method comprises deaminating a compound of general formula II

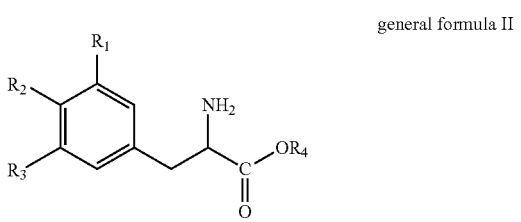

general formula II using a polypeptide selected from the group consisting of:
i) a polypeptide comprising an amino acid sequence set forth in SEQ ID NO: 1, 2 or 3;
ii) a polypeptide comprising an amino acid sequence which has at least about 70%, such as at least about 75%, at least about 80%, at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3; or
iii) a polypeptide comprising an amino acid sequence set forth in SEQ ID NO: 1, 2 or 3, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted;
wherein $R_1$, $R_2$ and $R_3$ independently are selected from the group consisting of hydrogen (H), hydroxyl (—OH), $C_{1-6}$-alkyl and $C_{1-6}$-Alkoxy, provided that at least one of $R_1$, $R_2$ and $R_3$ is hydroxyl (—OH); and $R_4$ is selected from the group consisting of hydrogen (—H) and $C_{1-6}$-alkyl.

2. The method according to item 1, wherein $R_2$ is hydroxyl.
3. The method according to item 1 or 2, wherein $R_4$ is hydrogen.
4. The method according to any one of items 1 to 3, wherein $R_1$ is hydrogen.
5. The method according any one of items 1 to 4, wherein $R_3$ is hydrogen or hydroxyl.
6. The method according to any one of items 1 to 5, wherein each of $R_1$, $R_3$ and $R_4$ is hydrogen, and $R_2$ is hydroxyl.
7. The method according to any one of items 1 to 5, wherein $R_1$ is hydrogen, $R_2$ is hydroxyl, $R_3$ is hydroxyl and $R_4$ is hydrogen.
8. The method according to any one of items 1 to 7, wherein the polypeptide according to ii) or iii) has tyrosine ammonia lyase activity.
9. The method according to any one of items 1 to 8, wherein the polypeptide according to ii) or iii) comprises the amino acid sequence set forth in SEQ ID NO: 4 or 5.
10. The method according to any one of items 1 to 9, wherein the polypeptide is in isolated form.
11. The method according to item 10, wherein the polypeptide is in purified form.
12. The method according to any one of items 1 to 9, wherein the polypeptide is expressed by a recombinant host cell.
13. The method according to item 12, wherein the recombinant host cell is a microorganism genetically modified to express the polypeptide.
14. The method according to item 12 or 13, wherein the recombinant host cell is selected from the group consisting of bacteria, yeasts, fungi, algae and plant cells.
15. The method according to item 12 or 13, wherein the recombinant host cell is a bacterium.
16. The method according to item 15, wherein the bacterium is a bacterium of the genus *Bacillus, Lactococcus, Lactobacillus, Clostridium, Corynebacterium, Geobacillus, Streptococcus, Pseudomonas, Streptomyces, Escherichia, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus,* or *Yersinia*.
17. The method according to item 15 or 16, wherein the bacterium is a bacterium of the genus *Bacillus, Lactococcus, Pseudomonas* or *Corynebacterium*.
18. The method according to item 15 or 16, wherein the bacterium is a bacterium of the genus *Bacillus*.
19. The method according to item 18, wherein the bacterium is *Bacillus subtilis*.
20. The method according to item 15 or 16, wherein the bacterium is a bacterium of the genus *Lactococcus*.
21. The method according to item 20, wherein the bacterium is *Lactococcus lactis*.
22. The method according to item 15 or 16, wherein the bacterium is a bacterium of the genus *Pseudomonas*.
23. The method according to item 22, wherein the bacterium is *Pseudomonas putida*.
24. The method according to item 15 or 16, wherein the bacterium is a bacterium of the genus *Corynebacterium*.

25. The method according to item 24, wherein the bacterium is *Corynebacterium glutamicum*.
26. The method according to item 15 or 16, wherein the bacterium is a bacterium of the genus *Escherichia*.
27. The method according to item 26, wherein the bacterium is *Escherichia coli*.
28. The method according to item 12 or 13, wherein the recombinant host cell is a yeast.
29. The method according to item 28, wherein the yeast is of the genus *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula,* or *Trichosporon*.
30. The method according to item 28 or 29, wherein the yeast is a yeast of the genus *Saccharomyces,* or *Pichia*.
31. The method according to any one of items 28 to 30, wherein the yeast is selected from the group consisting of *Saccharomyces cerevisiae, Pichia pastoris,* and *pichia* kudriavzevii.
32. The method according to any one of items 28 to 31, wherein the yeast is *Saccharomyces cerevisiae*.
33. The method according to any one of items 28 to 31, wherein the yeast is *Pichia pastoris*.
34. The method according to item 12 or 13, wherein the recombinant host cell is a fungus.
35. The method according to item 34, wherein the fungus is a fungus of the genus *Aspergillus*.
36. The method according to item 34 or 35, wherein the fungus is *Aspergillus Oryzae* or *Aspergillus niger*.
37. The method according to item 12 or 13, wherein the recombinant host cell is an algae cell.
38. The method according to item 37, wherein the algae cells is an algae cell of the genus *Haematococcus, Phaedactylum, Volvox* or *Dunaliella*.
39. The method according to item 12 or 13, wherein the recombinant host cell is a plant cell.
40. The method according to item 39, wherein the plant cell is selected from the group consisting of soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.
41. The method according to any one of items 12 to 40, wherein said recombinant host cell does not express a polypeptide having phenolic acid decarboxylase (PAD) activity.
42. The method according to any one of items 12 to 41, wherein a gene or gene cluster encoding a polypeptide having phenolic acid decarboxylase (PAD) activity has been inactivated.
43. The method according to any one of items 12 to 41, wherein said recombinant host cell does not contain within its genome a gene or gene cluster encoding a polypeptide having phenolic acid decarboxylase (PAD) activity.
44. A recombinant host cell comprising a heterologous polypeptide selected from the group consisting of:
    i) a polypeptide comprising an amino acid sequence set forth in SEQ ID NO: 1, 2 or 3;
    ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2 or 3; or
    iii) a polypeptide comprising an amino acid sequence set forth in SEQ ID NO: 1, 2 or 3, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.
45. The method according to item 44, wherein the polypeptide according to ii) or iii) has tyrosine ammonia lyase activity.
46. The method according to item 44 or 45, wherein the polypeptide according to ii) or iii) comprises the amino acid sequence set forth in SEQ ID NO: 4 or 5.
47. The recombinant host cell according to any one of items 44 to 46, the host cell comprises an exogenous nucleic acid molecule comprising a nucleotide sequence encoding said polypeptide.
48. The recombinant host cell according to item 47, the exogenous nucleic acid molecule further comprises a promoter that is functional in the host cell to cause the production of an mRNA molecule and that is operably linked to the nucleotide sequence encoding said polypeptide.
49. The recombinant host cell according to item 48, the exogenous nucleic acid molecule further comprises at least one regulatory element selected from a 5' untranslated region (5'UTR) and 3' untranslated region (3' UTR).
50. The recombinant host cell according to any one of items 47 to 49, wherein the exogenous nucleic acid molecule is a vector.
51. The recombinant host cell according to any one of items 47 to 49, wherein the exogenous nucleic acid molecule is stably integrated into the genome of the host cell.
52. The recombinant host cell according to any one of items 44 to 51, wherein the recombinant host cell is selected from the group consisting of bacteria, yeasts, fungi, algae and plant cells.
53. The recombinant host cell according to any one of items 44 to 52, wherein the recombinant host cell is a bacterium.
54. The recombinant host cell according to item 53, wherein the bacterium is a bacterium of the genus *Bacillus, Lactococcus, Lactobacillus, Clostridium, Corynebacterium, Geobacillus, Streptococcus, Pseudomonas, Streptomyces, Escherichia, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus,* or *Yersinia*.
55. The recombinant host cell according to item 53, wherein the bacterium is a bacterium of the genus *Bacillus*.
56. The recombinant host cell according to item 55, wherein the bacterium is *Bacillus subtilis*.
57. The recombinant host cell according to item 53, wherein the bacterium is a bacterium of the genus *Lactococcus*.
58. The recombinant host cell according to item 57, wherein the bacterium is *Lactococcus lactis*.
59. The recombinant host cell according to item 53, wherein the bacterium is a bacterium of the genus *Pseudomonas*.
60. The recombinant host cell according to item 59, wherein the bacterium is *Pseudomonas putida*.
61. The recombinant host cell according to item 53, wherein the bacterium is a bacterium of the genus *Corynebacterium*.
62. The recombinant host cell according to item 61, wherein the bacterium is *Corynebacteriumg lutamicum*.
63. The recombinant host cell according to item 53, wherein the bacterium is a bacterium of the genus *Escherichia*.

64. The recombinant host cell according to item 63, wherein the bacterium is *Escherichia coli*.
65. The recombinant host cell according to any one of items 44 to 52, wherein the recombinant host cell is a yeast.
66. The recombinant host cell according to item 65, wherein the yeast is of the genus *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.
67. The recombinant host cell according to item 65 or 66, wherein the yeast is a yeast of the genus *Saccharomyces* or *Pichia*.
68. The recombinant host cell according to any one of items 65 to 67, wherein the yeast is selected from the group consisting of *Saccharomyces cerevisiae, Pichia pastoris*, and *Pichia kudriavzevii*.
69. The recombinant host cell according to any one of items 65 to 67, wherein the yeast is *Saccharomyces cerevisiae*.
70. The recombinant host cell according to any one of items 64 to 67, wherein the yeast is *Pichia pastoris*.
71. The recombinant host cell according to any one of items 44 to 52, wherein the recombinant host cell is a fungus.
72. The recombinant host cell according to item 71, wherein the fungus is a fungus of the genus *Aspergillus*.
73. The recombinant host cell according to item 71 or 72, wherein the fungus is *Aspergillus Oryzae* or *Aspergillus niger*.
74. The recombinant host cell according to any one of items 44 to 52, wherein the recombinant host cell is an algae cell.
75. The recombinant host cell according to item 74, wherein the algae cells is an algae cell of the genus *Haematococcus, Phaedactylum, Volvox* or *Dunaliella*.
76. The recombinant host cell according to any one of items 44 to 52, wherein the recombinant host cell is a plant cell.
77. The recombinant host cell according to item 76, wherein the plant cell is selected from the group consisting of soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.
78. The recombinant host cell according to any one of items 44 to 77, wherein said recombinant host cell does not express a polypeptide having phenolic acid decarboxylase (PAD) activity.
79. The recombinant host cell according to any one of items 44 to 78, wherein a gene or gene cluster encoding a polypeptide having phenolic acid decarboxylase (PAD) activity has been inactivated.
80. The recombinant host cell according to any one of items 44 to 78, wherein said recombinant host cell does not contain within its genome a gene or gene cluster encoding a polypeptide having phenolic acid decarboxylase (PAD) activity.
81. A method for producing a hydroxycinnamic acid of general formula I

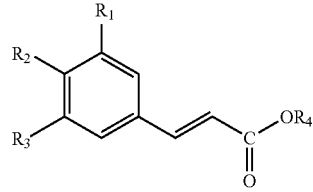

general formula I the method comprises the step of:
a) contacting a recombinant host cell according to any one of items 44 to 80 with a medium comprising a fermentable carbon substrate and/or a compound of the general formula II

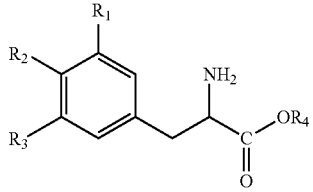

general formula II wherein $R_1$, $R_2$ and $R_3$ independently are selected from the group consisting of hydrogen (H), hydroxyl (—OH), $C_{1-6}$-alkyl and $C_{1-6}$-Alkoxy, provided that at least one of $R_1$, $R_2$ and $R_3$ is hydroxyl (—OH); and $R_4$ is selected from the group consisting of hydrogen (—H) and $C_{1-6}$-alkyl.
82. The method according to item 81, wherein $R_2$ is hydroxyl.
83. The method according to item 81 or 82, wherein $R_4$ is hydrogen.
84. The method according to any one of items 81 to 83, wherein $R_1$ is hydrogen.
85. The method according any one of items 81 to 84, wherein $R_3$ is hydrogen or hydroxyl.
86. The method according to any one of items 81 to 85, wherein each of $R_1$, $R_3$ and $R_4$ is hydrogen, and $R_2$ is hydroxyl.
87. The method according to any one of items 81 to 86, wherein $R_1$ is hydrogen, $R_2$ is hydroxyl, $R_3$ is hydroxyl and $R_4$ is hydrogen.
88 The method according to any one of items 81 to 87, further comprising the step of:
b) culturing the recombinant host cell under suitable conditions for the production of the hydroxcinnamic acid.
89. The method according to any one of items 81 to 88, further comprising the step of:

c) recovering the hydroxcinnamic acid.
90. Use of a polypeptide in the production of a hydroxycinnamic acid, said polypeptide being selected from the group consisting of:
i) a polypeptide comprising an amino acid sequence set forth in SEQ ID NO: 1, 2 or 3;
ii) a polypeptide comprising an amino acid sequence which has at least about 70%, such as at least about 75%, at least about 80%, at least about 85%, at least about 90%, at least about 93%, at least about 95%, at least about 96%, at least about 97%, at least about 98%, or at least about 99%, sequence identity to the amino acid sequence set forth in SEQ ID NO: 1, 2 or 3; or
iii) a polypeptide comprising an amino acid sequence set forth in SEQ ID NO: 1, 2 or 3, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted;

91. The use according to item 90, wherein the hydroxycinnamic acid is of the general formula I

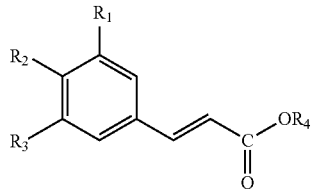

general formula I wherein $R_1$, $R_2$ and $R_3$ independently are selected from the group consisting of hydrogen (H), hydroxyl (—OH), $C_{1-6}$-alkyl and $C_{1-6}$-Alkoxy, provided that at least one of $R_1$, $R_2$ and $R_3$ is hydroxyl (—OH); and $R_4$ is selected from the group consisting of hydrogen (—H) and $C_{1-6}$-alkyl.

92. The use according to item 90 or 91, wherein the hydroxycinnamic acid is p-coumaric acid ($R_1$=H, $R_2$=OH, $R_3$=H, $R_4$=H).

---

What is claimed is:

1. A method for producing a hydroxycinnamic acid of general formula I:

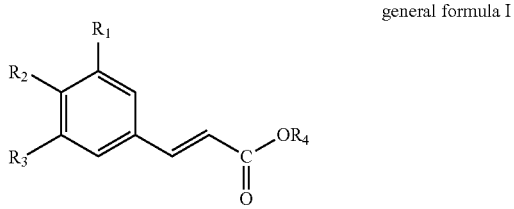

general formula I comprising:
contacting a recombinant host cell which has been genetically modified to express a heterologous polypeptide with a medium comprising a fermentable carbon substrate and/or a compound of the general formula II:

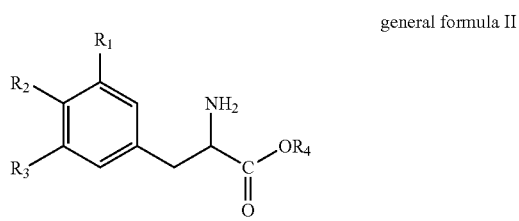

general formula II to produce a hydroxycinnamic acid of general formula I;
wherein said heterologous polypeptide is selected from:
i) a polypeptide comprising the amino acid sequence set forth in SEQ ID NO: 2 or 3; or
ii) a polypeptide comprising an amino acid sequence which has at least 85% sequence identity to the amino acid sequence set forth in SEQ ID NO: 2 or 3, wherein the polypeptide has tyrosine ammonia lyase activity;
wherein each of $R_1$, $R_3$, and $R_4$ is hydrogen (—H), and $R_2$ is hydroxyl (—OH), or
wherein $R_1$ is methoxyl (—OCH$_3$) or hydroxyl (—OH), $R_2$ is hydroxyl (—OH), and each of $R_3$ and $R_4$ is hydrogen (—H); and
wherein said recombinant host cell is a bacterium or yeast.

2. The method according to claim 1, wherein the recombinant host cell is a bacterium.

3. The method according to claim 2, wherein the bacterium is of the genus Bacillus, Lactococcus, Lactobacillus, Clostridium, Corynebacterium, Geobacillus, Streptococcus, Pseudomonas, Streptomyces, Escherichia, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus, or Yersinia.

4. The method according to claim 2, wherein the bacterium is of the genus Escherichia, Bacillus, Lactococcus, Lactobacillus, Corynebacterium, Streptomyces or Pseudomonas.

5. The method according to claim 2, wherein the bacterium is selected from the group consisting of Escherichia coli, Lactococcus lactis, Bacillus subtitlis, Bacillus amyloliquefaciens, Bacillus licheniformis, Bacillus mojavensis, Streptomyces lividans, Streptomyces griseus, Streptomyces coelicolor, Corynebacterium glutamicum, and Pseudomonas putida.

6. The method according to claim 2, wherein the bacterium is Escherichia coli, Lactococcus lactis or Bacillus subtitlis.

7. The method according to claim 2, wherein the bacterium is Escherichia coli.

8. The method according to claim 1, wherein the recombinant host cell is a yeast.

9. The method according to claim 8, wherein the yeast is of the genus Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula, or Trichosporon.

10. The method according to claim 8, wherein the yeast is of the genus Saccharomyces or Pichia.

11. The method according to claim 8, wherein the yeast is selected from the group consisting of Saccharomyces cerevisiae, Pichia pastoris, and Pichia kudriavzevii.

12. The method according to claim 8, wherein the yeast is Saccharomyces cerevisiae.

13. The method according to claim 1, wherein said recombinant host cell does not express a polypeptide having phenolic acid decarboxylase (PAD) activity.

14. The method according to claim 1, wherein the polypeptide comprises the amino acid sequence set forth in SEQ ID NO: 2 or 3.

15. A method for producing a hydroxycinnamic acid of general formula I:

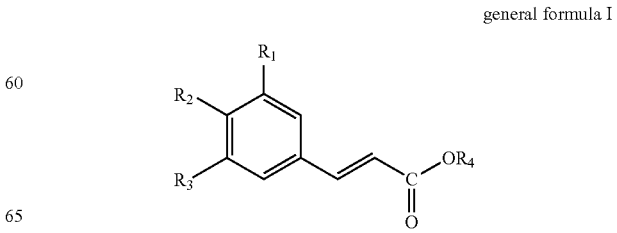

general formula I comprising:

a) contacting a compound of general formula II:

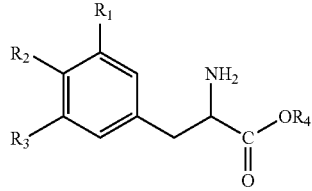

general formula II with a polypeptide to produce a hydroxycinnamic acid of general formula I, wherein the polypeptide is selected from:
i) a polypeptide comprising the amino acid sequence set forth in SEQ ID NO: 2 or 3; or
ii) a polypeptide comprising an amino acid sequence which has at least 80% sequence identity to the amino acid sequence set forth in SEQ ID NO: 2 or 3, wherein the polypeptide has tyrosine ammonia lyase activity; and b) measuring the concentration of said hydroxycinnamic acid of general formula I or recovering said hydroxycinnamic acid of general formula I;

wherein each of $R_1$, $R_3$, and $R_4$ is hydrogen (—H), and $R_2$ is hydroxyl (—OH), or wherein $R_1$ is methoxyl (—OCH$_3$) or hydroxyl (—OH), $R_2$ is hydroxyl (—OH), and each of $R_3$ and $R_4$ is hydrogen (—H).

16. A method for producing a hydroxycinnamic acid of general formula I:

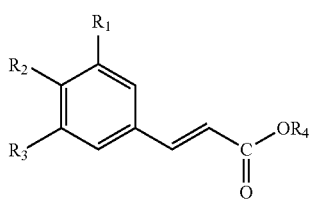

general formula I comprising:

a) contacting a recombinant host cell which has been genetically modified to express a heterologous polypeptide with a medium comprising a fermentable carbon substrate and/or a compound of the general formula II:

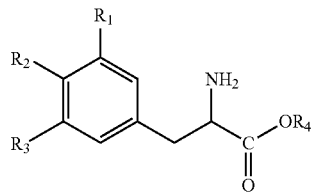

general formula II to produce a hydroxycinnamic acid of general formula I; wherein said heterologous polypeptide is selected from:
i) a polypeptide comprising the amino acid sequence set forth in SEQ ID NO: 2 or 3; or
ii) a polypeptide comprising an amino acid sequence which has at least 80% sequence identity to the amino acid sequence set forth in SEQ ID NO: 2 or 3, wherein the polypeptide has tyrosine ammonia lyase activity; and b) measuring the concentration of said hydroxycinnamic acid of general formula I or recovering said hydroxycinnamic acid of general formula I;

wherein each of $R_1$, $R_3$, and $R_4$ is hydrogen (—H), and $R_2$ is hydroxyl (—OH), or wherein $R_1$ is methoxyl (—OCH$_3$) or hydroxyl (—OH), $R_2$ is hydroxyl (—OH), and each of $R_3$ and $R_4$ is hydrogen (—H).

17. The method according to claim 16, wherein the recombinant host cell is a bacterium.

18. The method according to claim 17, wherein the bacterium is selected from the group consisting of *Escherichia coli, Lactococcus lactis, Bacillus subtitlis, Bacillus amyloliquefaciens, Bacillus licheniformis, Bacillus mojavensis, Streptomyces lividans, Streptomyces griseus, Streptomyces coelicolor, Corynebacterium glutamicum,* and *Pseudomonas putida.*

19. The method according to claim 17, wherein the bacterium is *Escherichia coli.*

20. The method according to claim 16, wherein the recombinant host cell is a yeast.

21. The method according to claim 20, wherein the yeast is selected from the group consisting of *Saccharomyces cerevisiae, Pichia pastoris,* and *Pichia kudriavzevii.*

22. The method according to claim 1, wherein the polypeptide comprises an amino acid sequence which has at least 90% sequence identity to the amino acid sequence set forth in SEQ ID NO: 2 or 3.

23. The method according to claim 1, wherein the polypeptide comprises an amino acid sequence which has at least 95% sequence identity to the amino acid sequence set forth in SEQ ID NO: 2 or 3.

* * * * *

UNITED STATES PATENT AND TRADEMARK OFFICE
CERTIFICATE OF CORRECTION

PATENT NO. : 11,306,331 B2
APPLICATION NO. : 16/938762
DATED : April 19, 2022
INVENTOR(S) : Christian Bille Jendresen et al.

It is certified that error appears in the above-identified patent and that said Letters Patent is hereby corrected as shown below:

On the Title Page

Item (56), Column 2 (Other Publications), Line 3, delete "Chern." and insert -- Chem. --.

In the Specification

Column 1, Line 56, delete "ammonialyase" and insert -- ammonia lyase --.

Column 2, Line 31, delete "TO" and insert -- Tü --.

Column 3, Line 11 (approx.), delete "formula" and insert -- formula II --.

Column 4, Line 6-9, delete "The method may further comprise the step culturing the recombinant host cell under suitable conditions for the production of the hydroxycinnamic acid, and further optionally the recovery of the hydroxycinnamic acid." and insert the same on Column 4, Line 5 as a continuation of the same paragraph.

Column 4, Line 34, delete "CDM" and insert -- CDM. --.

Signed and Sealed this
Twenty-fifth Day of October, 2022

Katherine Kelly Vidal
*Director of the United States Patent and Trademark Office*

SEQUENCE LISTING

<160> NUMBER OF SEQ ID NOS: 85

<210> SEQ ID NO 1
<211> LENGTH: 506
<212> TYPE: PRT
<213> ORGANISM: Flavobacterium johnsoniae

<400> SEQUENCE: 1

Met Asn Thr Ile Asn Glu Tyr Leu Ser Leu Glu Glu Phe Glu Ala Ile
1               5                   10                  15

Ile Phe Gly Asn Gln Lys Val Thr Ile Ser Asp Val Val Asn Arg
            20                  25                  30

Val Asn Glu Ser Phe Asn Phe Leu Lys Glu Phe Ser Gly Asn Lys Val
        35                  40                  45

Ile Tyr Gly Val Asn Thr Gly Phe Gly Pro Met Ala Gln Tyr Arg Ile
    50                  55                  60

Lys Glu Ser Asp Gln Ile Gln Leu Gln Tyr Asn Leu Ile Arg Ser His
65                  70                  75                  80

Ser Ser Gly Thr Gly Lys Pro Leu Ser Pro Val Cys Ala Lys Ala Ala
            85                  90                  95

Ile Leu Ala Arg Leu Asn Thr Leu Ser Leu Gly Asn Ser Gly Val His
            100                 105                 110

Pro Ser Val Ile Asn Leu Met Ser Glu Leu Ile Asn Lys Asp Ile Thr
            115                 120                 125

Pro Leu Ile Phe Glu His Gly Val Gly Ala Ser Gly Asp Leu Val
    130                 135                 140

Gln Leu Ser His Leu Ala Leu Val Leu Ile Gly Glu Gly Glu Val Phe
145                 150                 155                 160

Tyr Lys Gly Glu Arg Arg Pro Thr Pro Glu Val Phe Glu Ile Glu Gly
            165                 170                 175

Leu Lys Pro Ile Gln Val Glu Ile Arg Glu Gly Leu Ala Leu Ile Asn
            180                 185                 190

Gly Thr Ser Val Met Thr Gly Ile Gly Val Val Asn Val Tyr His Ala
        195                 200                 205

```
Lys Lys Leu Leu Asp Trp Ser Leu Lys Ser Ser Cys Ala Ile Asn Glu
    210                 215                 220

Leu Val Gln Ala Tyr Asp Asp His Phe Ser Ala Glu Leu Asn Gln Thr
225                 230                 235                 240

Lys Arg His Lys Gly Gln Gln Glu Ile Ala Leu Lys Met Arg Gln Asn
                245                 250                 255

Leu Ser Asp Ser Thr Leu Ile Arg Lys Arg Glu Asp His Leu Tyr Ser
            260                 265                 270

Gly Glu Asn Thr Glu Glu Ile Phe Lys Glu Lys Val Gln Glu Tyr Tyr
        275                 280                 285

Ser Leu Arg Cys Val Pro Gln Ile Leu Gly Pro Val Leu Glu Thr Ile
    290                 295                 300

Asn Asn Val Ala Ser Ile Leu Glu Asp Glu Phe Asn Ser Ala Asn Asp
305                 310                 315                 320

Asn Pro Ile Ile Asp Val Lys Asn Gln His Val Tyr His Gly Gly Asn
                325                 330                 335

Phe His Gly Asp Tyr Ile Ser Leu Glu Met Asp Lys Leu Lys Ile Val
            340                 345                 350

Ile Thr Lys Leu Thr Met Leu Ala Glu Arg Gln Leu Asn Tyr Leu Leu
        355                 360                 365

Asn Ser Lys Ile Asn Glu Leu Leu Pro Pro Phe Val Asn Leu Gly Thr
    370                 375                 380

Leu Gly Phe Asn Phe Gly Met Gln Gly Val Gln Phe Thr Ala Thr Ser
385                 390                 395                 400

Thr Thr Ala Glu Ser Gln Met Leu Ser Asn Pro Met Tyr Val His Ser
                405                 410                 415

Ile Pro Asn Asn Asn Asp Asn Gln Asp Ile Val Ser Met Gly Thr Asn
            420                 425                 430

Ser Ala Val Ile Thr Ser Lys Val Ile Glu Asn Ala Phe Glu Val Leu
        435                 440                 445

Ala Ile Glu Met Ile Thr Ile Val Gln Ala Ile Asp Tyr Leu Gly Gln
    450                 455                 460

Lys Asp Lys Ile Ser Ser Val Ser Lys Lys Trp Tyr Asp Glu Ile Arg
465                 470                 475                 480

Asn Ile Ile Pro Thr Phe Lys Glu Asp Gln Val Met Tyr Pro Phe Val
                485                 490                 495

Gln Lys Val Lys Asp His Leu Ile Asn Asn
            500                 505

<210> SEQ ID NO 2
<211> LENGTH: 552
<212> TYPE: PRT
<213> ORGANISM: Herpetosiphon aurantiacus

<400> SEQUENCE: 2

Met Ser Thr Thr Leu Ile Leu Thr Gly Glu Gly Leu Gly Ile Asp Asp
1               5                   10                  15

Val Val Arg Val Ala Arg His Gln Asp Arg Val Glu Leu Thr Thr Asp
                20                  25                  30

Pro Ala Ile Leu Ala Gln Ile Glu Ala Ser Cys Ala Tyr Ile Asn Gln
            35                  40                  45

Ala Val Lys Glu His Gln Pro Val Tyr Gly Val Thr Thr Gly Phe Gly
        50                  55                  60

Gly Met Ala Asn Val Ile Ile Ser Pro Glu Glu Ala Ala Glu Leu Gln
65                  70                  75                  80
```

```
Asn Asn Ala Ile Trp Tyr His Lys Thr Gly Ala Gly Lys Leu Leu Pro
                85                  90                  95

Phe Thr Asp Val Arg Ala Ala Met Leu Leu Arg Ala Asn Ser His Met
            100                 105                 110

Arg Gly Ala Ser Gly Ile Arg Leu Glu Ile Ile Gln Arg Met Val Thr
        115                 120                 125

Phe Leu Asn Ala Asn Val Thr Pro His Val Arg Glu Phe Gly Ser Ile
    130                 135                 140

Gly Ala Ser Gly Asp Leu Val Pro Leu Ile Ser Ile Thr Gly Ala Leu
145                 150                 155                 160

Leu Gly Thr Asp Gln Ala Phe Met Val Asp Phe Asn Gly Glu Thr Leu
                165                 170                 175

Asp Cys Ile Ser Ala Leu Glu Arg Leu Gly Leu Pro Arg Leu Arg Leu
            180                 185                 190

Gln Pro Lys Glu Gly Leu Ala Met Met Asn Gly Thr Ser Val Met Thr
        195                 200                 205

Gly Ile Ala Ala Asn Cys Val His Asp Ala Arg Ile Leu Leu Ala Leu
    210                 215                 220

Ala Leu Glu Ala His Ala Leu Met Ile Gln Gly Leu Gln Gly Thr Asn
225                 230                 235                 240

Gln Ser Phe His Pro Phe Ile His Arg His Lys Pro His Thr Gly Gln
                245                 250                 255

Val Trp Ala Ala Asp His Met Leu Glu Leu Leu Gln Gly Ser Gln Leu
            260                 265                 270

Ser Arg Asn Glu Leu Asp Gly Ser His Asp Tyr Arg Asp Gly Asp Leu
        275                 280                 285

Ile Gln Asp Arg Tyr Ser Leu Arg Cys Leu Pro Gln Phe Leu Gly Pro
    290                 295                 300

Ile Ile Asp Gly Met Ala Phe Ile Ser His His Leu Arg Val Glu Ile
305                 310                 315                 320

Asn Ser Ala Asn Asp Asn Pro Leu Ile Asp Thr Ala Ser Ala Ala Ser
                325                 330                 335

Tyr His Gly Gly Asn Phe Leu Gly Gln Tyr Ile Gly Val Gly Met Asp
            340                 345                 350

Gln Leu Arg Tyr Tyr Met Gly Leu Met Ala Lys His Leu Asp Val Gln
        355                 360                 365

Ile Ala Leu Leu Val Ser Pro Gln Phe Asn Asn Gly Leu Pro Ala Ser
    370                 375                 380

Leu Val Gly Asn Ile Gln Arg Lys Val Asn Met Gly Leu Lys Gly Leu
385                 390                 395                 400

Gln Leu Thr Ala Asn Ser Ile Met Pro Ile Leu Thr Phe Leu Gly Asn
                405                 410                 415

Ser Leu Ala Asp Arg Phe Pro Thr His Ala Glu Gln Phe Asn Gln Asn
            420                 425                 430

Ile Asn Ser Gln Gly Phe Gly Ser Ala Asn Leu Ala Arg Gln Thr Ile
        435                 440                 445

Gln Thr Leu Gln Gln Tyr Ile Ala Ile Thr Leu Met Phe Gly Val Gln
    450                 455                 460

Ala Val Asp Leu Arg Thr His Lys Leu Ala Gly His Tyr Asn Ala Ala
465                 470                 475                 480

Glu Leu Leu Ser Pro Leu Thr Ala Lys Ile Tyr His Ala Val Arg Ser
                485                 490                 495
```

```
Ile Val Lys His Pro Pro Ser Pro Glu Arg Pro Tyr Ile Trp Asn Asp
            500             505                 510

Asp Glu Gln Val Leu Glu Ala His Ile Ser Ala Leu Ala His Asp Ile
        515                 520                 525

Ala Asn Asp Gly Ser Leu Val Ser Ala Val Glu Gln Thr Leu Ser Gly
    530                 535                 540

Leu Arg Ser Ile Ile Leu Phe Arg
545             550

<210> SEQ ID NO 3
<211> LENGTH: 552
<212> TYPE: PRT
<213> ORGANISM: Herpetosiphon aurantiacus

<400> SEQUENCE: 3

Met Arg His Gln Val Thr Leu Thr Gly Ala Gly Leu Thr Ile Glu Asp
1               5                   10                  15

Val Val Arg Val Ala Arg His His Gln Pro Val Gly Leu Thr Asp Asn
            20                  25                  30

Pro Glu Ile Leu Gln Arg Ile Glu Asp Ser Cys Ala Tyr Ile Asn Asp
        35                  40                  45

Ala Val Lys Ala Ser Lys Pro Val Tyr Gly Val Thr Thr Gly Phe Gly
    50                  55                  60

Gly Met Ala Asp Val Val Ile Ser Ser Glu Glu Ala Ala Asp Leu Gln
65                  70                  75                  80

Asn Asn Ala Ile Trp Tyr His Lys Thr Gly Ala Gly Lys Leu Leu Pro
                85                  90                  95

Leu Ala Asp Val Arg Ala Ala Met Leu Leu Arg Ala Asn Ser His Met
            100                 105                 110

Arg Gly Val Ser Gly Ile Arg Leu Glu Ile Ile Gln Arg Met Met Thr
        115                 120                 125

Phe Leu Asn Ala Asn Val Thr Pro His Val Arg Glu Phe Gly Ser Ile
130                 135                 140

Gly Ala Ser Gly Asp Leu Val Pro Leu Ile Ser Ile Thr Gly Ala Leu
145                 150                 155                 160

Leu Gly Thr Asp Pro Ala Phe Arg Val Asp Phe Gly Glu Asn Ile
                165                 170                 175

Asp Cys Leu Glu Ala Leu Glu Arg Leu Asn Leu Pro Arg Leu Glu Leu
            180                 185                 190

Leu Pro Lys Glu Gly Leu Ala Met Met Asn Gly Thr Ser Val Met Thr
        195                 200                 205

Gly Ile Ala Ser Asn Val Leu His Asp Ala Arg Ile Leu Leu Gly Leu
    210                 215                 220

Ala Leu Asn Ile His Gly Leu Met Ile Gln Gly Leu Gln Gly Thr Asn
225                 230                 235                 240

Gln Ser Phe His Pro Phe Ile His Gln His Lys Ala His Thr Gly Gln
                245                 250                 255

Val Trp Ala Ala Asp His Met Leu Gln Ile Leu Glu Gly Ser Ala Leu
            260                 265                 270

Ser Arg Asp Glu Leu Asp Gly Arg His Glu Tyr Arg Glu Gly Asp Leu
        275                 280                 285

Ile Gln Asp Arg Tyr Ser Leu Arg Cys Leu Pro Gln Phe Leu Gly Pro
    290                 295                 300

Ile Ile Asp Gly Met Ala Tyr Ile Thr His His Leu Arg Val Glu Ile
305                 310                 315                 320
```

Asn Ser Ala Asn Asp Asn Pro Leu Ile Asn Thr Glu Ala Gly Ala Ser
                325                 330                 335

Tyr His Gly Gly Asn Phe Leu Gly Gln Tyr Ile Gly Val Gly Met Asp
            340                 345                 350

Gln Leu Arg Tyr Tyr Met Gly Leu Met Ala Lys His Leu Asp Val Gln
        355                 360                 365

Ile Ala Leu Leu Val Ser Pro Gln Phe Asn Asn Gly Leu Ser Ala Ser
    370                 375                 380

Leu Val Gly Asn Thr Asp Arg Lys Val Asn Met Gly Leu Lys Gly Leu
385                 390                 395                 400

Gln Ile Ser Gly Asn Ser Ile Met Pro Ile Leu Gly Phe Leu Gly Asn
                405                 410                 415

Ser Leu Ala Asp Arg Phe Pro Thr His Ala Glu Gln Phe Asn Gln Asn
            420                 425                 430

Ile Asn Ser Gln Gly Phe Gly Ser Ala Asn Leu Ala Arg Gln Thr Ile
        435                 440                 445

Glu Thr Leu Gln Gln Tyr Ile Ala Ile Ala Leu Ile Phe Gly Val Gln
    450                 455                 460

Ala Val Asp Leu Arg Thr Phe Lys Arg Thr Gly His Tyr Asn Ala Val
465                 470                 475                 480

Glu Thr Leu Ser Pro Met Thr Ala Lys Leu Tyr Ser Ala Met Arg Glu
                485                 490                 495

Val Val Gly Lys Pro Ile Ser His Glu Arg Pro Tyr Ile Trp Asn Asp
            500                 505                 510

Asn Glu Gln Ala Leu Glu Gln His Ile Ser Ala Ile Val Ser Asp Ile
        515                 520                 525

Thr Asn Asp Gly Ile Ile Pro Gln Ala Ile Gln Glu Thr Leu Asp Ser
    530                 535                 540

Leu Arg Ser Ile Ile Leu Phe Ala
545                 550

<210> SEQ ID NO 4
<211> LENGTH: 8
<212> TYPE: PRT
<213> ORGANISM: Flavobacterium johnsoniae

<400> SEQUENCE: 4

Leu Ile Arg Ser His Ser Ser Gly
1               5

<210> SEQ ID NO 5
<211> LENGTH: 8
<212> TYPE: PRT
<213> ORGANISM: Herpetosiphon aurantiacus

<400> SEQUENCE: 5

Ala Ile Trp Tyr His Lys Thr Gly
1               5

<210> SEQ ID NO 6
<211> LENGTH: 1521
<212> TYPE: DNA
<213> ORGANISM: Artificial Sequence
<220> FEATURE:
<223> OTHER INFORMATION: DNA sequence of FjXAL (SEQ ID NO: 1) codon
      optimized for expression in E. coli

<400> SEQUENCE: 6

```
atgaacacca tcaacgaata tctgagcctg aagaatttg  aagccattat ctttggcaat    60
cagaaagtga ccattagtga tgttgttgtg aatcgcgtta acgagagctt taactttctg   120
aaagaattta gcggcaacaa agtgatctat ggtgtgaata ccggttttgg tccgatggca   180
cagtatcgta ttaaagaaag cgatcagatt cagctgcagt ataatctgat tcgtagccat   240
agcagcggca ccggtaaacc gctgagtccg gtttgtgcaa aagcagcaat tctggcacgt   300
ctgaataccc tgagtctggg taatagcggt gttcatccga gcgttattaa tctgatgagc   360
gaactgatca acaaagatat cacaccgctg attttgaac atggtggtgt tggtgcaagc   420
ggtgatctgg ttcagctgag ccatctggca ctggttctga ttggtgaagg tgaagttttc   480
tataaaggtg aacgtcgtcc gacaccggaa gttttgaaa ttgaaggtct gaaaccgatc   540
caggtggaaa ttcgcgaagg tctggccctg attaatggca ccagcgttat gaccggtatt   600
ggtgttgtta atgtgtacca tgcaaaaaaa ctgctggatt ggagcctgaa aagcagctgt   660
gcaattaatg aactggttca ggcatatgat gatcacttta gcgcagaact gaatcagacc   720
aaacgtcata aggtcagca gaaattgca ctgaaaatgc gtcagaatct gagcgatagc   780
accctgattc gcaaacgtga agatcatctg tatagcggtg aaaacaccga agaaatcttc   840
aaagaaaaag tgcaagagta ttatagcctg cgttgtgttc cgcagattct gggtccggtt   900
ctggaaacca ttaacaatgt tgcaagcatt ctggaagatg aatttaacag cgcaaacgat   960
aacccgatca tcgatgttaa aaaccagcat gtttatcacg tggcaatttt tcatggtgat  1020
tatatcagcc tggaaatgga taaactgaaa atcgtgatta ccaaactgac catgctggca  1080
gaacgtcagc tgaattatct gctgaatagc aaaattaacg aactgctgcc tccgtttgtt  1140
aatctgggca ccctgggttt taactttggt atgcagggtg ttcagtttac cgcaaccagc  1200
accaccgcag aaagccagat gctgagcaat ccgatgtatg ttcatagcat tccgaacaat  1260
aatgataacc aggatattgt tagcatgggc accaatagcg cagttattac cagcaaagtt  1320
atcgaaaatg cctttgaagt tctggccatt gaaatgatta ccattgttca ggcgattgat  1380
tatctgggcc agaaagataa aatcagcagc gttagcaaaa atggtatga tgaaatccgc  1440
aacatcatcc cgacctttaa agaagatcag gtgatgtatc cgttcgtgca gaaagtaaaa  1500
gaccacctga ttaacaatta a                                            1521
```

<210> SEQ ID NO 7
<211> LENGTH: 1659
<212> TYPE: DNA
<213> ORGANISM: Artificial Sequence
<220> FEATURE:
<223> OTHER INFORMATION: DNA sequence of HaXAL1 (SEQ ID NO: 2) codon optimized for expression in E. coli

<400> SEQUENCE: 7

```
atgagcacca ccctgattct gaccggtgaa ggtctgggta ttgatgatgt tgttcgtgtt    60
gcacgtcatc aggatcgtgt tgaactgacc accgatccgg caattctggc acagattgaa   120
gcaagctgtg cctatattaa ccaggccgtt aaagaacatc agccggttta tggtgttacc   180
accggttttg gtggtatggc aaatgtgatt attagtccgg aagaagcagc agaactgcag   240
aataatgcaa tctggtatca taaaacaggt gccggtaaac tgctgccgtt acagatgtt   300
cgtgcagcaa tgctgctgcg tgcaaatagc catatgcgtg gtgcaagcgg tattcgtctg   360
gaaattattc agcgtatggt gacctttctg aatgcaaatg ttacaccgca tgttcgtgaa   420
tttggtagca ttggtgccag cggtgatctg gttccgctga tagcattac cggtgcactg   480
```

```
ctgggcaccg atcaggcatt tatggttgat tttaatggtg aaaccctgga ttgtattagc    540
gcactggaac gtctgggtct gcctcgtctg cgtctgcagc cgaaagaagg cctggcaatg    600
atgaatggca ccagcgttat gaccggtatt gcagcaaatt gtgttcatga tgcacgtatt    660
ctgctggcac tggccctgga agcacatgca ctgatgattc agggtctgca gggtacaaat    720
cagagctttc atccgtttat ccatcgtcat aaaccgcata caggtcaggt tgggcagca     780 gatcatatgc tggaactgct gcagggttca cagctgagcc gtaatgaact ggatggtagc    840
catgattatc gtgatggtga tctgattcag gatcgctata gcctgcgttg tctgccgcag    900
tttctgggtc cgattattga tggtatggcc tttattagcc atcatctgcg tgttgaaatt    960
aacagcgcaa atgataaccc gctgattgat accgcaagcg cagcaagcta tcatggtggt   1020
aattttctgg ccagtatat tggtgttggt atggatcagc tgcgctatta tatgggtctg    1080
atggcaaaac atctggatgt tcagattgcc ctgctggtta gtccgcagtt taataacggt   1140
ctgcctgcaa gcctggttgg taatattcag cgcaaagtta atatgggcct gaaaggtctg   1200
cagctgaccg caaatagcat tatgccgatt ctgacatttc tgggtaatag cctggcagat   1260
cgttttccga cccatgcaga acagtttaat cagaatatta cagccaggg ttttggtagc    1320 gcaaatctgg cacgtcagac cattcagacc ctgcaacagt atatcgcaat tacccctgatg 1380 tttggtgttc aggcagttga tctgcgtacc cataaactgg caggtcatta aacgcagcc    1440 gaactgctga gtccgctgac cgccaaaatc tatcatgcag ttcgtagcat tgttaaacat   1500
cctccgagtc cggaacgtcc gtatatttgg aatgatgatg aacaggttct ggaagcccat   1560
atttcagcac tggcacatga tattgcaaat gatggtagtc tggttagcgc agttgaacag   1620
accctgtcag gtctgcgtag tattattctg tttcgctaa                          1659
```

<210> SEQ ID NO 8
<211> LENGTH: 1659
<212> TYPE: DNA
<213> ORGANISM: Artificial Sequence
<220> FEATURE:
<223> OTHER INFORMATION: DNA sequence of HaXAL2 (SEQ ID NO: 3) codon
optimized for expression in E. coli

<400> SEQUENCE: 8

```
atgcgtcatc aggttaccct gaccggtgca ggtctgacca ttgaagatgt tgttcgtgtt     60
gcacgtcatc atcagccggt tggtctgacc gataatccgg aaattctgca gcgtattgaa    120
gatagctgtg cctatattaa cgatgcagtt aaagcaagca accggtgta tggtgttacc     180 accggttttg gtggtatggc cgatgttgtt attagcagcg aagaagcagc cgatctgcag    240
aataatgcaa tctggtatca taaaacaggt gccggtaaac tgctgccgct ggcagatgtt    300
cgtgcagcaa tgctgctgcg tgcaaatagc catatgcgtg gtgttagcgg tattcgtctg    360
gaaattattc agcgcatgat gaccttttctg aatgcaaatg ttacaccgca tgttcgtgaa    420
tttggtagca ttggtgcaag cggtgatctg gttccgctga ttagcattac cggtgcactg    480
ctgggcaccg atccggcatt cgtgttgat tttgatggcg aaaatatcga ttgtctggaa    540
gcactggaac gtctgaatct gccacgtctg gaactgctgc ctaaagaagg tctggcaatg    600
atgaatggca ccagcgttat gaccggtatt gcaagcaatt ttctgcatga tgcacgtatt    660
ctgctgggtc tggcactgaa cattcatggt ctgatgattc agggtctgca gggcaccaat   720
cagagctttc atccgtttat tcatcagcat aaagcacata caggtcaggt tgggcagca    780 gatcatatgc tgcagattct ggaaggtagc gcactgagcc gtgatgaact ggatggtcgt   840
```

-continued

| | |
|---|---|
| catgaatatc gtgaaggtga tctgattcag gatcgttata gcctgcgttg tctgccgcag | 900 |
| tttctgggtc cgattattga tggtatggca tatattaccc atcatctgcg tgttgaaatt | 960 |
| aacagcgcaa atgataatcc gctgatcaat accgaagccg gtgcaagcta tcatggtggt | 1020 |
| aattttctgg gccagtatat tggtgttggt atggatcagc tgcgctatta tatgggtctg | 1080 |
| atggcaaaac atctggatgt tcagattgcc ctgctggtta gtccgcagtt taataacggt | 1140 |
| ctgagcgcaa gcctggttgg taataccgat cgtaaagtta atatgggcct gaaaggtctg | 1200 |
| cagattagcg gtaatagcat tatgccgatt ctgggttttc tgggtaatag cctggcagat | 1260 |
| cgttttccga cccatgccga acagtttaat cagaatatta cagccagggg ttttggtagc | 1320 |
| gcaaatctgg cacgtcagac aattgaaacc ctgcagcagt atatcgcaat tgcactgatt | 1380 |
| tttggtgttc aggcagttga tctgcgtacc tttaaacgta caggtcatta taacgcagtg | 1440 |
| gaaaccctga gcccgatgac cgcaaaactg tatagcgcaa tgccgtgaagt tgtgggtaaa | 1500 |
| ccgattagcc atgaacgtcc gtatatttgg aatgataatg aacaggccct ggaacagcat | 1560 |
| attagcgcaa ttgttagcga tattaccaat gatggtatta ttccgcaggc cattcaagaa | 1620 |
| accctggata gtctgcgtag tattattctg tttgcctaa | 1659 |

<210> SEQ ID NO 9
<211> LENGTH: 1521
<212> TYPE: DNA
<213> ORGANISM: Artificial Sequence
<220> FEATURE:
<223> OTHER INFORMATION: DNA sequence of FjXAL (SEQ ID NO:1) codon
   optimized for expression in S. cerevisiae

<400> SEQUENCE: 9

| | |
|---|---|
| atgaacacca tcaacgaata cttgtccttg gaagaattcg aagccatcat cttcggtaat | 60 |
| caaaaggtta ccatctccga tgttgttgtc aacagagtta acgaatcctt caacttcttg | 120 |
| aaagaattct ccggtaacaa ggttatctac ggtgttaata ctggttttgg tccaatggct | 180 |
| caatacagaa tcaaagaatc cgaccaaatc caattgcaat acaacttgat cagatcccac | 240 |
| tcttctggta ctggtaaacc attgtctcca gttgtgccta aagctgctat tttggctaga | 300 |
| ttgaacactt tgtctttggg taattcaggt gttcacccat ccgttattaa cttgatgtcc | 360 |
| gaattgatca acaaggacat tacccccattg atctttgaac atggtggtgt tggtgcttca | 420 |
| ggtgatttgg ttcaattgtc tcatttggcc ttggttttga ttggtgaagg tgaagttttt | 480 |
| tacaagggtg aaagaagacc aaccccagaa gttttgaaa tcgaaggttt gaagccaatc | 540 |
| caagtcgaaa ttagagaagg tttggctttg atcaacggta cttctgttat gactggtatc | 600 |
| ggtgttgtta atgtttacca cgctaagaag ttgttggatt ggtccttgaa atcttcctgc | 660 |
| gctattaacg aattggttca agcttacgat gatcacttct ccgctgaatt gaatcaaact | 720 |
| aagagacaca agggtcaaca agaaattgcc ttgaagatga caaaaacttg gtccgattct | 780 |
| accttgatta gaagagagga agatcacttg tactccggtg aaaacaccga gaaatcttc | 840 |
| aaagaaaagg tccaagaata ttactccttg agatgcgttc acaaatttt gggtccagtt | 900 |
| ttggaaacca ttaacaatgt tgcctccatc ttggaagatg aattcaactc tgctaacgac | 960 |
| aacccaatca tcgatgttaa gatcaacac gtttaccatg gtggtaattt ccacggtgat | 1020 |
| tacatctcat tggaaatgga caagttgaag atcgtcatta ccaagttgac tatgttggcc | 1080 |
| gaaagacaat tgaattactt gttgaactcc aaaatcaatg aattattgcc accattcgtc | 1140 |
| aatttgggta ctttgggttt taacttcggt atgcaaggtg ttcaattcac tgctacttct | 1200 |

```
actactgctg aatcccaaat gttgtctaac cctatgtacg ttcattccat cccaaacaac    1260
aacgacaatc aagacatagt ctctatgggt acaaactccg ctgttattac ctccaaggtt    1320
attgaaaacg ccttcgaagt tttggccatt gaaatgatta ctatcgttca agccatcgac    1380
tacttgggtc aaaaggataa gatttcctcc gtcagtaaaa agtggtacga cgaaatcaga    1440
aacatcatcc caactttcaa agaagatcaa gtcatgtacc cattcgtcca aaaagttaag    1500
gatcacttga ttaacaactg a                                              1521
```

<210> SEQ ID NO 10
<211> LENGTH: 1659
<212> TYPE: DNA
<213> ORGANISM: Artificial Sequence
<220> FEATURE:
<223> OTHER INFORMATION: DNA sequence of HaXAL1 (SEQ ID NO: 2) codon
      optimized for expression in S. cerevisiae

<400> SEQUENCE: 10

```
atgtccacca ccttgatttt gactggtgaa ggtttgggta tcgatgatgt tgttagagtt      60
gctagacacc aagatagagt tgaattgact actgatccag ctattttggc tcaaattgaa     120
gcttcttgcg cctacatcaa tcaagctgta aagaacatc aaccagttta cggtgttact      180
actggttttg gtggtatggc taacgttatt atctctccag aagaagctgc tgaattgcaa     240
aacaacgcta tctggtatca taagactggt gctggtaagt tgttgccatt cactgatgtt     300
agagctgcaa tgttgttgag agctaattca catatgagag gtgcctctgg tattagattg     360
gaaatcatcc aaagaatggt caccttcttg aacgctaatg ttactccaca tgttagagaa     420
ttcggttcta ttggtgcttc tggtgatttg gttccattga tttctattac cggtgctttg     480
ttgggtactg atcaagcttt tatggttgac ttcaacggtg aaaccttgga ttgcatttct     540
gctttggaaa gattgggttt gccaagattg agattgcaac taaagaagg tttagctatg      600 atgaacggta cttctgttat gactggtatt gctgctaact gtgttcatga tgccagaatt     660
ttgttggctt tggctttaga agctcatgcc ttgatgattc aaggtttaca aggtactaat     720
caatccttcc atccattcat ccatagacat aagccacata ctggtcaagt ttgggctgct     780
gatcatatgt tggaattatt gcaaggttcc caattgtcca gaaacgaatt ggatggttct     840
cacgattata gagatggtga cttgattcaa gacagatact cttttgagatg cttgccacaa    900 tttttgggtc aattattga tggtatggcc ttcatctctc atcacttgag agttgaaatc      960
aattccgcta acgataaccc tttgattgat actgcttctg ctgcttctta tcacggtggt    1020
aatttcttgg tcaatatat cggtgttggt atggaccaat tgagatatta catgggtttg     1080
atggctaagc acttggatgt tcaaattgcc ttgttggttt ctccacaatt caacaatggt    1140
ttgccagctt ctttggttgg taacattcaa agaaaggtta tatgggttt aaagggttta    1200 caattgaccg ccaactccat tatgccaatt ttgactttt tgggtaactc cttggctgat    1260
agatttccaa ctcatgccga acaattcaat caaaacatca actcccaagg ttttggttct    1320
gctaatttgg ctagacaaac cattcaaaca ttgcaacaat atatcgccat caccttgatg    1380
tttggtgttc aagctgttga tttgagaacc cataagttgg ctggtcatta caatgctgca    1440
gaattattgt ctccattgac cgctaaaatc taccatgctg ttagatctat cgtcaaacat    1500
ccaccatctc cagaaagacc ttacatttgg aatgatgacg aacaagtttt ggaagcccat    1560
atttcagctt tggctcatga tattgctaac gacggttctt tagttccgc tgttgaacaa    1620 actttgtccg gtttgagatc catcatcttg ttcagatga                           1659
```

<210> SEQ ID NO 11
<211> LENGTH: 14
<212> TYPE: PRT
<213> ORGANISM: Artificial Sequence
<220> FEATURE:
<223> OTHER INFORMATION: His-tag

<400> SEQUENCE: 11

Met Ala His His His His His His Glu Asn Leu Tyr Phe Gln
1               5                   10

<210> SEQ ID NO 12
<211> LENGTH: 59
<212> TYPE: DNA
<213> ORGANISM: Artificial Sequence
<220> FEATURE:
<223> OTHER INFORMATION: Oligonucleotide primer CBJP483

<400> SEQUENCE: 12
catcttagta tattagttaa gtataagaag gagatataca tatgctggca atgagccct         59

<210> SEQ ID NO 13
<211> LENGTH: 41
<212> TYPE: DNA
<213> ORGANISM: Artificial Sequence
<220> FEATURE:
<223> OTHER INFORMATION: Oligonucleotide primer CBJP484

<400> SEQUENCE: 13
tggccggccg atatccaatt gattaaaccg gactctgttg c                           41

<210> SEQ ID NO 14
<211> LENGTH: 62
<212> TYPE: DNA
<213> ORGANISM: Artificial Sequence
<220> FEATURE:
<223> OTHER INFORMATION: Oligonucleotide primer CBJP487

<400> SEQUENCE: 14
catcttagta tattagttaa gtataagaag gagatataca tatggcaccg agcgttgata        60
gc                                                                      62

<210> SEQ ID NO 15
<211> LENGTH: 47
<212> TYPE: DNA
<213> ORGANISM: Artificial Sequence
<220> FEATURE:
<223> OTHER INFORMATION: Oligonucleotide primer CBJP488

<400> SEQUENCE: 15
tggccggccg atatccaatt gattaggcca tcattttaac cagaacc                     47

<210> SEQ ID NO 16
<211> LENGTH: 61
<212> TYPE: DNA
<213> ORGANISM: Artificial Sequence
<220> FEATURE:
<223> OTHER INFORMATION: Oligonucleotide primer CBJP535

<400> SEQUENCE: 16
catcttagta tattagttaa gtataagaag gagatataca tatgacccag gttgttgaac        60
g                                                                       61

<210> SEQ ID NO 17

```
<211> LENGTH: 46
<212> TYPE: DNA
<213> ORGANISM: Artificial Sequence
<220> FEATURE:
<223> OTHER INFORMATION: Oligonucleotide primer CBJP536

<400> SEQUENCE: 17
tggccggccg atatccaatt gattagccaa aatctttacc atctgc              46

<210> SEQ ID NO 18
<211> LENGTH: 60
<212> TYPE: DNA
<213> ORGANISM: Artificial Sequence
<220> FEATURE:
<223> OTHER INFORMATION: Oligonucleotide primer CBJP553

<400> SEQUENCE: 18
catcttagta tattagttaa gtataagaag gagatataca tatgagcacc accctgattc    60

<210> SEQ ID NO 19
<211> LENGTH: 48
<212> TYPE: DNA
<213> ORGANISM: Artificial Sequence
<220> FEATURE:
<223> OTHER INFORMATION: Oligonucleotide primer CBJP554

<400> SEQUENCE: 19
tggccggccg atatccaatt gattagcgaa acagaataat actacgca            48

<210> SEQ ID NO 20
<211> LENGTH: 65
<212> TYPE: DNA
<213> ORGANISM: Artificial Sequence
<220> FEATURE:
<223> OTHER INFORMATION: Oligonucleotide primer CBJP555

<400> SEQUENCE: 20
catcttagta tattagttaa gtataagaag gagatataca tatgaacacc atcaacgaat    60
atctg                                                                65

<210> SEQ ID NO 21
<211> LENGTH: 55
<212> TYPE: DNA
<213> ORGANISM: Artificial Sequence
<220> FEATURE:
<223> OTHER INFORMATION: Oligonucleotide primer CBJP556

<400> SEQUENCE: 21
tggccggccg atatccaatt gattaattgt taatcaggtg gtcttttact ttctg         55

<210> SEQ ID NO 22
<211> LENGTH: 42
<212> TYPE: DNA
<213> ORGANISM: Artificial Sequence
<220> FEATURE:
<223> OTHER INFORMATION: Oligonucleotide CBJP559

<400> SEQUENCE: 22
tatggcccac catcatcacc accatgagaa cctctacttc ca                  42

<210> SEQ ID NO 23
<211> LENGTH: 44
<212> TYPE: DNA
<213> ORGANISM: Artificial Sequence
<220> FEATURE:
<223> OTHER INFORMATION: Oligonucleotide CBJP560
```

-continued

<400> SEQUENCE: 23
gatctggaag tagaggttct catggtggtg atgatggtgg gcca                    44

<210> SEQ ID NO 24
<211> LENGTH: 45
<212> TYPE: DNA
<213> ORGANISM: Artificial Sequence
<220> FEATURE:
<223> OTHER INFORMATION: Oligonucletide primer CBJP561

<400> SEQUENCE: 24
caccaccatg agaacctcta cttccagatg ctggcaatga gccct                   45

<210> SEQ ID NO 25
<211> LENGTH: 47
<212> TYPE: DNA
<213> ORGANISM: Artificial Sequence
<220> FEATURE:
<223> OTHER INFORMATION: Oligonucleotide primer CBJP564

<400> SEQUENCE: 25
caccaccatg agaacctcta cttccagatg acccaggttg ttgaacg                 47

<210> SEQ ID NO 26
<211> LENGTH: 46
<212> TYPE: DNA
<213> ORGANISM: Artificial Sequence
<220> FEATURE:
<223> OTHER INFORMATION: Oligonucleotide primer CBJP573

<400> SEQUENCE: 26
caccaccatg agaacctcta cttccagatg agcaccaccc tgattc                  46

<210> SEQ ID NO 27
<211> LENGTH: 51
<212> TYPE: DNA
<213> ORGANISM: Artificial Sequence
<220> FEATURE:
<223> OTHER INFORMATION: Oligonucleotide primer CBJP574

<400> SEQUENCE: 27
caccaccatg agaacctcta cttccagatg aacaccatca acgaatatct g            51

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide primer CBJP575

<400> SEQUENCE: 28
taatcaattg gatatcggcc ggcca                                         25

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide primer CBJP576

<400> SEQUENCE: 29
catctggaag tagaggttct catggtggtg                                    30

<210> SEQ ID NO 30

```
<211> LENGTH: 26
<212> TYPE: DNA
<213> ORGANISM: Artificial Sequence
<220> FEATURE:
<223> OTHER INFORMATION: oligonucletide PPGK1_rv

<400> SEQUENCE: 30
atgacagaut tgttttatat ttgttg                                              26

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide PPGK1_fw

<400> SEQUENCE: 31
cgtgcgaugg aagtaccttc aaaga                                               25

<210> SEQ ID NO 32
<211> LENGTH: 35
<212> TYPE: DNA
<213> ORGANISM: Artificial Sequence
<220> FEATURE:
<223> OTHER INFORMATION: Oligonucleotide primer CBJP637

<400> SEQUENCE: 32
atctgtcaua aaacaatgac ccaggttgtt gaacg                                    35

<210> SEQ ID NO 33
<211> LENGTH: 32
<212> TYPE: DNA
<213> ORGANISM: Artificial Sequence
<220> FEATURE:
<223> OTHER INFORMATION: Oligonucleotide primer CBJP638

<400> SEQUENCE: 33
cacgcgautc agccaaaatc tttaccatct gc                                       32

<210> SEQ ID NO 34
<211> LENGTH: 34
<212> TYPE: DNA
<213> ORGANISM: Artificial Sequence
<220> FEATURE:
<223> OTHER INFORMATION: Oligonucleotide primer CBJP645

<400> SEQUENCE: 34
atctgtcaua aaacaatgag caccaccctg attc                                     34

<210> SEQ ID NO 35
<211> LENGTH: 34
<212> TYPE: DNA
<213> ORGANISM: Artificial Sequence
<220> FEATURE:
<223> OTHER INFORMATION: Oligonucleotide primer CBJP646

<400> SEQUENCE: 35
cacgcgautc agcgaaacag aataatacta cgca                                     34

<210> SEQ ID NO 36
<211> LENGTH: 39
<212> TYPE: DNA
<213> ORGANISM: Artificial Sequence
<220> FEATURE:
<223> OTHER INFORMATION: Oligonucleotide primer CBJP647

<400> SEQUENCE: 36
```

-continued atctgtcaua aaacaatgaa caccatcaac gaatatctg					39

<210> SEQ ID NO 37
<211> LENGTH: 41
<212> TYPE: DNA
<213> ORGANISM: Artificial Sequence
<220> FEATURE:
<223> OTHER INFORMATION: Oligonucleotide primer CBJP648

<400> SEQUENCE: 37
cacgcgautc aattgttaat caggtggtct tttactttct g					41

<210> SEQ ID NO 38
<211> LENGTH: 37
<212> TYPE: DNA
<213> ORGANISM: Artificial Sequence
<220> FEATURE:
<223> OTHER INFORMATION: Oligonucleotide primer CBJP649

<400> SEQUENCE: 38
atctgtcaua aaacaatgtc caccaccttg attttga					37

<210> SEQ ID NO 39
<211> LENGTH: 35
<212> TYPE: DNA
<213> ORGANISM: Artificial Sequence
<220> FEATURE:
<223> OTHER INFORMATION: Oligonucleotide primer CBJP650

<400> SEQUENCE: 39
cacgcgautc atctgaacaa gatgatggat ctcaa					35

<210> SEQ ID NO 40
<211> LENGTH: 39
<212> TYPE: DNA
<213> ORGANISM: Artificial Sequence
<220> FEATURE:
<223> OTHER INFORMATION: Oligonucleotide primer CBJP651

<400> SEQUENCE: 40
atctgtcaua aaacaatgaa caccatcaac gaatacttg					39

<210> SEQ ID NO 41
<211> LENGTH: 42
<212> TYPE: DNA
<213> ORGANISM: Artificial Sequence
<220> FEATURE:
<223> OTHER INFORMATION: Oligonucleotide primer CBJP652

<400> SEQUENCE: 41
cacgcgautc agttgttaat caagtgatcc ttaactttt gg					42

<210> SEQ ID NO 42
<211> LENGTH: 61
<212> TYPE: DNA
<213> ORGANISM: Artificial Sequence
<220> FEATURE:
<223> OTHER INFORMATION: Oligonucleotide primer CBJP741

<400> SEQUENCE: 42
catcttagta tattagttaa gtataagaag gagatataca tatggcaccg agcctggata					60 g					61

<210> SEQ ID NO 43

```
<211> LENGTH: 40
<212> TYPE: DNA
<213> ORGANISM: Artificial Sequence
<220> FEATURE:
<223> OTHER INFORMATION: Oligonucleotide primer CBJP742

<400> SEQUENCE: 43
tggccggccg atatccaatt gattaggcca gcattttcag                          40

<210> SEQ ID NO 44
<211> LENGTH: 63
<212> TYPE: DNA
<213> ORGANISM: Artificial Sequence
<220> FEATURE:
<223> OTHER INFORMATION: Oligonucleotide primer CBJP743

<400> SEQUENCE: 44
catcttagta tattagttaa gtataagaag gagatataca tatgttcatc gaaaccaatg    60
ttg                                                                  63

<210> SEQ ID NO 45
<211> LENGTH: 45
<212> TYPE: DNA
<213> ORGANISM: Artificial Sequence
<220> FEATURE:
<223> OTHER INFORMATION: Oligonucleotide primer CBJP744

<400> SEQUENCE: 45
tggccggccg atatccaatt gattaaaaca ttttaccaac tgcac                    45

<210> SEQ ID NO 46
<211> LENGTH: 59
<212> TYPE: DNA
<213> ORGANISM: Artificial Sequence
<220> FEATURE:
<223> OTHER INFORMATION: Oligonucleotide primer CBJP752

<400> SEQUENCE: 46
catcttagta tattagttaa gtataagaag gagatataca tatgcgtcat caggttacc     59

<210> SEQ ID NO 47
<211> LENGTH: 46
<212> TYPE: DNA
<213> ORGANISM: Artificial Sequence
<220> FEATURE:
<223> OTHER INFORMATION: Oligonucleotide primer CBJP753

<400> SEQUENCE: 47
tggccggccg atatccaatt gattaggcaa acagaataat actacg                   46

<210> SEQ ID NO 48
<211> LENGTH: 35
<212> TYPE: DNA
<213> ORGANISM: Artificial Sequence
<220> FEATURE:
<223> OTHER INFORMATION: Oligonucleotide primer CBJP754

<400> SEQUENCE: 48
atctgtcaua aaacaatggc accgagcctg gatag                               35

<210> SEQ ID NO 49
<211> LENGTH: 28
<212> TYPE: DNA
<213> ORGANISM: Artificial Sequence
<220> FEATURE:
<223> OTHER INFORMATION: Oligonucleotide primer CBJP755
```

```
<400> SEQUENCE: 49
cacgcgautc aggccagcat tttcagca                                         28

<210> SEQ ID NO 50
<211> LENGTH: 33
<212> TYPE: DNA
<213> ORGANISM: Artificial Sequence
<220> FEATURE:
<223> OTHER INFORMATION: Oligonucleotide primer CBJP762

<400> SEQUENCE: 50
atctgtcaua aaacaatgcg tcatcaggtt acc                                   33

<210> SEQ ID NO 51
<211> LENGTH: 35
<212> TYPE: DNA
<213> ORGANISM: Artificial Sequence
<220> FEATURE:
<223> OTHER INFORMATION: Oligonucleotide primer CBJP763

<400> SEQUENCE: 51
cacgcgautc aggcaaacag aataatacta cgcag                                 35

<210> SEQ ID NO 52
<211> LENGTH: 67
<212> TYPE: DNA
<213> ORGANISM: Artificial Sequence
<220> FEATURE:
<223> OTHER INFORMATION: Oligonucleotide primer CBJP812

<400> SEQUENCE: 52
catcttagta tattagttaa gtataagaag gagatataca tatgccgagc cgtattgatt      60
attacac                                                                67

<210> SEQ ID NO 53
<211> LENGTH: 48
<212> TYPE: DNA
<213> ORGANISM: Artificial Sequence
<220> FEATURE:
<223> OTHER INFORMATION: Oligonucleotide primer CBJP813

<400> SEQUENCE: 53
tggccggccg atatccaatt gattaggctt taatgctttt caccagca                   48

<210> SEQ ID NO 54
<211> LENGTH: 41
<212> TYPE: DNA
<213> ORGANISM: Artificial Sequence
<220> FEATURE:
<223> OTHER INFORMATION: Oligonucleotide primer CBJP815

<400> SEQUENCE: 54
atctgtcaua aaacaatgcc gagccgtatt gattattaca c                          41

<210> SEQ ID NO 55
<211> LENGTH: 34
<212> TYPE: DNA
<213> ORGANISM: Artificial Sequence
<220> FEATURE:
<223> OTHER INFORMATION: Oligonucleotide primer CBJP816

<400> SEQUENCE: 55
cacgcgautc aggctttaat gcttttcacc agca                                  34
```

<210> SEQ ID NO 56
<211> LENGTH: 1571
<212> TYPE: DNA
<213> ORGANISM: Artificial Sequence
<220> FEATURE:
<223> OTHER INFORMATION: RsXal coding sequence (codon optimized for Lactococcus lactis)

<400> SEQUENCE: 56

| | |
|---|---|
| atgcttgcta tgtcaccacc aaaaccagct gttgaattag atcgtcatat tgatttagat | 60 |
| gaagctcatt cagttgcttc aggtggtgct cgtattgttt tagctcctcc agctcgtgat | 120 |
| cgttgtcgtg cttctgaagc tcgtttaggt gctgttattc gtgaagctcg tcatgtttat | 180 |
| ggtttaacaa caggttttgg tccattagct aatcgtcttg tttcaggtga aatgttcgt | 240 |
| acattacaag ctaatttagt tcatcattta gcttcaggtg ttggtccagt tttagattgg | 300 |
| acaacagctc gtgctatggt tttagctcgt ttagttgcaa ttgctcaagg tgcttctggt | 360 |
| gcttcagaag gtacaattgc tcgtcttatt gatttgttaa attcagaatt agctccagct | 420 |
| gttccaatgc gtggtacagt tggtgcttca ggtgatttaa caccattagc tcatatggtt | 480 |
| ctttgtttgc aaggtcgtgg tgattttta gatcgtgatg gtacacgttt agatggtgct | 540 |
| gaaggtttac gtcgtggtcg tttacaacca ttagatcttt cacatcgtga tgctttagct | 600 |
| ttagttaatg gtacatcagc tatgacaggt attgctcttg ttaatgctca tgcttgtcgt | 660 |
| catttaggta attgggctgt tgctcttaca gctttattag ctgaatgttt aggtggtcgt | 720 |
| acagaagctt gggctgctgc tttatcagat ttacgtccac atccaggtca aaaagatgct | 780 |
| gctgctcgtt acgtgctcg tgttgatggt tcagctcgtg ttgttcgtca tgttattgct | 840 |
| gaacgtagat taggtgcttc agatattggt acagaacctg aagctggtca agatgcttat | 900 |
| tcattacgtt gtgctccaca agttttaggt gctggttttg atacattagc ttggcatgat | 960 |
| cgtgttttaa caattgaatt aaatgctgtt acagataatc cagttttttcc accagatggt | 1020 |
| tcagttccag ctttacatgg tggtaatttt atgggtcaac atgttgcttt gacatcagat | 1080 |
| gctttagcaa cagctgttac agttttagct ggattagctg aacgtcaaat tgctcgttta | 1140 |
| actgatgaac gtcttaatcg tggtttgcca ccattttttac atcgtggtcc agctggttta | 1200 |
| aatagtggtt ttatgggtgc tcaagttaca gctactgctt tattagcaga aatgcgtgct | 1260 |
| acaggtccag cttcaattca ttcaattca acaaatgctg ctaatcaaga tgttgtttca | 1320 |
| ttaggaacaa ttgctgctcg tctttgtcgt gaaaaaattg atcgttgggc tgaaattta | 1380 |
| gctattcttg ctctttgtct tgctcaagct gctgaattac gttgtggttc aggattagat | 1440 |
| ggtgtttcac cagctggtaa aaaacttgtt caagctttac gtgaacaatt tccaccactt | 1500 |
| gaaactgatc gtcccacttgg tcaagaaatt gctgctttag ctacacattt attacaacaa | 1560 |
| tcaccagttt a | 1571 |

<210> SEQ ID NO 57
<211> LENGTH: 2142
<212> TYPE: DNA
<213> ORGANISM: Artificial Sequence
<220> FEATURE:
<223> OTHER INFORMATION: RmXal coding sequence (codon optimized for Lactococcus lactis)

<400> SEQUENCE: 57

| | |
|---|---|
| atggctccat cagttgattc aattgctaca tcagttgcta attcattatc aaatggttta | 60 |
| catgctgctg ctgcagctaa tggtggtgat gttcataaaa aaacagctgg tgctggttca | 120 |

```
cttcttccaa caacagaaac aacacaatta gatattgttg aacgtatttt agctgatgct    180
ggtgctacag atcaaattaa acttgatggt tatacattaa cattaggtga tgttgttggt    240
gctgctcgtc gtggtcgttc agttaaagtt gctgattcac cacatattcg tgaaaaaatt    300
gatgcttcag ttgaattttt acgtactcaa ttagataatt cagtttatgg tgttacaaca    360
ggttttggtg gttcagctga tacacgtaca gaagatgcta tttcattaca aaaagcttta    420
ttagaacatc aattatgtgg tgttttacca acatcaatgg atggttttgc tttaggtcgt    480
ggtttagaaa attcattacc attagaagtt gttcgtggtg ctatgacaat cgtgttaat    540 tcattaactc gtggtcattc agctgttcgt attgttgttt tagaagcttt aacaaatttt    600
cttaatcatg gtattacacc aattgttcca ttacgtggta caatttcagc ttcaggtgat    660
ctttcaccat tatcatatat tgctgcttca attacaggac atccagattc aaagttcat    720 gttgatggta aaattatgtc agctcaagaa gctattgctt taaaaggttt acaaccagtt    780 gtttaggtc caaaagaagg tttaggttta gttaatggta cagctgtttc agcttcaatg    840
gctacattag ctttaactga tgctcatgtt ttatcattat agctcaagc tttaactgct    900 ttaacagttg aagctatggt tggtcatgct ggttcatttc atccattttt acatgatgtt    960
acacgtccac atccaacaca aattgaagtt gctcgtaata ttcgtacatt attagaaggt   1020
tcaaaatatg ctgttcatca tgaaactgaa gttaaagtta aagatgatga aggtattta   1080 cgtcaagatc gttatccact cgttgttca ccacaatggt taggtccatt agtttcagat   1140
atgattcatg ctcatgctgt tttatcactt gaagctggtc aatcaacaac tgataatcca   1200
ttaattgatt tagaaaataa aatgacacat catggtggtg cttttatggc ttcttcagtt   1260
ggtaatacaa tggaaaaaac acgtttagct gttgcttaa tgggtaaagt ttcatttaca   1320
caattaacag aaatgttaaa tgctggtatg aatcgtgctt taccatcatg tttagctgct   1380
gaagatccat cactttcata tcattgtaaa ggtttagata ttgctgcagc tgcttataca   1440
tcagaattag gtcatcttgc taatccagtt tcaacacatg ttcaaccagc tgaaatgggt   1500
aatcaagcta ttaattcatt agctcttatt tcagctcgtc gtacagctga agctaatgat   1560
gttctttcat tgttattagc tacacatctt tattgtgttt tacaagctgt tgatttacgt   1620
gctatggaat ttgaacatac taaagctttt gaaccaatgg ttacagaatt acttaaacaa   1680
cattttggtg ctttagctac agctgaagtt gaagataaag ttcgtaaatc aatttataaa   1740
cgtttgcaac aaaataattc atatgattta gaacaacgtt ggcatgatac atttcagtt   1800 gctacaggtg ctgttgttga agctttagct ggtcaagaag tttcacttgc ttcattaaat   1860
gcttggaaag ttgcttgtgc tgaaaaagct attgctctta cacgttcagt tcgtgattca   1920
tttggggctc tccatcatc atcatcacca gctcttaaat atctttctcc acgtacacgt   1980
gttctttatt catttgttcg tgaagaagtt ggagttaaag cacgtcgtgg tgatgtttat   2040
cttggtaaac aagaagttac aattggtaca aatgtttcac gtatttatga agctattaaa   2100
tcaggttgta ttgctccagt tttagttaaa atgatggctt aa                     2142
```

<210> SEQ ID NO 58
<211> LENGTH: 28
<212> TYPE: DNA
<213> ORGANISM: Artificial Sequence
<220> FEATURE:
<223> OTHER INFORMATION: Primer

<400> SEQUENCE: 58

```
ggtgagtgcc tccttataat ttattttg                                          28

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
aagctttctt tgaaccaaaa ttagaaaacc                                        30

<210> SEQ ID NO 60
<211> LENGTH: 54
<212> TYPE: DNA
<213> ORGANISM: Artificial Sequence
<220> FEATURE:
<223> OTHER INFORMATION: Primer

<400> SEQUENCE: 60
caaaataaat tataaggagg cactcaccat gcttgctatg tcaccaccaa aacc             54

<210> SEQ ID NO 61
<211> LENGTH: 57
<212> TYPE: DNA
<213> ORGANISM: Artificial Sequence
<220> FEATURE:
<223> OTHER INFORMATION: Primer

<400> SEQUENCE: 61
ggttttctaa ttttggttca aagaaagctt ttaaactggt gattgttgta ataaatg          57

<210> SEQ ID NO 62
<211> LENGTH: 54
<212> TYPE: DNA
<213> ORGANISM: Artificial Sequence
<220> FEATURE:
<223> OTHER INFORMATION: Primer

<400> SEQUENCE: 62
caaaataaat tataaggagg cactcaccat ggctccatca gttgattcaa ttgc             54

<210> SEQ ID NO 63
<211> LENGTH: 57
<212> TYPE: DNA
<213> ORGANISM: Artificial Sequence
<220> FEATURE:
<223> OTHER INFORMATION: Primer

<400> SEQUENCE: 63
ggttttctaa ttttggttca aagaaagctt ttaagccatc attttaacta aaactgg          57

<210> SEQ ID NO 64
<211> LENGTH: 26
<212> TYPE: DNA
<213> ORGANISM: Artificial Sequence
<220> FEATURE:
<223> OTHER INFORMATION: Primer

<400> SEQUENCE: 64
catgtcatga cccaggttgt tgaacg                                            26

<210> SEQ ID NO 65
<211> LENGTH: 29
<212> TYPE: DNA
<213> ORGANISM: Artificial Sequence
```

<220> FEATURE:
<223> OTHER INFORMATION: Primer

<400> SEQUENCE: 65
gctctagatt agccaaaatc tttaccatc         29

<210> SEQ ID NO 66
<211> LENGTH: 30
<212> TYPE: DNA
<213> ORGANISM: Artificial Sequence
<220> FEATURE:
<223> OTHER INFORMATION: Primer

<400> SEQUENCE: 66
gcggtctccc atgcgtagcg aacagctgac        30

<210> SEQ ID NO 67
<211> LENGTH: 29
<212> TYPE: DNA
<213> ORGANISM: Artificial Sequence
<220> FEATURE:
<223> OTHER INFORMATION: Primer

<400> SEQUENCE: 67
gctctagatt aggccagcag ttcaatcag         29

<210> SEQ ID NO 68
<211> LENGTH: 31
<212> TYPE: DNA
<213> ORGANISM: Artificial Sequence
<220> FEATURE:
<223> OTHER INFORMATION: Primer

<400> SEQUENCE: 68
gcggtctccc atgagcacca ccctgattct g      31

<210> SEQ ID NO 69
<211> LENGTH: 32
<212> TYPE: DNA
<213> ORGANISM: Artificial Sequence
<220> FEATURE:
<223> OTHER INFORMATION: Primer

<400> SEQUENCE: 69
gctctagatt agcgaaacag aataatacta cg     32

<210> SEQ ID NO 70
<211> LENGTH: 28
<212> TYPE: DNA
<213> ORGANISM: Artificial Sequence
<220> FEATURE:
<223> OTHER INFORMATION: Primer

<400> SEQUENCE: 70
catgtcatga acaccatcaa cgaatatc          28

<210> SEQ ID NO 71
<211> LENGTH: 29
<212> TYPE: DNA
<213> ORGANISM: Artificial Sequence
<220> FEATURE:
<223> OTHER INFORMATION: Primer

<400> SEQUENCE: 71
gctctagatt aattgttaat caggtggtc         29

<210> SEQ ID NO 72
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 72
catgtttcct ctccctctca ttttc                                              25

<210> SEQ ID NO 73
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 73
taaggtaata aaaaacacc tcc                                                 23

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 74
tcataccatt tttcacaggg                                                    20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 75
gtctcacttc cttactgcgt                                                    20

<210> SEQ ID NO 76
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 76
gaaaatgaga gggagaggaa acatgaccca ggttgttgaa cg                           42

<210> SEQ ID NO 77
<211> LENGTH: 47
<212> TYPE: DNA
<213> ORGANISM: Artificial Sequence
<220> FEATURE:
<223> OTHER INFORMATION: Oligonucleotide primer

<400> SEQUENCE: 77
ggaggtgttt ttttattacc ttatcagcca aaatctttac catctgc                      47

<210> SEQ ID NO 78
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 78
gaaaatgaga gggagaggaa acatgaacac catcaacgaa tatctg                46

<210> SEQ ID NO 79
<211> LENGTH: 56
<212> TYPE: DNA
<213> ORGANISM: Artificial Sequence
<220> FEATURE:
<223> OTHER INFORMATION: Oligonucleotide primer

<400> SEQUENCE: 79
ggaggtgttt ttttattacc ttatcaattg ttaatcaggt ggtcttttac tttctg      56

<210> SEQ ID NO 80
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 80
cccgcgcgaa tatcgtctgt ccttcttcaa ctaacggggc ag                    42

<210> SEQ ID NO 81
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 81
gaagtacagt aaaagactaa ggttatgtta cagtaatatt gac                   43

<210> SEQ ID NO 82
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 82
gacggttaac tctgtcacaa gcg                                         23

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 83
ccttagtctt ttactgtact tc                                          22

<210> SEQ ID NO 84
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 84
cggaatccaa tatagaagaa tgg                                         23

<210> SEQ ID NO 85

```
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 85
gacagacgat attcgcgcgg g                                              21
```